US009044261B2

(12) United States Patent
Houser

(10) Patent No.: US 9,044,261 B2
(45) Date of Patent: Jun. 2, 2015

(54) TEMPERATURE CONTROLLED ULTRASONIC SURGICAL INSTRUMENTS

(75) Inventor: Kevin L. Houser, Springboro, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 840 days.

(21) Appl. No.: 12/181,816

(22) Filed: Jul. 29, 2008

(65) Prior Publication Data

US 2009/0036914 A1 Feb. 5, 2009

Related U.S. Application Data

(60) Provisional application No. 60/999,735, filed on Jul. 31, 2007.

(51) Int. Cl.

| | |
|---|---|
| ***A61B 17/32*** | (2006.01) |
| *A61B 17/29* | (2006.01) |
| *A61B 17/00* | (2006.01) |

(52) U.S. Cl.

CPC ......... *A61B 17/320092* (2013.01); *A61B 17/29* (2013.01); *A61B 17/320068* (2013.01); *A61B 2017/00084* (2013.01); *A61B 2017/00088* (2013.01); *A61B 2017/00092* (2013.01); *A61B 2017/00106* (2013.01); *A61B 2017/00504* (2013.01); *A61B 2017/00831* (2013.01); *A61B 2017/320084* (2013.01); *A61B 2017/320088* (2013.01)

(58) Field of Classification Search

USPC .............. 606/169–171, 27–52; 600/437–439; 604/19, 22, 27, 30–34, 46, 48, 506, 604/65–67

See application file for complete search history.

(56) References Cited

U.S. PATENT DOCUMENTS

| | | | |
|---|---|---|---|
| 969,528 | A | 9/1910 | Disbrow |
| 1,570,025 | A | 1/1926 | Young |
| 2,704,333 | A | 3/1955 | Calosi et al. |
| 2,736,960 | A | 3/1956 | Armstrong |
| 2,849,788 | A | 9/1958 | Creek |
| RE25,033 | E | 8/1961 | Balamuth et al. |
| 3,015,961 | A | 1/1962 | Roney |
| 3,513,848 | A | 5/1970 | Winston et al. |
| 3,526,219 | A | 9/1970 | Balamuth |
| 3,614,484 | A | 10/1971 | Shoh |
| 3,636,943 | A | 1/1972 | Balamuth |

(Continued)

FOREIGN PATENT DOCUMENTS

| | | | |
|---|---|---|---|
| CN | 1634601 | A | 7/2005 |
| CN | 1640365 | A | 7/2005 |

(Continued)

OTHER PUBLICATIONS

Partial International Search Report for PCT/US2008/071699, Dec. 5, 2008 (2 pages).
U.S. Appl. No. 12/274,884, filed Nov. 20, 2008.
International Search Report for PCT/US2008/071699, Mar. 19, 2009 (11 pages).
Technology Overview, printed from www.harmonicscalpel.com, Internet site, website accessed on Jun. 13, 2007, (3 pages).

(Continued)

*Primary Examiner* — Kathleen Holwerda
*Assistant Examiner* — Sarah W Aleman

(57) ABSTRACT

A surgical instrument includes a transducer configured to produce vibrations at a predetermined frequency. An ultrasonic blade extends along a longitudinal axis and is coupled to the transducer. A controller receives a feedback signal from the ultrasonic blade. A lumen is adapted to couple to a pump. The lumen conducts a fluid therethrough based on the feedback signal.

14 Claims, 24 Drawing Sheets

(56) References Cited

U.S. PATENT DOCUMENTS

| | | | | |
|---|---|---|---|---|
| 3,776,238 | A | 12/1973 | Peyman et al. | |
| 3,805,787 | A | 4/1974 | Banko | |
| 3,830,098 | A | 8/1974 | Antonevich | |
| 3,854,737 | A | 12/1974 | Gilliam, Sr. | |
| 3,862,630 | A | 1/1975 | Balamuth | |
| 3,900,823 | A | 8/1975 | Sokal et al. | |
| 3,918,442 | A | 11/1975 | Nikolaev et al. | |
| 3,946,738 | A | 3/1976 | Newton et al. | |
| 3,955,859 | A | 5/1976 | Stella et al. | |
| 3,956,826 | A | 5/1976 | Perdreaux, Jr. | |
| 4,156,187 | A | 5/1979 | Murry et al. | |
| 4,188,927 | A | 2/1980 | Harris | |
| 4,200,106 | A | 4/1980 | Douvas et al. | |
| 4,306,570 | A | 12/1981 | Matthews | |
| 4,445,063 | A | 4/1984 | Smith | |
| 4,491,132 | A | 1/1985 | Aikins | |
| 4,574,615 | A | 3/1986 | Bower et al. | |
| 4,617,927 | A | 10/1986 | Manes | |
| 4,633,119 | A | 12/1986 | Thompson | |
| 4,634,420 | A | 1/1987 | Spinosa et al. | |
| 4,640,279 | A | 2/1987 | Beard | |
| 4,646,756 | A * | 3/1987 | Watmough et al. | 607/154 |
| 4,649,919 | A | 3/1987 | Thimsen et al. | |
| 4,708,127 | A | 11/1987 | Abdelghani | |
| 4,712,722 | A | 12/1987 | Hood et al. | |
| 4,827,911 | A | 5/1989 | Broadwin et al. | |
| 4,832,683 | A | 5/1989 | Idemoto et al. | |
| 4,838,853 | A | 6/1989 | Parisi | |
| 4,850,354 | A | 7/1989 | McGurk-Burleson et al. | |
| 4,865,159 | A | 9/1989 | Jamison | |
| 4,896,009 | A | 1/1990 | Pawlowski | |
| 4,903,696 | A | 2/1990 | Stasz et al. | |
| 4,922,902 | A | 5/1990 | Wuchinich et al. | |
| 4,965,532 | A | 10/1990 | Sakurai | |
| 4,979,952 | A | 12/1990 | Kubota et al. | |
| 4,981,756 | A | 1/1991 | Rhandhawa | |
| 5,026,387 | A | 6/1991 | Thomas | |
| 5,109,819 | A | 5/1992 | Custer et al. | |
| 5,112,300 | A | 5/1992 | Ureche | |
| 5,123,903 | A | 6/1992 | Quaid et al. | |
| 5,126,618 | A | 6/1992 | Takahashi et al. | |
| 5,162,044 | A | 11/1992 | Gahn et al. | |
| 5,163,537 | A | 11/1992 | Radev | |
| 5,167,725 | A | 12/1992 | Clark et al. | |
| D332,660 | S | 1/1993 | Rawson et al. | |
| 5,176,695 | A | 1/1993 | Dulebohn | |
| 5,184,605 | A | 2/1993 | Grzeszykowski | |
| 5,188,102 | A | 2/1993 | Idemoto et al. | |
| 5,213,569 | A | 5/1993 | Davis | |
| 5,221,282 | A | 6/1993 | Wuchinich | |
| 5,226,909 | A | 7/1993 | Evans et al. | |
| 5,226,910 | A | 7/1993 | Kajiyama et al. | |
| 5,241,236 | A | 8/1993 | Sasaki et al. | |
| 5,257,988 | A | 11/1993 | L'Esperance, Jr. | |
| 5,261,922 | A | 11/1993 | Hood | |
| 5,263,957 | A | 11/1993 | Davison | |
| 5,275,609 | A | 1/1994 | Pingleton et al. | |
| 5,282,800 | A | 2/1994 | Foshee et al. | |
| 5,304,115 | A | 4/1994 | Pflueger, Russell et al. | |
| D347,474 | S | 5/1994 | Olson | |
| 5,322,055 | A | 6/1994 | Davison et al. | |
| 5,324,299 | A | 6/1994 | Davison et al. | |
| 5,326,342 | A | 7/1994 | Pflueger et al. | |
| 5,344,420 | A | 9/1994 | Hilal et al. | |
| 5,346,502 | A | 9/1994 | Estabrook et al. | |
| 5,353,474 | A | 10/1994 | Good et al. | |
| 5,357,423 | A | 10/1994 | Weaver et al. | |
| 5,366,466 | A | 11/1994 | Christian et al. | |
| 5,371,429 | A | 12/1994 | Manna | |
| D354,564 | S | 1/1995 | Medema | |
| 5,381,067 | A | 1/1995 | Greenstein et al. | |
| 5,403,312 | A | 4/1995 | Yates et al. | |
| 5,411,481 | A | 5/1995 | Allen et al. | |
| 5,419,761 | A | 5/1995 | Narayanan et al. | |
| 5,421,829 | A | 6/1995 | Olichney et al. | |
| 5,438,997 | A | 8/1995 | Sieben et al. | |
| 5,449,370 | A | 9/1995 | Vaitekunas | |
| 5,471,988 | A | 12/1995 | Fujio et al. | |
| 5,483,501 | A | 1/1996 | Park et al. | |
| 5,486,162 | A | 1/1996 | Brumbach | |
| 5,500,216 | A | 3/1996 | Julian et al. | |
| 5,501,654 | A | 3/1996 | Failla et al. | |
| 5,505,693 | A | 4/1996 | Mackool | |
| 5,507,738 | A | 4/1996 | Ciervo | |
| 5,527,331 | A | 6/1996 | Kresch et al. | |
| 5,562,609 | A | 10/1996 | Brumbach | |
| 5,562,610 | A | 10/1996 | Brumbach | |
| 5,601,601 | A | 2/1997 | Tal et al. | |
| 5,603,773 | A | 2/1997 | Campbell | |
| 5,607,436 | A | 3/1997 | Pratt et al. | |
| 5,618,492 | A | 4/1997 | Auten et al. | |
| 5,628,760 | A | 5/1997 | Knoepfler | |
| 5,630,420 | A | 5/1997 | Vaitekunas | |
| D381,077 | S | 7/1997 | Hunt | |
| 5,651,780 | A | 7/1997 | Jackson et al. | |
| 5,653,713 | A | 8/1997 | Michelson | |
| 5,669,922 | A | 9/1997 | Hood | |
| 5,674,235 | A | 10/1997 | Parisi | |
| 5,690,269 | A | 11/1997 | Bolanos et al. | |
| 5,694,936 | A | 12/1997 | Fujimoto et al. | |
| 5,713,896 | A | 2/1998 | Nardella | |
| 5,730,752 | A | 3/1998 | Alden et al. | |
| 5,733,074 | A | 3/1998 | Stock et al. | |
| 5,741,226 | A | 4/1998 | Strukel et al. | |
| 5,792,135 | A | 8/1998 | Madhani et al. | |
| 5,808,396 | A | 9/1998 | Boukhny | |
| 5,810,859 | A | 9/1998 | DiMatteo et al. | |
| 5,817,084 | A | 10/1998 | Jensen | |
| 5,817,119 | A | 10/1998 | Klieman et al. | |
| 5,827,323 | A | 10/1998 | Klieman et al. | |
| 5,828,160 | A | 10/1998 | Sugishita | |
| 5,836,897 | A | 11/1998 | Sakurai et al. | |
| 5,843,109 | A | 12/1998 | Mehta et al. | |
| 5,878,193 | A | 3/1999 | Wang et al. | |
| 5,879,364 | A | 3/1999 | Bromfield et al. | |
| 5,883,615 | A | 3/1999 | Fago et al. | |
| 5,893,835 | A | 4/1999 | Witt et al. | |
| 5,897,523 | A | 4/1999 | Wright et al. | |
| 5,897,569 | A * | 4/1999 | Kellogg et al. | 606/169 |
| 5,906,628 | A | 5/1999 | Miyawaki et al. | |
| 5,935,143 | A | 8/1999 | Hood | |
| 5,935,144 | A | 8/1999 | Estabrook | |
| 5,938,633 | A | 8/1999 | Beaupre | |
| 5,944,718 | A | 8/1999 | Austin et al. | |
| 5,944,737 | A | 8/1999 | Tsonton et al. | |
| 5,954,736 | A | 9/1999 | Bishop et al. | |
| 5,954,746 | A | 9/1999 | Holthaus et al. | |
| 5,957,882 | A | 9/1999 | Nita et al. | |
| 5,957,943 | A | 9/1999 | Vaitekunas | |
| 5,968,007 | A | 10/1999 | Simon et al. | |
| 5,968,060 | A | 10/1999 | Kellogg | |
| D416,089 | S | 11/1999 | Barton et al. | |
| 5,980,510 | A | 11/1999 | Tsonton et al. | |
| 5,989,274 | A | 11/1999 | Davison et al. | |
| 5,989,275 | A | 11/1999 | Estabrook et al. | |
| 5,993,972 | A | 11/1999 | Reich et al. | |
| 6,024,741 | A | 2/2000 | Williamson, IV et al. | |
| 6,027,515 | A | 2/2000 | Cimino | |
| 6,033,375 | A | 3/2000 | Brumbach | |
| 6,050,943 | A | 4/2000 | Slayton et al. | |
| 6,051,010 | A | 4/2000 | DiMatteo et al. | |
| 6,056,735 | A | 5/2000 | Okada et al. | |
| 6,063,098 | A | 5/2000 | Houser et al. | |
| 6,066,132 | A | 5/2000 | Chen et al. | |
| 6,068,647 | A | 5/2000 | Witt et al. | |
| 6,077,285 | A | 6/2000 | Boukhny | |
| 6,083,191 | A | 7/2000 | Rose | |
| 6,086,584 | A | 7/2000 | Miller | |
| 6,090,120 | A | 7/2000 | Wright et al. | |
| 6,109,500 | A | 8/2000 | Alli et al. | |
| 6,110,127 | A | 8/2000 | Suzuki | |
| 6,113,594 | A | 9/2000 | Savage | |
| 6,126,629 | A | 10/2000 | Perkins | |
| 6,129,735 | A | 10/2000 | Okada et al. | |

(56) References Cited

U.S. PATENT DOCUMENTS 6,132,368 A 10/2000 Cooper
6,139,320 A 10/2000 Hahn
6,139,561 A 10/2000 Shibata et al.
6,142,615 A 11/2000 Qiu et al.
6,147,560 A 11/2000 Erhage et al.
6,152,902 A 11/2000 Christian et al.
6,159,160 A 12/2000 Hsei et al.
6,159,175 A 12/2000 Strukel et al.
6,165,150 A 12/2000 Banko
6,204,592 B1 3/2001 Hur
6,206,844 B1 3/2001 Reichel et al.
6,210,403 B1 4/2001 Klicek
6,214,023 B1 4/2001 Whipple et al.
6,231,565 B1 5/2001 Tovey et al.
6,233,476 B1 5/2001 Strommer et al.
6,238,366 B1 5/2001 Savage et al.
6,252,110 B1 6/2001 Uemura et al.
D444,365 S 7/2001 Bass et al.
6,254,623 B1 7/2001 Haibel, Jr. et al.
6,258,034 B1 7/2001 Hanafy
6,267,761 B1 7/2001 Ryan
6,270,831 B2 8/2001 Kumar et al.
6,273,852 B1 8/2001 Lehe et al.
6,274,963 B1 8/2001 Estabrook et al.
6,277,115 B1 8/2001 Saadat
6,278,218 B1 8/2001 Madan et al.
6,283,981 B1 9/2001 Beaupre
6,309,400 B2 10/2001 Beaupre
6,319,221 B1 11/2001 Savage et al.
6,325,811 B1 12/2001 Messerly
6,328,751 B1 12/2001 Beaupre
6,340,352 B1 1/2002 Okada et al.
6,352,532 B1 3/2002 Kramer et al.
6,364,888 B1 4/2002 Niemeyer et al.
6,379,320 B1 * 4/2002 Lafon et al. .................. 600/439
D457,958 S 5/2002 Dycus et al.
6,383,194 B1 5/2002 Pothula
6,387,109 B1 5/2002 Davison et al.
6,388,657 B1 5/2002 Natoli
6,391,042 B1 5/2002 Cimino
6,405,733 B1 6/2002 Fogarty et al.
6,416,486 B1 7/2002 Wampler
6,423,073 B2 7/2002 Bowman
6,423,082 B1 7/2002 Houser et al.
6,428,539 B1 8/2002 Baxter et al.
6,432,118 B1 8/2002 Messerly
6,436,114 B1 8/2002 Novak et al.
6,436,115 B1 8/2002 Beaupre
6,443,969 B1 9/2002 Novak et al.
6,454,781 B1 9/2002 Witt et al.
6,454,782 B1 9/2002 Schwemberger
6,458,142 B1 10/2002 Faller et al.
6,480,796 B2 11/2002 Wiener
6,485,490 B2 11/2002 Wampler et al.
6,491,708 B2 12/2002 Madan et al.
6,497,715 B2 12/2002 Satou
6,500,176 B1 12/2002 Truckai et al.
6,500,188 B2 12/2002 Harper et al.
6,524,251 B2 2/2003 Rabiner et al.
6,524,316 B1 2/2003 Nicholson et al.
6,527,736 B1 3/2003 Attinger et al.
6,533,784 B2 3/2003 Truckai et al.
6,537,291 B2 3/2003 Friedman et al.
6,543,452 B1 4/2003 Lavigne
6,543,456 B1 4/2003 Freeman
6,544,260 B1 4/2003 Markel et al.
6,561,983 B2 5/2003 Cronin et al.
6,572,632 B2 6/2003 Zisterer et al.
6,575,969 B1 * 6/2003 Rittman et al. ................. 606/41
6,582,451 B1 6/2003 Marucci et al.
6,589,200 B1 7/2003 Schwemberger et al.
6,589,239 B2 7/2003 Khandkar et al.
6,610,059 B1 8/2003 West, Jr.
6,616,450 B2 9/2003 Mossle et al.
6,623,501 B2 9/2003 Heller et al.
6,626,926 B2 9/2003 Friedman et al.
6,633,234 B2 10/2003 Wiener et al.
6,656,177 B2 12/2003 Truckai et al.
6,662,127 B2 12/2003 Wiener et al.
6,663,941 B2 12/2003 Brown et al.
6,669,690 B1 12/2003 Okada et al.
6,676,660 B2 1/2004 Wampler et al.
6,678,621 B2 1/2004 Stulen et al.
6,679,899 B2 1/2004 Wiener et al.
6,682,544 B2 1/2004 Mastri et al.
6,689,146 B1 2/2004 Himes
6,716,215 B1 4/2004 David et al.
6,731,047 B2 5/2004 Kauf et al.
6,733,506 B1 5/2004 McDevitt et al.
6,762,535 B2 7/2004 Take et al.
6,770,072 B1 8/2004 Truckai et al.
6,773,443 B2 8/2004 Truwit et al.
6,773,444 B2 8/2004 Messerly
6,783,524 B2 8/2004 Anderson et al.
6,786,382 B1 9/2004 Hoffman
6,786,383 B2 9/2004 Stegelmann
6,790,216 B1 9/2004 Ishikawa
6,802,843 B2 10/2004 Truckai et al.
6,827,712 B2 12/2004 Tovey et al.
6,828,712 B2 12/2004 Battaglin et al.
6,869,439 B2 3/2005 White et al.
6,875,220 B2 4/2005 Du et al.
6,905,497 B2 6/2005 Truckai et al.
6,908,472 B2 6/2005 Wiener et al.
6,913,579 B2 7/2005 Truckai et al.
6,923,804 B2 8/2005 Eggers et al.
6,926,716 B2 8/2005 Baker et al.
6,929,632 B2 8/2005 Nita et al.
6,929,644 B2 8/2005 Truckai et al.
6,933,656 B2 8/2005 Matsushita et al.
D509,589 S 9/2005 Wells
6,942,677 B2 9/2005 Nita et al.
6,945,981 B2 9/2005 Donofrio et al.
D511,145 S 11/2005 Donofrio et al.
6,976,844 B2 12/2005 Hickok et al.
6,976,969 B2 12/2005 Messerly
6,977,495 B2 12/2005 Donofrio
6,984,220 B2 1/2006 Wuchinich
7,001,335 B2 2/2006 Adachi et al.
7,011,657 B2 3/2006 Truckai et al.
7,033,357 B2 4/2006 Baxter et al.
7,041,083 B2 5/2006 Chu et al.
7,041,088 B2 5/2006 Nawrocki et al.
7,041,102 B2 5/2006 Truckai et al.
7,070,597 B2 7/2006 Truckai et al.
7,074,219 B2 7/2006 Levine et al.
7,077,039 B2 7/2006 Gass et al.
7,077,853 B2 * 7/2006 Kramer et al. ................ 606/169
7,083,619 B2 8/2006 Truckai et al.
7,087,054 B2 8/2006 Truckai et al.
7,090,672 B2 8/2006 Underwood et al.
7,101,378 B2 9/2006 Salameh et al.
7,108,695 B2 9/2006 Witt et al.
7,112,201 B2 9/2006 Truckai et al.
7,118,564 B2 10/2006 Ritchie et al.
7,124,932 B2 10/2006 Isaacson et al.
7,125,409 B2 10/2006 Truckai et al.
7,135,018 B2 11/2006 Ryan et al.
7,135,030 B2 11/2006 Schwemberger et al.
7,144,403 B2 12/2006 Booth
7,153,315 B2 12/2006 Miller
D536,093 S 1/2007 Nakajima et al.
7,156,189 B1 1/2007 Bar-Cohen et al.
7,156,853 B2 1/2007 Muratsu
7,157,058 B2 1/2007 Marhasin et al.
7,159,750 B2 1/2007 Racenet et al.
7,163,548 B2 1/2007 Stulen et al.
7,169,146 B2 1/2007 Truckai et al.
7,179,271 B2 2/2007 Friedman et al.
7,186,253 B2 3/2007 Truckai et al.
7,189,233 B2 3/2007 Truckai et al.
7,204,820 B2 4/2007 Akahoshi
7,217,269 B2 5/2007 El-Galley et al.
7,220,951 B2 5/2007 Truckai et al.

(56) References Cited

U.S. PATENT DOCUMENTS 7,223,229 B2 5/2007 Inman et al.
7,229,455 B2 6/2007 Sakurai et al.
7,273,483 B2 9/2007 Wiener et al.
7,285,895 B2 10/2007 Beaupré
7,309,849 B2 12/2007 Truckai et al.
7,311,709 B2 12/2007 Truckai et al.
7,317,955 B2 1/2008 McGreevy
7,326,236 B2 2/2008 Andreas et al.
7,331,410 B2 2/2008 Yong et al.
7,353,068 B2 4/2008 Tanaka et al.
7,354,440 B2 4/2008 Truckal et al.
7,380,695 B2 6/2008 Doll et al.
7,380,696 B2 6/2008 Shelton, IV et al.
7,381,209 B2 6/2008 Truckai et al.
7,390,317 B2 6/2008 Taylor et al.
7,404,508 B2 7/2008 Smith et al.
7,408,288 B2 8/2008 Hara
D576,725 S 9/2008 Shumer et al.
D578,643 S 10/2008 Shumer et al.
D578,644 S 10/2008 Shumer et al.
D578,645 S 10/2008 Shumer et al.
7,431,704 B2 10/2008 Babaev
7,441,684 B2 10/2008 Shelton, IV et al.
7,455,208 B2 11/2008 Wales et al.
7,472,815 B2 1/2009 Shelton, IV et al.
7,473,263 B2 1/2009 Johnston et al.
7,479,148 B2 1/2009 Beaupre
7,479,160 B2 1/2009 Branch et al.
7,494,468 B2 2/2009 Rabiner et al.
7,503,893 B2 3/2009 Kucklick
7,503,895 B2 3/2009 Rabiner et al.
7,506,790 B2 3/2009 Shelton, IV
7,506,791 B2 3/2009 Omaits et al.
7,524,320 B2 4/2009 Tierney et al.
7,534,243 B1 5/2009 Chin et al.
D594,983 S 6/2009 Price et al.
7,549,564 B2 6/2009 Boudreaux
7,559,450 B2 7/2009 Wales et al.
7,567,012 B2 7/2009 Namikawa
7,578,820 B2 8/2009 Moore et al.
7,654,431 B2 2/2010 Hueil et al.
7,665,647 B2 2/2010 Shelton, IV et al.
7,670,334 B2 3/2010 Hueil et al.
7,674,263 B2 3/2010 Ryan
7,691,098 B2 4/2010 Wallace et al.
7,713,202 B2 5/2010 Boukhny et al.
7,714,481 B2 5/2010 Sakai
D618,797 S 6/2010 Price et al.
7,751,115 B2 7/2010 Song
7,770,774 B2 8/2010 Mastri et al.
7,770,775 B2 8/2010 Shelton, IV et al.
7,780,054 B2 8/2010 Wales
7,780,659 B2 8/2010 Okada et al.
7,784,662 B2 8/2010 Wales et al.
7,798,386 B2 9/2010 Schall et al.
7,806,891 B2 10/2010 Nowlin et al.
7,810,693 B2 10/2010 Broehl et al.
7,824,401 B2 11/2010 Manzo et al.
7,837,699 B2 11/2010 Yamada et al.
7,854,735 B2 12/2010 Houser et al.
D631,155 S 1/2011 Peine et al.
7,861,906 B2 1/2011 Doll et al.
7,876,030 B2 1/2011 Taki et al.
D631,965 S 2/2011 Price et al.
7,892,606 B2 2/2011 Thies et al.
7,901,423 B2 3/2011 Stulen et al.
7,905,881 B2 3/2011 Masuda et al.
7,922,651 B2 4/2011 Yamada et al.
7,959,050 B2 6/2011 Smith et al.
7,959,626 B2 6/2011 Hong et al.
7,976,544 B2 7/2011 McClurken et al.
7,998,157 B2 8/2011 Culp et al.
8,038,693 B2 10/2011 Allen
8,061,014 B2 11/2011 Smith et al.
8,089,197 B2 1/2012 Rinner et al.
8,152,825 B2 4/2012 Madan et al.
8,157,145 B2 4/2012 Shelton, IV et al.
8,162,966 B2 4/2012 Connor et al.
8,177,800 B2 5/2012 Spitz et al.
D661,801 S 6/2012 Price et al.
D661,802 S 6/2012 Price et al.
D661,803 S 6/2012 Price et al.
D661,804 S 6/2012 Price et al.
8,197,502 B2 6/2012 Smith et al.
8,236,020 B2 8/2012 Smith et al.
8,253,303 B2 8/2012 Giordano et al.
8,333,778 B2 12/2012 Smith et al.
8,333,779 B2 12/2012 Smith et al.
8,334,468 B2 12/2012 Palmer et al.
8,338,726 B2 12/2012 Palmer et al.
8,372,101 B2 2/2013 Smith et al.
8,372,102 B2 2/2013 Stulen et al.
8,377,059 B2 2/2013 Deville et al.
8,377,085 B2 2/2013 Smith et al.
8,418,349 B2 4/2013 Smith et al.
8,439,939 B2 5/2013 Deville et al.
8,535,340 B2 9/2013 Allen
8,535,341 B2 9/2013 Allen
2001/0025184 A1 9/2001 Messerly
2001/0031950 A1 10/2001 Ryan
2001/0039419 A1 11/2001 Francischelli et al.
2002/0002377 A1 1/2002 Cimino
2002/0019649 A1 2/2002 Sikora et al.
2002/0022836 A1 2/2002 Goble et al.
2002/0049551 A1 4/2002 Friedman et al.
2002/0052617 A1 5/2002 Anis et al.
2002/0077550 A1 6/2002 Rabiner et al.
2002/0156493 A1 10/2002 Houser et al.
2003/0036705 A1 2/2003 Hare et al.
2003/0055443 A1 3/2003 Spotnitz
2003/0204199 A1 10/2003 Novak et al.
2003/0212332 A1 11/2003 Fenton et al.
2003/0212422 A1 11/2003 Fenton et al.
2003/0229344 A1 12/2003 Dycus et al.
2004/0030254 A1 2/2004 Babaev
2004/0047485 A1 3/2004 Sherrit et al.
2004/0054364 A1 3/2004 Aranyi et al.
2004/0092921 A1 5/2004 Kadziauskas et al.
2004/0097919 A1 5/2004 Wellman et al.
2004/0097996 A1 5/2004 Rabiner et al.
2004/0199193 A1 10/2004 Hayashi et al.
2004/0204728 A1* 10/2004 Haefner ........................ 606/169
2004/0260300 A1 12/2004 Gorensek et al.
2005/0021065 A1 1/2005 Yamada et al.
2005/0033337 A1 2/2005 Muir et al.
2005/0049546 A1 3/2005 Messerly et al.
2005/0070800 A1 3/2005 Takahashi
2005/0096683 A1 5/2005 Ellins et al.
2005/0143769 A1 6/2005 White et al.
2005/0149108 A1 7/2005 Cox
2005/0165345 A1 7/2005 Laufer et al.
2005/0177184 A1 8/2005 Easley
2005/0192610 A1 9/2005 Houser et al.
2005/0209620 A1 9/2005 Du et al.
2005/0261581 A1 11/2005 Hughes et al.
2005/0261588 A1 11/2005 Makin et al.
2005/0273090 A1 12/2005 Nieman et al.
2005/0288659 A1 12/2005 Kimura et al.
2006/0030797 A1 2/2006 Zhou et al.
2006/0063130 A1 3/2006 Hayman et al.
2006/0079878 A1 4/2006 Houser
2006/0084963 A1 4/2006 Messerly
2006/0095046 A1 5/2006 Trieu et al.
2006/0190034 A1 8/2006 Nishizawa et al.
2006/0206115 A1 9/2006 Schomer et al.
2006/0211943 A1 9/2006 Beaupre
2006/0235306 A1 10/2006 Cotter et al.
2006/0253050 A1 11/2006 Yoshimine et al.
2006/0264809 A1 11/2006 Hansmann et al.
2007/0016235 A1 1/2007 Tanaka et al.
2007/0016236 A1 1/2007 Beaupre
2007/0055228 A1 3/2007 Berg et al.
2007/0056596 A1 3/2007 Fanney et al.
2007/0060915 A1 3/2007 Kucklick

(56) References Cited

U.S. PATENT DOCUMENTS

2007/0060935 A1 3/2007 Schwardt et al.
2007/0063618 A1 3/2007 Bromfield
2007/0106317 A1 5/2007 Shelton et al.
2007/0129716 A1 6/2007 Daw et al.
2007/0130771 A1 6/2007 Ehlert et al.
2007/0131034 A1 6/2007 Ehlert et al.
2007/0149881 A1 6/2007 Rabin
2007/0162050 A1 7/2007 Sartor
2007/0173872 A1 7/2007 Neuenfeldt
2007/0185380 A1 8/2007 Kucklick
2007/0219481 A1 9/2007 Babaev
2007/0239028 A1 10/2007 Houser et al.
2007/0249941 A1 10/2007 Salehi et al.
2007/0260234 A1 11/2007 McCullagh et al.
2007/0265560 A1 11/2007 Soltani et al.
2007/0275348 A1 11/2007 Lemon
2007/0282335 A1 12/2007 Young et al.
2007/0287933 A1 12/2007 Phan et al.
2008/0009848 A1 1/2008 Paraschiv et al.
2008/0051812 A1 2/2008 Schmitz et al.
2008/0058585 A1 3/2008 Novak et al.
2008/0058775 A1 3/2008 Darian et al.
2008/0058845 A1 3/2008 Shimizu et al.
2008/0082039 A1 4/2008 Babaev
2008/0082098 A1 4/2008 Tanaka et al.
2008/0171938 A1 7/2008 Masuda et al.
2008/0172051 A1 7/2008 Masuda et al.
2008/0177268 A1 7/2008 Daum et al.
2008/0188878 A1 8/2008 Young
2008/0200940 A1 8/2008 Eichmann et al.
2008/0208231 A1 8/2008 Ota et al.
2008/0234708 A1 9/2008 Houser et al.
2008/0234709 A1 9/2008 Houser
2008/0234710 A1 9/2008 Neurohr et al.
2008/0234711 A1 9/2008 Houser et al.
2008/0243106 A1 10/2008 Coe et al.
2008/0245371 A1 10/2008 Gruber
2008/0249553 A1 10/2008 Gruber et al.
2008/0262490 A1 10/2008 Williams
2008/0281200 A1* 11/2008 Voic et al. .................... 600/439
2008/0287948 A1 11/2008 Newton et al.
2009/0030311 A1 1/2009 Stulen et al.
2009/0030351 A1 1/2009 Wiener et al.
2009/0030437 A1 1/2009 Houser et al.
2009/0030438 A1 1/2009 Stulen
2009/0030439 A1 1/2009 Stulen
2009/0036911 A1 2/2009 Stulen
2009/0036912 A1 2/2009 Wiener et al.
2009/0036913 A1 2/2009 Wiener et al.
2009/0048537 A1 2/2009 Lydon et al.
2009/0054886 A1 2/2009 Yachi et al.
2009/0054894 A1 2/2009 Yachi
2009/0076506 A1 3/2009 Baker
2009/0082716 A1 3/2009 Akahoshi
2009/0105750 A1 4/2009 Price et al.
2009/0118802 A1 5/2009 Mioduski et al.
2009/0138006 A1 5/2009 Bales et al.
2009/0143795 A1 6/2009 Robertson
2009/0143797 A1 6/2009 Smith et al.
2009/0143798 A1 6/2009 Smith et al.
2009/0143799 A1 6/2009 Smith et al.
2009/0143800 A1 6/2009 Deville et al.
2009/0143801 A1 6/2009 Deville et al.
2009/0143802 A1 6/2009 Deville et al.
2009/0143803 A1 6/2009 Palmer et al.
2009/0143804 A1 6/2009 Palmer et al.
2009/0143805 A1 6/2009 Palmer et al.
2009/0143806 A1 6/2009 Witt et al.
2009/0149801 A1 6/2009 Crandall et al.
2009/0270853 A1 10/2009 Yachi et al.
2009/0270899 A1 10/2009 Carusillo et al.
2009/0318945 A1 12/2009 Yoshimine et al.
2009/0327715 A1 12/2009 Smith et al.
2010/0004668 A1 1/2010 Smith et al.
2010/0004669 A1 1/2010 Smith et al.
2010/0016785 A1 1/2010 Takuma
2010/0030248 A1 2/2010 Palmer et al.
2010/0036370 A1 2/2010 Mirel et al.
2010/0036405 A1 2/2010 Giordano et al.
2010/0069940 A1 3/2010 Miller et al.
2010/0158307 A1 6/2010 Kubota et al.
2010/0179577 A1 7/2010 Houser
2010/0187283 A1 7/2010 Crainich et al.
2010/0193567 A1 8/2010 Scheib et al.
2010/0234906 A1 9/2010 Koh
2010/0268211 A1 10/2010 Manwaring et al.
2010/0298743 A1 11/2010 Nield et al.
2010/0298851 A1 11/2010 Nield
2010/0331869 A1 12/2010 Voegele et al.
2010/0331870 A1 12/2010 Wan et al.
2010/0331871 A1 12/2010 Nield et al.
2010/0331872 A1 12/2010 Houser et al.
2011/0009850 A1 1/2011 Main et al.
2011/0015627 A1 1/2011 Dinardo et al.
2011/0015631 A1 1/2011 Wiener et al.
2011/0015660 A1 1/2011 Wiener et al.
2011/0082486 A1 4/2011 Messerly et al.
2011/0087212 A1 4/2011 Aldridge et al.
2011/0087213 A1 4/2011 Messerly et al.
2011/0087214 A1 4/2011 Giordano et al.
2011/0087215 A1 4/2011 Aldridge et al.
2011/0087216 A1 4/2011 Aldridge et al.
2011/0087217 A1 4/2011 Yates et al.
2011/0087218 A1 4/2011 Boudreaux et al.
2011/0087256 A1 4/2011 Wiener et al.
2011/0125175 A1 5/2011 Stulen et al.
2011/0196286 A1 8/2011 Robertson et al.
2011/0196287 A1 8/2011 Robertson et al.
2011/0196398 A1 8/2011 Robertson et al.
2011/0196399 A1 8/2011 Robertson et al.
2011/0196400 A1 8/2011 Robertson et al.
2011/0196401 A1 8/2011 Robertson et al.
2011/0196402 A1 8/2011 Robertson et al.
2011/0196403 A1 8/2011 Robertson et al.
2011/0196404 A1 8/2011 Dietz et al.
2011/0196405 A1 8/2011 Dietz
2011/0288452 A1 11/2011 Houser et al.
2012/0029546 A1 2/2012 Robertson
2012/0059289 A1 3/2012 Nield et al.
2012/0078139 A1 3/2012 Aldridge et al.
2012/0078247 A1 3/2012 Worrell et al.
2012/0083783 A1 4/2012 Davison et al.
2012/0083784 A1 4/2012 Davison et al.
2012/0132450 A1 5/2012 Timm et al.
2012/0138660 A1 6/2012 Shelton, IV
2012/0177005 A1 7/2012 Liang et al.
2012/0184946 A1 7/2012 Price et al.
2012/0199630 A1 8/2012 Shelton, IV
2012/0199631 A1 8/2012 Shelton, IV et al.
2012/0199632 A1 8/2012 Spivey et al.
2012/0199633 A1 8/2012 Shelton, IV et al.
2012/0203247 A1 8/2012 Shelton, IV et al.
2012/0205421 A1 8/2012 Shelton, IV
2012/0210223 A1 8/2012 Eppolito
2012/0211546 A1 8/2012 Shelton, IV
2012/0259353 A1 10/2012 Houser et al.
2012/0265196 A1 10/2012 Turner et al.
2012/0269676 A1 10/2012 Houser et al.
2012/0289984 A1 11/2012 Houser et al.
2012/0310262 A1 12/2012 Messerly et al.
2012/0310263 A1 12/2012 Messerly et al.
2012/0310264 A1 12/2012 Messerly et al.
2012/0323265 A1 12/2012 Stulen
2013/0012970 A1 1/2013 Houser

FOREIGN PATENT DOCUMENTS

CN 1694649 A 11/2005
CN 1922563 A 2/2007
CN 101040799 A 9/2007
EP 0171967 A2 2/1986
EP 0443256 A1 8/1991
EP 0456470 A1 11/1991
EP 0612570 B1 4/1992

(56) References Cited

FOREIGN PATENT DOCUMENTS

| | | | |
|---|---|---|---|
| EP | 0482195 | B1 | 1/1996 |
| EP | 0612570 | B1 | 6/1997 |
| EP | 0908148 | B1 | 1/2002 |
| EP | 0908155 | B1 | 6/2003 |
| EP | 1199044 | B1 | 12/2005 |
| EP | 1199043 | B1 | 3/2006 |
| EP | 1433425 | B1 | 6/2006 |
| EP | 1844720 | A1 | 10/2007 |
| EP | 1862133 | A1 | 12/2007 |
| EP | 1199045 | B1 | 6/2008 |
| EP | 1974771 | A1 | 10/2008 |
| EP | 1832259 | B1 | 6/2009 |
| EP | 2074959 | A1 | 7/2009 |
| EP | 2298154 | A2 | 3/2011 |
| GB | 2032221 | A | 4/1980 |
| GB | 2379878 | B | 11/2004 |
| GB | 2447767 | B | 8/2011 |
| JP | 62-2292153 | A | 12/1987 |
| JP | 63-315049 | A | 12/1988 |
| JP | H 01-151452 | A | 6/1989 |
| JP | H 01-198540 | A | 8/1989 |
| JP | 02-71510 | U | 5/1990 |
| JP | 04-25707 | U | 2/1992 |
| JP | 4-30508 | U | 3/1992 |
| JP | 6-104503 | A | 4/1994 |
| JP | 6-507081 | A | 8/1994 |
| JP | 7-508910 | A | 10/1995 |
| JP | 7-308323 | A | 11/1995 |
| JP | H 08-336545 | A | 12/1996 |
| JP | 11-253451 | A | 9/1999 |
| JP | 2002-186901 | A | 7/2002 |
| JP | 2003-010201 | | 1/2003 |
| JP | 2003-126110 | A | 5/2003 |
| JP | 2003-310627 | A | 5/2003 |
| JP | 2003-530921 | A | 10/2003 |
| JP | 2003-339730 | A | 12/2003 |
| JP | 2005027026 | A | 1/2005 |
| JP | 2005-534451 | A | 11/2005 |
| JP | 2006217716 | A | 8/2006 |
| JP | 2008-508065 | A | 3/2008 |
| JP | 2008-119250 | A | 5/2008 |
| JP | 2009-511206 | A | 3/2009 |
| WO | WO 92/22259 | A2 | 12/1992 |
| WO | WO 93/14708 | A1 | 8/1993 |
| WO | WO 98/26739 | A1 | 6/1998 |
| WO | WO 98/37815 | A1 | 9/1998 |
| WO | WO 01/54590 | A1 | 8/2001 |
| WO | WO 01/95810 | A2 | 12/2001 |
| WO | WO 2004/037095 | A2 | 5/2004 |
| WO | WO 2005/122917 | A1 | 12/2005 |
| WO | WO 2006/012797 | A1 | 2/2006 |
| WO | WO 2006/042210 | A2 | 4/2006 |
| WO | WO 2006/058223 | A2 | 6/2006 |
| WO | WO 2006/063199 | A2 | 6/2006 |
| WO | WO 2006/083988 | A1 | 8/2006 |
| WO | WO 2006/129465 | A1 | 12/2006 |
| WO | WO 2007/008710 | A2 | 1/2007 |
| WO | WO 2007/047531 | A2 | 4/2007 |
| WO | WO 2007/143665 | A2 | 12/2007 |
| WO | WO 2008/016886 | A2 | 2/2008 |
| WO | WO 2008/042021 | A1 | 4/2008 |
| WO | WO 2008/130793 | A1 | 10/2008 |
| WO | WO 2009/018406 | A2 | 2/2009 |
| WO | WO 2009/027065 | A1 | 3/2009 |
| WO | WO 2011/144911 | A1 | 11/2011 |

OTHER PUBLICATIONS

Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.

AST Products, Inc., "Principles ofVideo Contact Angle Analysis," 20 pages, (date unknown).

Lim et al., "A Review of Mechanism Used in Laparoscopic Surgical Instruments," Mechanism and Machine Theory, vol. 38, pp. 1133-1147, (2003).

Gooch et al., "Recommended Infection-Control Practices for Dentistry, 1993," Published: May 28, 1993; [retrieved on Aug. 23, 2008]. Retrieved from the internet: URL: http//wonder.cdc.gov/wonder/prevguid/p0000191/p0000191.asp (15 pages).

U.S. Appl. No. 11/881,602, filed Jul. 27, 2007.

U.S. Appl. No. 11/888,081, filed Jul. 31, 2007.

U.S. Appl. No. 11/881,636, filed Jul. 27, 2007.

U.S. Appl. No. 11/881,645, filed Jul. 27, 2007.

U.S. Appl. No. 11/881,654, filed Jul. 27, 2007.

U.S. Appl. No. 11/888,171, filed Jul. 31, 2007.

U.S. Appl. No. 11/998,758, filed Nov. 30, 2007.

U.S. Appl. No. 11/881,662, filed Jul. 27, 2007.

U.S. Appl. No. 11/888,222, filed Jul. 31, 2007.

U.S. Appl. No. 12/245,158, filed Oct. 3, 2008.

U.S. Appl. No. 29/292,295, filed Oct. 5, 2007.

U.S. Appl. No. 11/998,543, filed Nov. 30, 2007.

U.S. Appl. No. 29/327,737, filed Nov. 12, 2008.

Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).

Incropera et al., Fundamentals of Heat and Mass Transfer, Wiley, New York (1990). (Book—not attached).

F. A. Duck, "Optical Properties of Tissue Including Ultraviolet and Infrared Radiation," pp. 43-71 in *Physical Properties of Tissue* (1990).

Orr et al., "Overview of Bioheat Transfer," pp. 367-384 in Optical-Thermal Response of Laser-Irradiated Tissue, A. J. Welch and M. J. C. van Gernert, eds., Plenum, New York (1995).

Campbell et al, "Thermal Imaging in Surgery," p. 19-3, in *Medical Infrared Imaging*, N. A. Diakides and J. D. Bronzino, Eds. (2008).

AST Products, Inc., "Principles ofVideo Contact Angle Analysis," 20 pages, (2006).

U.S. Appl. No. 12/703,860, filed Feb. 11, 2010.

U.S. Appl. No. 12/703,864, filed Feb. 11, 2010.

U.S. Appl. No. 12/703,866, filed Feb. 11, 2010.

U.S. Appl. No. 12/703,870, filed Feb. 11, 2010.

U.S. Appl. No. 12/703,875, filed Feb. 11, 2010.

U.S. Appl. No. 12/703,877, filed Feb. 11, 2010.

U.S. Appl. No. 12/703,879, filed Feb. 11, 2010.

U.S. Appl. No. 12/703,885, filed Feb. 11, 2010.

U.S. Appl. No. 12/703,893, filed Feb. 11, 2010.

U.S. Appl. No. 12/703,899, filed Feb. 11, 2010.

U.S. Appl. No. 12/896,351, filed Oct. 1, 2010.

U.S. Appl. No. 12/896,411, filed Oct. 1, 2010.

U.S. Appl. No. 12/896,420, filed Oct. 1, 2010.

U.S. Appl. No. 29/402,697, filed Sep. 26, 2011.

U.S. Appl. No. 29/402,699, filed Sep. 26, 2011.

U.S. Appl. No. 29/402,700, filed Sep. 26, 2011.

U.S. Appl. No. 29/402,701, filed Sep. 26, 2011.

U.S. Appl. No. 13/270,459, filed Oct. 11, 2011.

U.S. Appl. No. 13/251,766, filed Oct. 3, 2011.

U.S. Appl. No. 29/404,676, filed Oct. 24, 2011.

U.S. Appl. No. 13/151,181, filed Jun. 2, 2011.

U.S. Appl. No. 13/369,561, filed Feb. 9, 2012.

U.S. Appl. No. 13/369,569, filed Feb. 9, 2012.

U.S. Appl. No. 13/369,578, filed Feb. 9, 2012.

U.S. Appl. No. 13/369,584, filed Feb. 9, 2012.

U.S. Appl. No. 13/369,588, filed Feb. 9, 2012.

U.S. Appl. No. 13/369,594, filed Feb. 9, 2012.

U.S. Appl. No. 13/369,601, filed Feb. 9, 2012.

U.S. Appl. No. 13/369,609, filed Feb. 9, 2012.

U.S. Appl. No. 13/369,629, filed Feb. 9, 2012.

U.S. Appl. No. 13/369,666, filed Feb. 9, 2012.

U.S. Appl. No. 13/584,020, filed Aug. 13, 2012.

U.S. Appl. No. 13/584,445, filed Aug. 13, 2012.

* cited by examiner

TEMPERATURE CONTROLLED ULTRASONIC SURGICAL INSTRUMENTS

PRIORITY CLAIM

This application claims the benefit of provisional application Ser. No. 60/999,735, filed Jul. 31, 2007, which is a conversion of application Ser. No. 11/888,296, filed Jul. 31, 2007. These applications to which Applicant claims priority are relied upon and incorporated herein by reference.

BACKGROUND

Ultrasonic instruments, including both hollow core and solid core instruments, are used for the safe and effective treatment of many medical conditions. Ultrasonic instruments, and particularly solid core ultrasonic instruments, are advantageous because they may be used to cut and/or coagulate tissue using energy in the form of mechanical vibrations transmitted to a surgical end effector at ultrasonic frequencies. Ultrasonic vibrations, when transmitted to tissue at suitable energy levels and using a suitable end effector, may be used to cut, dissect, coagulate, elevate, or separate tissue. Ultrasonic instruments utilizing solid core technology are particularly advantageous because of the amount of ultrasonic energy that may be transmitted from the ultrasonic transducer, through an ultrasonic transmission waveguide, to the surgical end effector. Such instruments may be used for open procedures or minimally invasive procedures, such as endoscopic or laparoscopic procedures, wherein the end effector is passed through a trocar to reach the surgical site.

Activating or exciting the end effector (e.g., cutting blade, ball coagulator) of such instruments at ultrasonic frequencies induces longitudinal vibratory movement that generates localized heat within adjacent tissue, facilitating both cutting and coagulating. Because of the nature of ultrasonic instruments, a particular ultrasonically actuated end effector may be designed to perform numerous functions, including, for example, cutting and coagulating.

Ultrasonic vibration is induced in the surgical end effector by electrically exciting a transducer, for example. The transducer may be constructed of one or more piezoelectric or magnetostrictive elements in the instrument hand piece. Vibrations generated by the transducer section are transmitted to the surgical end effector via an ultrasonic waveguide extending from the transducer section to the surgical end effector. The waveguides and end effectors are designed to resonate at the same frequency as the transducer. When an end effector is attached to a transducer the overall system frequency may be the same frequency as the transducer itself.

The transducer and the end effector may be designed to resonate at two different frequencies and when joined or coupled may resonate at a third frequency. The zero-to-peak amplitude of the longitudinal ultrasonic vibration at the tip, d, of the end effector behaves as a simple sinusoid at the resonant frequency as given by:

$$d=A\sin(\omega t)$$

where:

$\omega$=the radian frequency which equals $2\pi$ times the cyclic frequency, f; and A=the zero-to-peak amplitude.

The longitudinal excursion is defined as the peak-to-peak (p-t-p) amplitude, which is just twice the amplitude of the sine wave or 2 A.

Solid core ultrasonic surgical instruments may be divided into two types, single element end effector devices and multiple-element end effectors. Single element end effector devices include a variety of blade types such as ball, hooked, curved, and coagulating shears. Single-element end effector instruments have limited ability to apply blade-to-tissue pressure when the tissue is soft and loosely supported. Substantial pressure may be necessary to effectively couple ultrasonic energy to the tissue. The inability of a single-element end effector to grasp the tissue results in a further inability to fully coapt tissue surfaces while applying ultrasonic energy, leading to less-than-desired hemostasis and tissue joining. Multiple-element end effectors include a clamping mechanism that works in conjunction with the vibrating blade. Ultrasonic clamping coagulators provide an improved ultrasonic surgical instrument for cutting/coagulating tissue, particularly loose and unsupported tissue. The clamping mechanism presses the tissue against the vibrating ultrasonic blade and applies a compressive or biasing force against the tissue to achieve faster cutting and hemostatis (e.g., coagulation) of the tissue with less attenuation of blade motion.

Tissue welding is a technique for closing wounds and vessels and is applied in many surgical specialties. Tissue welding is a technique for closing wounds by creating a hemostatic seal in the wounds or vessels as well as creating strong anastomoses in the tissue. Ultrasonic surgical instruments may be employed to achieve hemostatis with minimal lateral thermal damage to the tissue. The hemostatis or anastomoses occurs through the transfer of mechanical energy to the tissue. Internal cellular friction breaks hydrogen bonds resulting in protein denaturization. As the proteins are denatured, a sticky coagulum forms and seals small vessels at temperatures below 100° C. Anastomoses occurs when the effects are prolonged. Thus, the ultrasonic energy in the vibrating blade may be employed to create hemostatic seals in vessels and adjacent tissues in wounds and to create strong anastomoses in tissue. Ultrasonic vibrating single or multiple end effectors, either alone or in combination with clamping mechanisms, produce adequate mechanical energy to seal vessels regardless of the temperature of the end effector and/or the tissue. To create strong anastomoses of the tissue, the temperature of the end effector and the tissue should be maintained below approximately 50° C. to allow for the creation of a coagulum to seal the tissues together without desiccating the tissues. Desiccation occurs through the cavitational effect. As the blade vibrates, it produces an area of transient low pressure at the tip of the blade causing fluid inside the cells to vaporize and rupture. Ultrasonic devices have not been successfully employed in tissue welding applications because of the need to control the temperature of the end effector and the tissue to achieve suitable hemostatis and anastomoses to weld tissue together. As the temperature of the end effector increases with use, there exists the likelihood that the tissues will desiccate without forming a proper seal. Conventional ultrasonic instruments ascertain the tissue state of desiccation as a feedback mechanism to address temperature control of the ultrasonic end effector. These instruments, however, do not employ the temperature of the end effector as a feedback mechanism. Therefore, there is a need in the art to monitor and control the temperature of an ultrasonic end effector to effectively enable the welding of tissues in wounds and/or vessels.

Ultrasonic end effectors are known to build up heat with use. The heat build up may be greater when the blade is used in a shears system with high coaptation forces. Coaptation in the context of ultrasonic surgical instruments refers to the joining together or fitting of two surfaces, such as the edges of a wound, tissue and/or vessel. Standard methodologies of cooling the end effector blade, such as running fluid through the blade while cutting, can have the undesirable effect of reducing the cutting and coagulating effectiveness of the blade. Thus, there is a need for an ultrasonic end effector blade that is capable of generating adequate heat for hemostatis, coagulation, and/or anastomoses tissue but that quickly cools when it is not in use.

SUMMARY

In one general aspect, the various embodiments are directed to a surgical instrument, comprising a transducer configured to produce vibrations at a predetermined frequency. An ultrasonic end effector extends along a longitudinal axis and is coupled to the transducer. A controller is to receive a feedback signal from the ultrasonic end effector. A lumen is adapted to couple to a pump. The lumen is to conduct a fluid therethrough based on the feedback signal.

FIGURES

The novel features of the various embodiments are set forth with particularity in the appended claims. The various embodiments, however, both as to organization and methods of operation, may best be understood by reference to the following description, taken in conjunction with the accompanying drawings as follows.

DESCRIPTION

Figure 1:
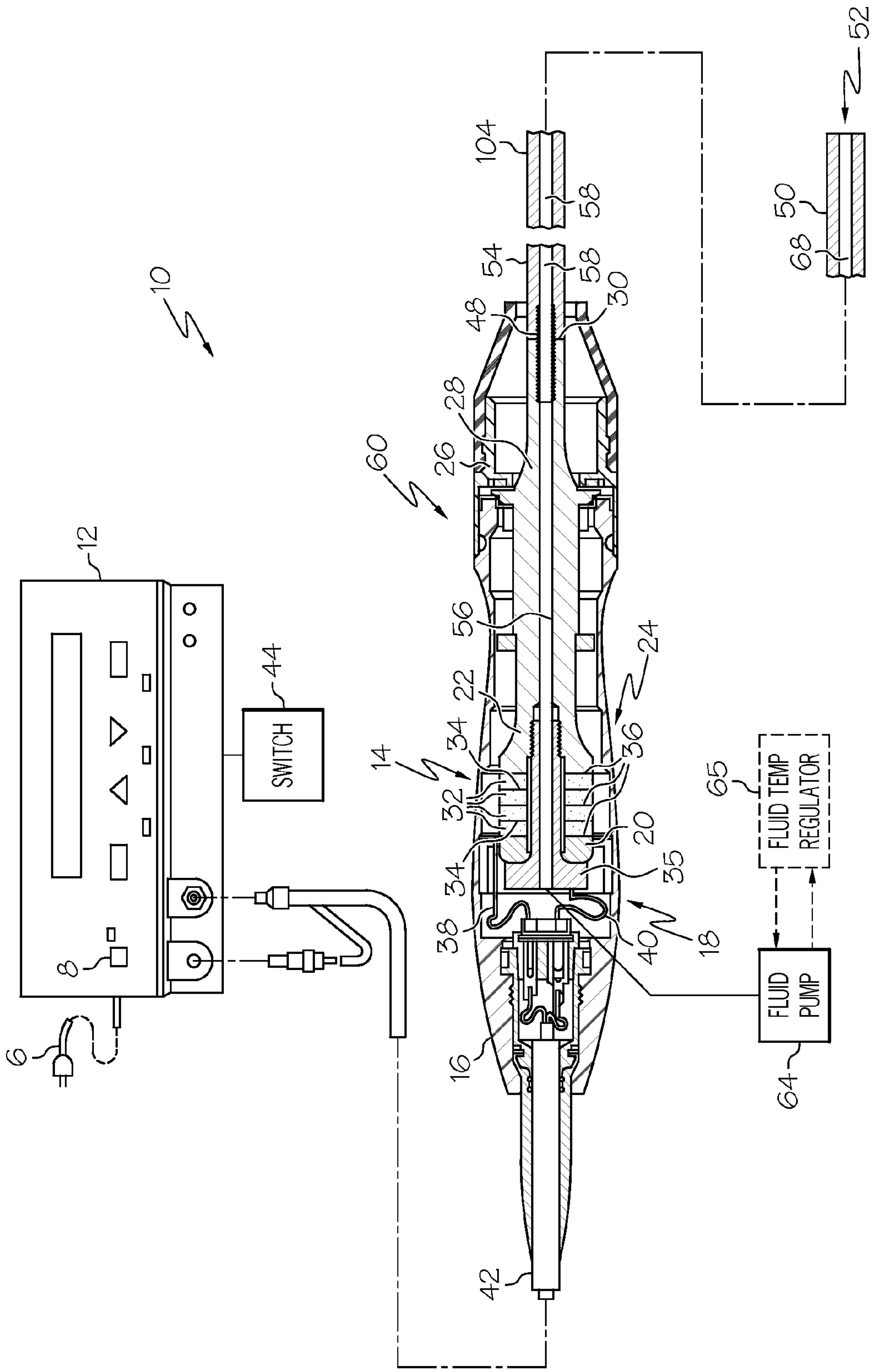
FIG. 1 illustrates one embodiment of an ultrasonic instrument comprising a single element end effector.

Before explaining the various embodiments in detail, it should be noted that the embodiments are not limited in its application or use to the details of construction and arrangement of parts illustrated in the accompanying drawings and description. The illustrative embodiments may be implemented or incorporated in other embodiments, variations and modifications, and may be practiced or carried out in various ways. For example, the surgical instruments and end effector configurations disclosed below are illustrative only and not meant to limit the scope or application thereof. Furthermore, unless otherwise indicated, the terms and expressions employed herein have been chosen for the purpose of describing the illustrative embodiments for the convenience of the reader and are not to limit the scope thereof.

The various embodiments relate, in general, to ultrasonic instruments with improved thermal characteristics. In one embodiment, the ultrasonic instruments provide end effectors with reduced heat build during use. The embodiments include, for example, blades used in a shears system with high coaptation forces where the heat build up may be greater. Coaptation in the context of ultrasonic surgical instruments refers to the joining together or fitting of two surfaces, such as the edges of a wound, tissue and/or vessel. The end effector may be cooled by running fluid through the end effector after cutting tissue when not in use. One embodiment provides an ultrasonic blade that is capable of generating adequate heat for hemostatis, coagulation, and/or anastomoses tissue but that quickly cools when it is not in use.

In various other embodiments the ultrasonic instruments with improved thermal characteristics provide improved tissue welding techniques for closing wounds and vessels as may be applied in many surgical specialties. Tissue welding is a technique for closing wounds by creating a hemostatic seal in the wounds or vessels as well as creating strong anastomoses in the tissue. Various embodiments of ultrasonic surgical instruments provide hemostatis with minimal lateral thermal damage to the tissue. The hemostatis or anastomoses occurs through the transfer of mechanical energy to the tissue. Internal cellular friction breaks hydrogen bonds resulting in protein denaturization. As the proteins are denatured, a sticky coagulum forms and seals small vessels at temperatures below 100° Celsius. Anastomoses occurs when the effects are prolonged. Thus, in various embodiments, the ultrasonic energy in the vibrating end effector may be employed to create hemostatic seals in vessels and adjacent tissues in wounds and to create strong anastomoses in tissue. Other embodiments provide ultrasonic vibrating single or multiple end effectors, either alone or in combination with clamping mechanisms, to produce suitable mechanical energy to seal vessels with controlled temperature end effectors. To create strong anastomoses of the tissue, the temperature of the end effector and the tissue should be maintained or regulated at or below approximately 50° C. to allow for the creation of a coagulum to seal the tissues together without desiccating the tissues. Desiccation occurs through the cavitational effect. As the end effector vibrates, it produces an area of transient low pressure at the tip of the end effector causing fluid inside the cells to vaporize and rupture. Various embodiments of controlled temperature ultrasonic devices may be employed in tissue welding applications because the temperature of the end effector is effectively controlled to achieve suitable hemostatis and anastomoses to weld tissue together. As the temperature of the end effector increases with use, the ultrasonic blade and/or clamping mechanism there is measured and cooling fluid is pumped through the blade and/or clamping mechanism. Various embodiments of the ultrasonic instruments ascertain the tissue state of desiccation as a feedback mechanism to address temperature control of the ultrasonic end effector. These instruments, employ the temperature of the end effector as a feedback mechanism to monitor and control the temperature of an ultrasonic end effector to effectively enable the welding of tissues in wounds and/or vessels.

Examples of ultrasonic surgical instruments are disclosed in U.S. Pat. Nos. 5,322,055 and 5,954,736 and in combination with ultrasonic end effectors and surgical instruments disclosed in U.S. Pat. Nos. 6,309,400 B2, 6,278,218 B1, 6,283, 981 B1, and 6,325,811 B1, for example, are incorporated herein by reference in their entirety. These references disclose ultrasonic surgical instruments and end effector configurations where a longitudinal mode of the end effector is excited. Because of asymmetry or asymmetries, ultrasonic end effectors also may exhibit transverse and/or torsional motion where the characteristic "wavelength" of this non-longitudinal motion is less than that of the general longitudinal motion of the end effector and its extender portion. Therefore, the wave shape of the non-longitudinal motion will present nodal positions of transverse/torsional motion along the tissue effector while the net motion of the active end effector along its tissue effector is non-zero (i.e., will have at least longitudinal motion along the length extending from its distal end, an antinode of longitudinal motion, to the first nodal position of longitudinal motion that is proximal to the tissue effector portion).

Certain embodiments will now be described to provide an overall understanding of the principles of the structure, function, manufacture, and use of the devices and methods disclosed herein. One or more examples of these embodiments are illustrated in the accompanying—drawings. Those of ordinary skill in the art will understand that the devices and methods specifically described herein and illustrated in the accompanying drawings are non-limiting embodiments and that the scope of the various embodiments is defined solely by the claims. The features illustrated or described in connection with one embodiment may be combined with the features of other embodiments. Such modifications and variations are intended to be included within the scope of the claims.

In one embodiment, the temperature of an ultrasonic end effector may be approximately determined while in use by measuring the resonant frequency of the ultrasonic system and correlating variations in the end effector frequency with the end effector temperature. For example, as the temperature of the end effector increases, the frequency drops. The correlation between frequency shift or drift due to temperature variations may be determined empirically by experimentation or design parameters and programmed into the ultrasonic signal generator or in an electronic controller coupled to the ultrasonic instrument and/or the generator. In one embodiment, a technique measures the frequency of the ultrasonic system and utilizes this information to adjust the flow of fluid into the surgical area to adjust the temperature of the end effectors. In another embodiment, the temperature of the end effector may be determined directly with a temperature sensor. The temperature of the end effector may be measured with thermocouple, acoustic sensor, or thermistor type devices embedded within the end effector or the instrument sheath, allowing a correlation to be made with the temperature of the end effector. Once the temperature of the end effector is determined, the end effector may be cooled by flowing lower temperature fluid on the ultrasonic end effector, through the ultrasonic end effector, or surrounding tissue, keeping them at a predetermined temperature.

In various embodiments, the ultrasonic end effector or clamping mechanism may be formed with internal lumens or cannulas such that fluid may be flowed through the end effector or clamping mechanism at a suitable flow rate necessary to maintain or regulate the end effector at a predetermined temperature. In another embodiment, the fluid may be heated to a predetermined temperature and then flowed through the lumens at a suitable flow rate to transfer heat to the tissue to assist in coagulation or tissue welding.

In another embodiment, a phase change material may be provided in the lumen. The phase change material changes from a solid or liquid phase to a gaseous phase and may be located inside the end effector lumens to control the temperature of the end effector. Expansion of the phase change material from a solid or liquid phase to a gaseous phase absorbs heat and keeps the end effector at a specified temperature. In yet another embodiment, the phase change material may act like a heat pipe material, absorbing heat at the end effector/tissue interface and releasing the heat away from the interface.

A strong coagulation area, as may be needed in larger lumen tissue welding applications, may be achieved by maintaining the temperature of the end effector surface at a point between where coagulation of the tissue can occur but where desiccation of the tissue does not occur. Lowering the temperature of the ultrasonic end effector enables the end effector to contact the tissue for a longer period. This allows for both the side of the tissue in contact with the end effector and the side in contact with the coaptation pad to form viable coagulation zones, thus improving the weld strength of the tissue. In another embodiment, the same end effector cooling fluid may be routed through a coaptation pad to increase the temperature of the tissue on the side opposing the end effector.

Thus, in one embodiment, the temperature of the ultrasonic end effector may be controlled by employing end effector temperature measurement as a feedback mechanism and infusing water or another cooling fluid into the end effector to maintain or control the temperature of the end effector. Infusing water at a specified temperature keeps the end effector at that temperature and absorbs excess energy from the system that would otherwise desiccate the tissue. The end effector temperature may be measured using frequency change of the system or by direct measurement of the end effector sheath temperature. End effector temperature may be controlled by infusing a cooling fluid through the end effector. The cooling fluid may be employed to cool the ultrasonic end effector and to heat the coaptation pad side of the instrument.

Irrigation lumens formed within the body of an ultrasonic end effector have been employed in ultrasonic aspirators such as ultrasonic surgical aspirators (CUSA®) produced by CAVITRON®, for example. The lumens act as fluidic conduits to provide relatively constant irrigation to the target site. In one embodiment, a end effector irrigation lumen may be fluidically coupled to an irrigation pump that is programmed for intermittent activation. The ultrasonic end effector may be used for tissue cutting and/or hemostasis (e.g., coagulation). During this process, the pump remains in a no-flow condition. Once the tissue load is removed from the end effector, the ultrasonic signal generator or controller senses the no tissue load condition and then operates the pump either continuously or intermittently to supply cooling fluid to the end effector for a specified amount of time or until the end effector reaches a predetermined temperature. In one embodiment, the ultrasonic signal generator or a controller may be adapted and configured to sense the end effector temperature by a referred measurement of system frequency and fluid may be supplied to the end effector until the end effector reaches a predetermined temperature.

In another embodiment, the ultrasonic signal generator or a controller may be adapted and configured to control the supply of fluid to the end effector for a specified amount of time after the user discontinues using the end effector. This embodiment in combination with the temperature measuring embodiment may be employed to cool the end effector to a specified temperature. In yet another embodiment, a cooling fluid may be fed or supplied either from a lumen formed within the end effector sheath or from a fluid flow port attached to the sheath. Either of these methods would be suitable for spraying fluid over the exterior of the end effector to control the temperature thereof.

FIG. 1 illustrates one embodiment of an ultrasonic instrument 10 comprising a single element end effector. One embodiment of the ultrasonic instrument 10 comprises an ultrasonic transducer 14, a hand piece assembly 60 comprising a hand piece housing 16, and an ultrasonically actuatable single element end effector or ultrasonically actuatable end effector 50. The end effector 50 may be, for example, a blade, ball coagulator, graspers, cutters, staplers, clip appliers, access devices, drug/gene therapy devices, ultrasound, microwave, RF, High Intensity Focused Ultrasound (HIFU), and/or laser devices. The ultrasonic instrument 10 is coupled to an ultrasonic signal generator 12. The generator 12 comprises a control system integral with the generator 12, a power switch 8, and a triggering mechanism 44. The power switch 8 controls the electrical power to the generator 12, and when activated by the triggering mechanism 44, the generator 12 provides energy to drive an acoustic assembly 24 of the surgical system 10 at a predetermined frequency and to drive the end effector 50 at a predetermined excursion level. The generator 12 drives or excites the acoustic assembly 24 at any suitable resonant frequency of the acoustic assembly 24. The ultrasonic transducer 14, which is known as a "Langevin stack", generally includes a transduction portion 18, a first resonator portion or end-bell 20, and a second resonator portion or fore-bell 22, and ancillary components. The total construction of these components is a resonator. The ultrasonic transducer 14 is preferably an integral number of one-half wavelengths (nλ/2 where "n" is any positive integer, e.g., n=1, 2, 3 . . . ; and where the wavelength "λ" is the wavelength of a pre-selected or operating longitudinal vibration frequency $f_o$ of the acoustic assembly) in length as will be described in more detail later. The acoustic assembly 24 includes the ultrasonic transducer 14, an adapter 26, a velocity transformer 28, and a surface 30. In various embodiments, the transducer 14 may be constructed of one or more piezoelectric or magnetostrictive elements.

It will be appreciated that the terms "proximal" and "distal" are used herein with reference to a clinician gripping the hand piece assembly 60. Thus, the end effector 50 is distal with respect to the more proximal hand piece assembly 60. It will be further appreciated that, for convenience and clarity, spatial terms such as "top" and "bottom" also are used herein with respect to the clinician gripping the hand piece assembly 60. However, surgical instruments are used in many orientations and positions, and these terms are not intended to be limiting and absolute.

The distal end of the end-bell 20 is connected to the proximal end of the transduction portion 18, and the proximal end of the fore-bell 22 is connected to the distal end of the transduction portion 18. The fore-bell 22 and the end-bell 20 have a length determined by a number of variables, including the thickness of the transduction portion 18, the density and modulus of elasticity of the material used to manufacture the end-bell 20 and the fore-bell 22, and the resonant frequency of the ultrasonic transducer 14. The fore-bell 22 may be tapered inwardly from its proximal end to its distal end to amplify the ultrasonic vibration amplitude as the velocity transformer 28, or alternately may have no amplification. A suitable vibrational frequency range may be about 20 Hz to 120 kHz and a well-suited vibrational frequency range may be about 30-100 kHz. A suitable operational vibrational frequency may be approximately 55.5 kHz, for example.

Piezoelectric elements 32 may be fabricated from any suitable material, such as, for example, lead zirconate-titanate, lead meta-niobate, lead titanate, barium titanate, or other piezoelectric ceramic material. Each of positive electrodes 34, negative electrodes 36, and the piezoelectric elements 32 has a bore extending through the center. The positive and negative electrodes 34 and 36 are electrically coupled to wires 38 and 40, respectively. The wires 38 and 40 are encased within a cable 42 and electrically connectable to the ultrasonic signal generator 12 of the ultrasonic instrument 10.

The generator 12 also has a power line 6 for insertion in an electro-surgical unit or conventional electrical outlet. It is contemplated that the generator 12 also can be powered by a direct current (DC) source, such as a battery. The generator 12 may comprise any suitable generator. The ultrasonic transducer 14 of the acoustic assembly 24 converts the electrical signal from the ultrasonic signal generator 12 into mechanical energy that results in primarily a standing wave of longitudinal vibratory motion of the ultrasonic transducer 24 and the end effector 50 at ultrasonic frequencies. In another embodiment, the vibratory motion of the ultrasonic transducer may act in a different direction. For example, the vibratory motion may comprise a local longitudinal component of a more complicated motion of the tip of the ultrasonic instrument 10. A suitable generator is available as model number GEN04, from Ethicon Endo-Surgery, Inc., Cincinnati, Ohio. When the acoustic assembly 24 is energized, a vibratory motion standing wave is generated through the acoustic assembly 24. The amplitude of the vibratory motion at any point along the acoustic assembly 24 depends upon the location along the acoustic assembly 24 at which the vibratory motion is measured. A minimum or zero crossing in the vibratory motion standing wave is generally referred to as a node (i.e., where motion is minimal), and an absolute value maximum or peak in the standing wave is generally referred to as an anti-node (i.e., where motion is maximal). The distance between an anti-node and its nearest node is one-quarter wavelength (λ/4).

The wires 38 and 40 transmit an electrical signal from the ultrasonic signal generator 12 to the positive electrodes 34 and the negative electrodes 36. The piezoelectric elements 32 are energized by the electrical signal supplied from the ultrasonic signal generator 12 in response to an actuator or triggering mechanism 44, such as a foot switch, for example, to produce an acoustic standing wave in the acoustic assembly 24. The electrical signal causes disturbances in the piezoelectric elements 32 in the form of repeated small displacements resulting in large alternating compression and tension forces within the material. The repeated small displacements cause the piezoelectric elements 32 to expand and contract in a continuous manner along the axis of the voltage gradient, producing longitudinal waves of ultrasonic energy. The ultrasonic energy is transmitted through the acoustic assembly 24 to the single element end effector 50, such as the blade, via a transmission component or an ultrasonic transmission waveguide 104.

For the acoustic assembly 24 to deliver energy to the single element end effector 50, all components of the acoustic assembly 24 must be acoustically coupled to the end effector 50. The distal end of the ultrasonic transducer 14 may be acoustically coupled at the surface 30 to the proximal end of the ultrasonic transmission waveguide 104 by a threaded connection such as a cannulated threaded stud 48.

The components of the acoustic assembly 24 are preferably acoustically tuned such that the length of any assembly is an integral number of one-half wavelengths (nλ/2), where the wavelength λ is the wavelength of a pre-selected or operating longitudinal vibration drive frequency $f_d$ of the acoustic assembly 24, and where n is any positive integer. It is also contemplated that the acoustic assembly 24 may incorporate any suitable arrangement of acoustic elements.

The length of the end effector 50 may be substantially equal to an integral multiple of one-half wavelengths (nλ/2). A distal end 52 of the end effector 50 may be disposed near an antinode in order to provide the maximum longitudinal excursion of the distal end 52. When the transducer assembly is energized, the distal end 52 of the end effector 50 may be configured to move in the range of, for example, approximately 10 to 500 microns peak-to-peak, and preferably in the range of about 30 to 150 microns at a predetermined vibrational frequency of 55 kHz, for example.

The end effector 50 may comprise an inner lumen 68 extending longitudinally to receive and conduct fluid to a target site. The target site may be the cutting, coagulating, or tissue welding site, for example. The lumen 68 is in fluid communication with (e.g., is fluidically coupled to) a fluid pump 64. In various embodiments, the fluid pump 64 and the ultrasonic signal generator 12 may be combined in a single integral unit. In the embodiment, illustrated in FIG. 1, the ultrasonic transmission waveguide 104 comprises a longitudinally extending lumen 58 formed therein and the ultrasonic transducer 14 comprises a lumen 56 formed through the fore bell 20, the end bell 22, the velocity transformer 28, and the coupling stud or bolt 35. The bolt 35 also comprises a lumen 55 substantially aligned with the lumen 56. The ultrasonic transmission waveguide 104 comprises a longitudinally projecting attachment post 54 at a proximal end to couple to the surface 30 of the ultrasonic transmission waveguide 104 by a cannulated threaded connection such as the cannulated threaded stud 48. The ultrasonic transmission waveguide 104 is coupled to the velocity transformer 28 portion of the ultrasonic transducer 14 by the cannulated threaded stud 48. The fluid pump 64 is fluidically coupled to the lumens 56, 58, and 68 such that fluid is communicated from the fluid pump 64 to the end effector 50 and it emanates into the target site from the distal end 52 of the end effector 50. In one embodiment, the fluid may be heated or cooled to a predetermined temperature by a fluid temperature regulator 65 (e.g., a heater, a chiller, a temperature bath, or any of various mechanisms for maintaining a temperature) before it is pumped into the lumens 56, 58, and 68 by the fluid pump 64.

The piezoelectric elements 32 may be held in compression between the first and second resonators 20 and 22 by the bolt 35. The bolt 35 may have a head, a shank, and a threaded distal end. The bolt 35 may be inserted from the proximal end of the first resonator 92 through the bores of the first resonator 20, the electrodes 34 and 36, and the piezoelectric elements 32. The threaded distal end of the bolt 35 is screwed into a threaded bore in the proximal end of second resonator 22. The bolt 35 can be fabricated from steel, titanium, aluminum, or other suitable material. IN various embodiments, the bolt 35 may be fabricated from Ti6Al4V Titanium, Ti 6-4 Titanium, and most preferably from 4037 low alloy steel.

The end effector 50 may be coupled to the ultrasonic transmission waveguide 104. The end effector 50 and the ultrasonic transmission waveguide 104 as illustrated are formed as a single unit construction from a material suitable for transmission of ultrasonic energy. Examples of such materials include Ti6Al4V (an alloy of Titanium including Aluminum and Vanadium), Aluminum, Stainless Steel, or other suitable materials. Alternately, the end effector 50 may be separable (and of differing composition) from the ultrasonic transmission waveguide 104, and coupled by, for example, a stud, weld, glue, quick connect, or other suitable known methods. The length of the ultrasonic transmission waveguide 104 may be substantially equal to an integral number of one-half wavelengths (nλ/2), for example. The ultrasonic transmission waveguide 104 may be preferably fabricated from a solid core shaft constructed out of material suitable to propagate ultrasonic energy efficiently, such as the titanium alloy discussed above (i.e., Ti6Al4V) or any suitable aluminum alloy, or other alloys, for example.

In one embodiment, the ultrasonic transmission waveguide 104 includes a plurality of stabilizing silicone rings or compliant supports positioned at a plurality of nodes (not shown). The silicone rings dampen undesirable vibration and isolate the ultrasonic energy from an outer sheath (not shown) assuring the flow of ultrasonic energy in a longitudinal direction to the distal end 52 of the end effector 50 with maximum efficiency.

The outer sheath protects a user of the ultrasonic surgical instrument 10 and a patient from the ultrasonic vibrations of the ultrasonic transmission waveguide 104. The sheath generally includes a hub and an elongated tubular member. The tubular member is attached to the hub and has an opening extending longitudinally therethrough. The sheath is threaded onto the distal end of the housing 16. The ultrasonic transmission waveguide 104 extends through the opening of the tubular member and the silicone rings isolate the ultrasonic transmission waveguide 104 from the outer sheath. The outer sheath may be attached to the waveguide 104 with an isolator pin. The hole in the waveguide 104 may occur nominally at a displacement. The waveguide 104 may screw or snap onto the hand piece assembly 60 by the cannulated threaded stud 48. Flat portions on the hub may allow the assembly to be torqued to a required level.

The hub of the sheath is preferably constructed from plastic and the tubular member is fabricated from stainless steel.

Alternatively, the ultrasonic transmission waveguide 104 may comprise polymeric material surrounding it to isolate it from outside contact.

The distal end of the ultrasonic transmission waveguide 104 may be coupled to the proximal end of the end effector 50 by an internal cannulated threaded connection, preferably at or near an antinode. It is contemplated that the end effector 50 may be attached to the ultrasonic transmission waveguide 104 by any suitable means, such as a welded joint or the like. Although the end effector 50 may be detachable from the ultrasonic transmission waveguide 104, it is also contemplated that the single element end effector 50 (e.g., a blade) and the ultrasonic transmission waveguide 104 may be formed as a single unitary piece.

Figure 2:
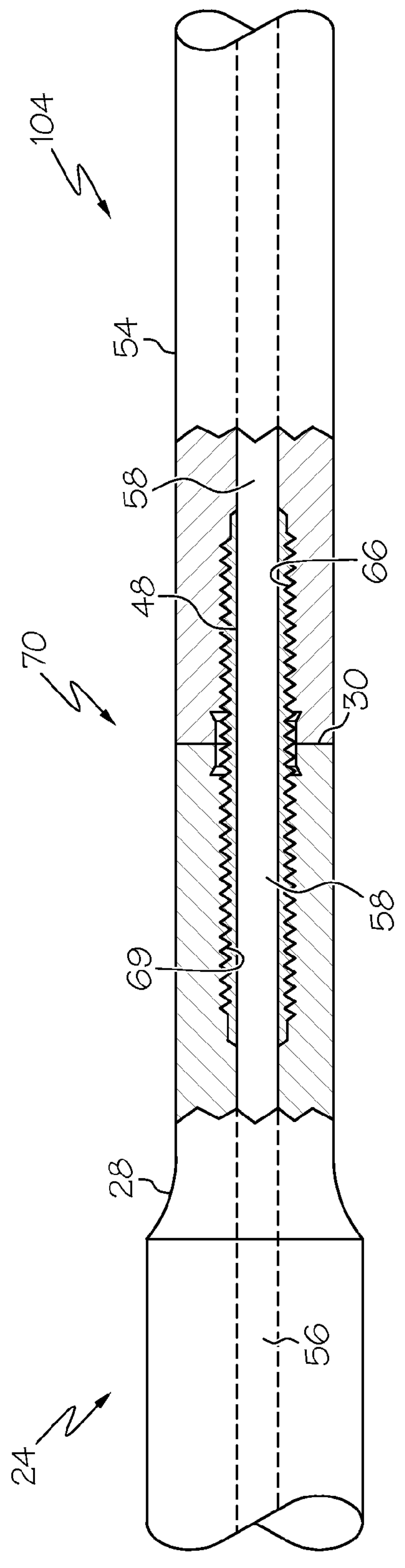
FIG. 2 illustrates one embodiment of a connection union/joint for an ultrasonic instrument.

FIG. 2 illustrates one embodiment of a connection union/joint 70 for an ultrasonic instrument. The connection union/joint 70 may be formed between the attachment post 54 of the ultrasonic transmission waveguide 104 and the surface 30 of the velocity transformer 28 at the distal end of the acoustic assembly 24. The proximal end of the attachment post 54 comprises a female threaded substantially cylindrical surface 66 to receive a portion of the cannulated threaded stud 48 therein. The distal end of the velocity transformer 28 also may comprise a female threaded substantially cylindrical surface 69 to receive a portion of the cannulated threaded stud 48. The surfaces 66, 69 are substantially circumferentially and longitudinally aligned. The lumens 56 and 58 are fluidically coupled to the fluid pump 64 at a proximal end and to the end effector 50 lumen 68 at a distal end (FIG. 1).

Figure 3:
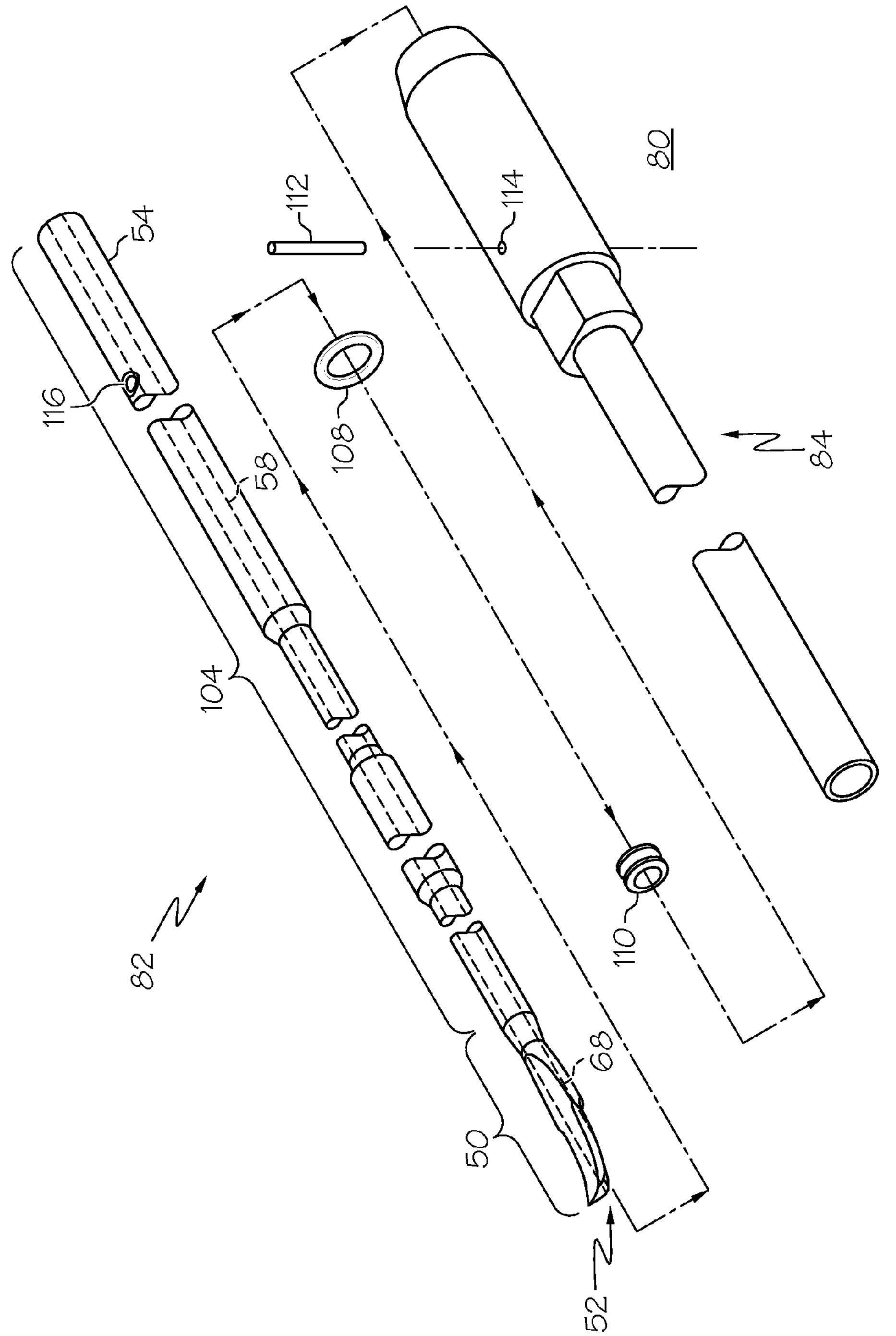
FIG. 3 illustrates an exploded perspective view of one embodiment of a sterile ultrasonic surgical instrument.

FIG. 3 illustrates an exploded perspective view of one embodiment of a sterile ultrasonic surgical instrument 80. The ultrasonic surgical instrument 80 may be employed in the above-described ultrasonic instrument 10. However, as described herein, those of ordinary skill in the art will understand that the various embodiments of the ultrasonic surgical instruments disclosed herein as well as any equivalent structures thereof could conceivably be effectively used in connection with other known ultrasonic surgical instruments without departing from the scope thereof. Thus, the protection afforded to the various ultrasonic surgical end effector embodiments disclosed herein should not be limited to use only in connection with the embodiments of the ultrasonic surgical instrument described above. The ultrasonic surgical instrument 80 may be sterilized by methods known in the art such as, for example, gamma radiation sterilization, Ethelyne Oxide processes, autoclaving, soaking in sterilization liquid, or other known processes.

In the embodiment illustrated in FIG. 3, the ultrasonic surgical instrument 80 comprises an ultrasonic transmission assembly 82. The ultrasonic transmission assembly 82 comprises the ultrasonically actuatable end effector 50, the ultrasonic transmission waveguide 104, the projecting attachment post 54, and an outer sheath 84. The ultrasonic transmission waveguide 104 comprises the longitudinally extending lumen 58 and the end effector comprises the longitudinally extending lumen 68. The end effector 50 and the ultrasonic transmission waveguide 104 may be formed as a unitary piece from a material suitable for transmission of ultrasonic energy such as, for example, Ti6Al4V (an alloy of Titanium including Aluminum and Vanadium), Aluminum, Stainless Steel, or other known materials. Alternately, the end effector 50 may be formed such that it is detachable or separable (and of differing composition) from the ultrasonic transmission waveguide 104, and coupled thereto by, a stud, weld, glue, quick connect, or other known methods, for example. In either implementation, the longitudinally extending lumens 58 and 68 are substantially aligned. The length of the ultrasonic transmission waveguide 104 may be substantially equal to an integral number of one-half wavelengths (nλ/2), for example. The ultrasonic transmission waveguide 104 may be fabricated from a solid core shaft constructed out of material that propagates ultrasonic energy efficiently, such as titanium alloy (i.e., Ti6Al4V) or an aluminum alloy, for example.

In the embodiment illustrated in FIG. 3, the ultrasonic transmission waveguide 104 is positioned in the outer sheath 84 by a mounting O-ring 108 and a sealing ring 110. One or more additional dampers or support members (not shown) also may be included along the ultrasonic transmission waveguide 104. The ultrasonic transmission waveguide 104 is affixed to the outer sheath 84 by the isolator pin 112 that passes through mounting holes 114 in the outer sheath 84 and a mounting hole 116 in the ultrasonic transmission waveguide 104.

Figure 4:
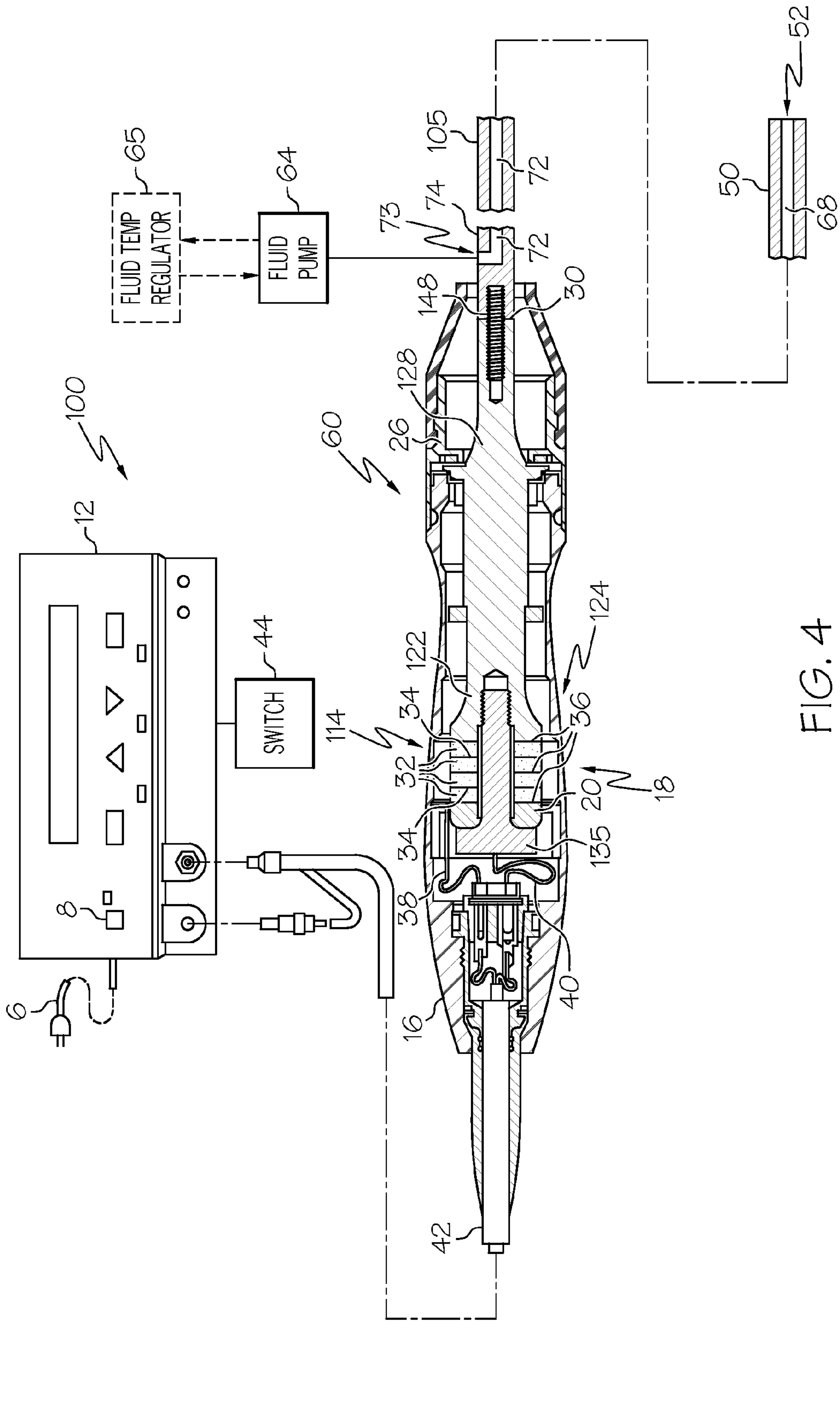
FIG. 4 illustrates one embodiment of an ultrasonic instrument comprising a single element end effector.

FIG. 4 illustrates one embodiment of an ultrasonic instrument 100 comprising a single element end effector. One embodiment of the ultrasonic instrument 100 comprises an ultrasonic transducer 114, the hand piece assembly 60 comprising the hand piece housing 16, and the ultrasonically actuatable single element end effector or ultrasonically actuatable end effector 50. The ultrasonic instrument 100 is coupled to the ultrasonic signal generator 12. The ultrasonic transducer 114, which is known as a "Langevin stack", generally includes a transduction portion 18, a first resonator portion or end-bell 20, and a second resonator portion or fore-bell 122, and ancillary components such as coupling stud or bolt 135, for example. The construction and operation of the bolt 135 is substantially similar to the bolt 35 discussed above except it is formed as a solid piece, without the central lumen 55. The total construction of these components is a resonator. The ultrasonic transducer 114 is preferably an integral number of one-half wavelengths (nλ/2) in length as will be described in more detail later. An acoustic assembly 124 includes the ultrasonic transducer 114, an adapter 26, a velocity transformer 128, and a surface 30. The operation of the ultrasonic transducer 114 is substantially similar to that described above with reference to FIG. 1 and for convenience and clarity is not repeated herein. In contrast to the ultrasonic transducer 14 shown in FIG. 1, the ultrasonic transducer 114 shown in FIG. 4 does not include lumens formed therein. Rather, as described in more detail below, an inlet port 73 may be formed in an attachment post 74 or along the ultrasonic transmission waveguide 105 that is fluidically coupled to a lumen 72 extending longitudinally within the attachment post 74 and an ultrasonic waveguide 105. The lumen 72 is fluidically coupled to the lumen 68 formed in the end effector 50. The lumen 72 may be substantially aligned with the lumen 68 formed in the end effector 50.

As previously described, the end effector 50 comprises an inner lumen 68 extending longitudinally to receive and transfer fluid to through the end effector 50 or to a target site. The target site may be the cutting, coagulating, or tissue welding site, for example. The lumen 68 is fluidically coupled to the fluid pump 64. In the embodiment, illustrated in FIG. 4, the ultrasonic transmission waveguide 105 comprises a lumen 72 formed longitudinally therein. The ultrasonic transmission waveguide 105 comprises a longitudinally projecting attachment post 74 at a proximal end to couple to the surface 30 of the ultrasonic transmission waveguide 105 by a threaded connection such as a threaded stud 148. The ultrasonic transmission waveguide 105 is coupled to the velocity transformer 128 portion of the ultrasonic transducer 114 by the threaded stud 148. The fluid pump 64 is fluidically coupled to the lumens 72 and 68 via the inlet port 73 formed in the attachment post 74 such that fluid is communicated from the fluid pump 64 to the end effector 50 and it emanates into the target site from the distal end 52 of the end effector 50. In one embodiment, the fluid may be heated by the fluid temperature regulator 65 before it is pumped into the lumens 72 and 68 by the fluid pump 64.

Figure 5:
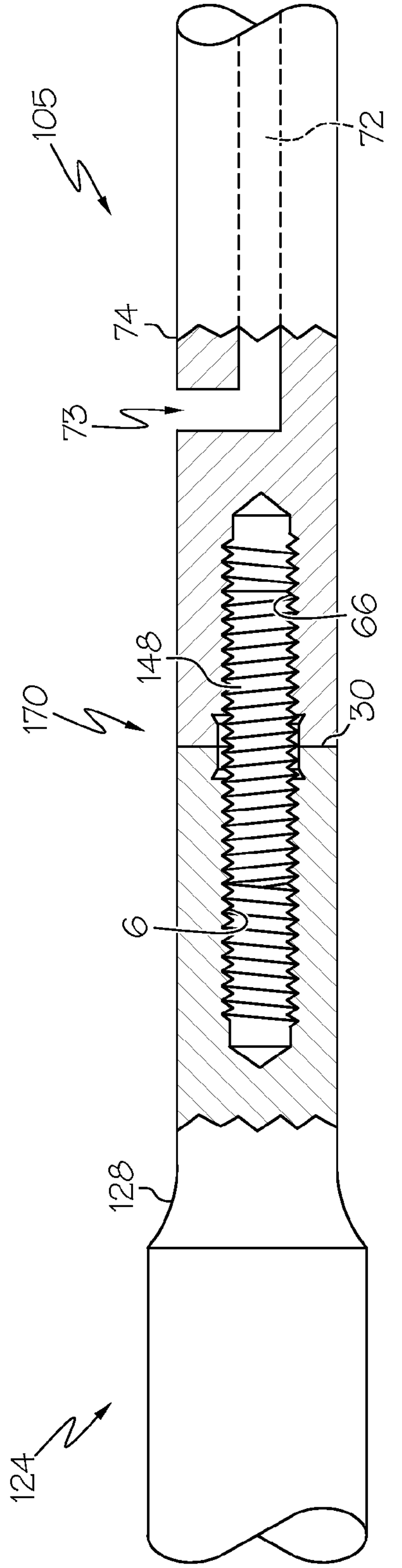
FIG. 5 illustrates one embodiment of a connection union/joint for an ultrasonic instrument.

FIG. 5 illustrates one embodiment of a connection union/joint 170 for an ultrasonic instrument. The connection union/joint 170 may be formed between the attachment post 74 of the ultrasonic transmission waveguide 105 and the surface 30 of the velocity transformer 128 at the distal end of the acoustic assembly 124. The proximal end of the attachment post 74 comprises a female threaded substantially cylindrical surface 66 to receive a portion of the threaded stud 148 therein. The distal end of the velocity transformer 128 also may comprise a female threaded substantially cylindrical surface 69 to receive a portion of the threaded stud 148. The surfaces 66, 69 are substantially circumferentially and longitudinally aligned. The lumen 72 is fluidically coupled to the fluid pump 64 via the inlet port 73 at a proximal end and is coupled to the end effector 50 lumen 68 at a distal end (FIG. 4).

Figure 6:
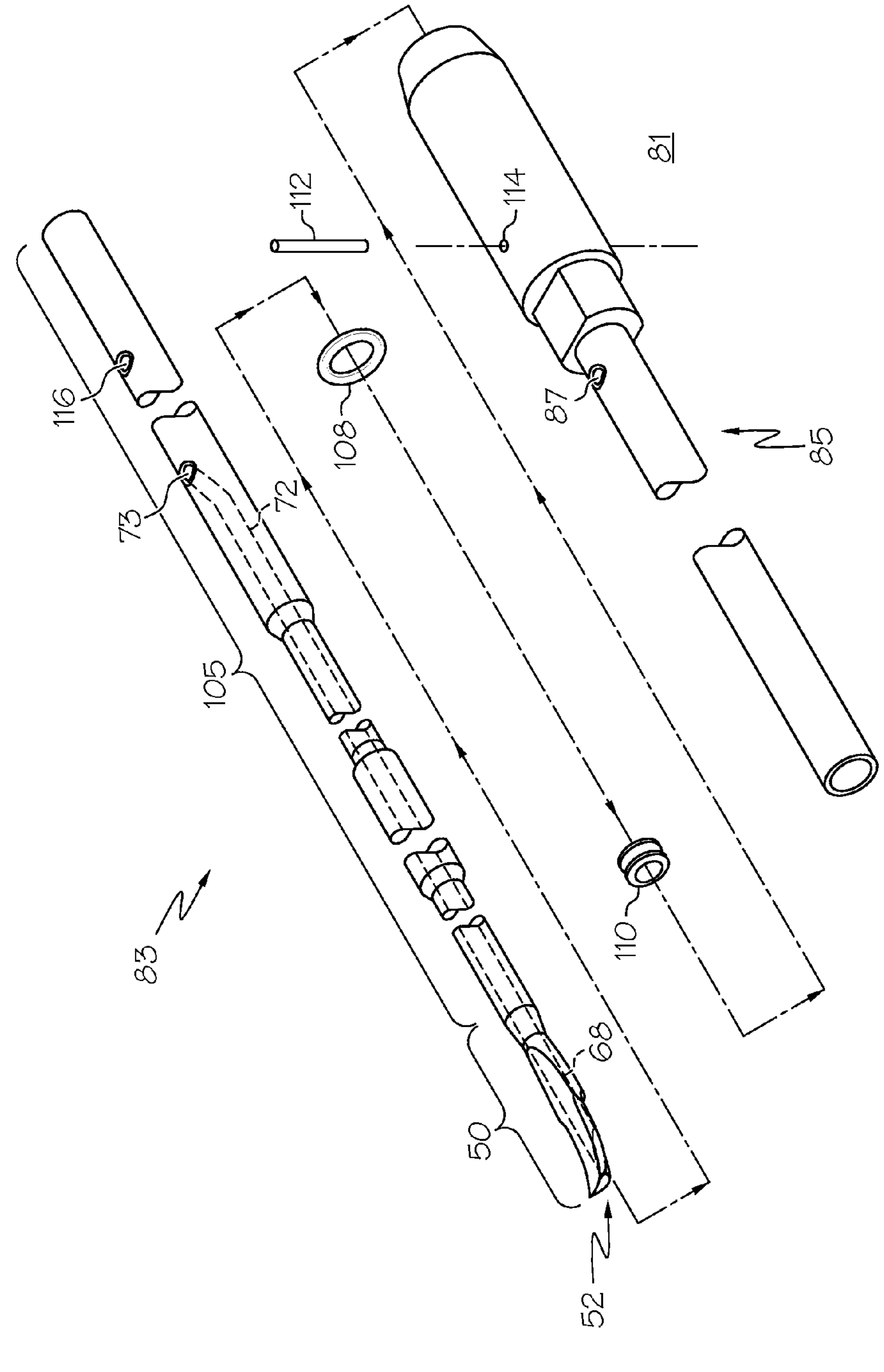
FIG. 6 illustrates an exploded perspective view of one embodiment of a sterile ultrasonic surgical instrument.

FIG. 6 illustrates an exploded perspective view of one embodiment of a sterile ultrasonic surgical instrument 81. The ultrasonic surgical instrument 81 may be employed in the above-described ultrasonic instrument 100. However, as described herein, those of ordinary skill in the art will understand that the various embodiments of the ultrasonic surgical instruments disclosed herein as well as any equivalent structures thereof could conceivably be effectively used in connection with other known ultrasonic surgical instruments without departing from the scope thereof. Thus, the protection afforded to the various ultrasonic surgical end effector embodiments disclosed herein should not be limited to use only in connection with the embodiments of the ultrasonic surgical instrument described above. The ultrasonic surgical instrument 81 may be sterilized by methods known in the art such as, for example, gamma radiation sterilization, Ethelyne Oxide processes, autoclaving, soaking in sterilization liquid, or other known processes.

In the embodiment illustrated in FIG. 6, the ultrasonic surgical instrument 81 comprises an ultrasonic transmission assembly 83. The ultrasonic transmission assembly 83 comprises the ultrasonically actuatable end effector 50, the ultrasonic transmission waveguide 105, the projecting attachment post 74, and an outer sheath 85. The ultrasonic transmission waveguide 105 comprises the longitudinally extending lumen 72 and the end effector comprises the longitudinally extending lumen 68. The sheath 85 comprises an opening 87 to receive a fluid line in the inlet port 73. The end effector 50 and the ultrasonic transmission waveguide 105 may be formed as a unitary piece from a material suitable for transmission of ultrasonic energy such as, for example, Ti6Al4V (an alloy of Titanium including Aluminum and Vanadium), Aluminum, Stainless Steel, or other known materials. Alternately, the end effector 50 may be formed such that it is detachable or separable (and of differing composition) from the ultrasonic transmission waveguide 105, and coupled thereto by, a stud, weld, glue, quick connect, or other known methods, for example. In either implementation, the longitudinally extending lumens 72 and 68 are substantially aligned. The length of the ultrasonic transmission waveguide 105 may be substantially equal to an integral number of one-half wavelengths ($n\lambda/2$), for example. The ultrasonic transmission waveguide 105 may be fabricated from a solid core shaft constructed out of material that propagates ultrasonic energy efficiently, such as titanium alloy (i.e., Ti6Al4V) or an aluminum alloy, for example.

In the embodiment illustrated in FIG. 6, the ultrasonic transmission waveguide 105 is positioned in the outer sheath 85 by a mounting O-ring 108 and a sealing ring 110. One or more additional dampers or support members (not shown) also may be included along the ultrasonic transmission waveguide 105. The ultrasonic transmission waveguide 105 is affixed to the outer sheath 85 by the isolator pin 112 that passes through mounting holes 114 in the outer sheath 85 and a mounting hole 116 in the ultrasonic transmission waveguide 104.

Figure 7A:
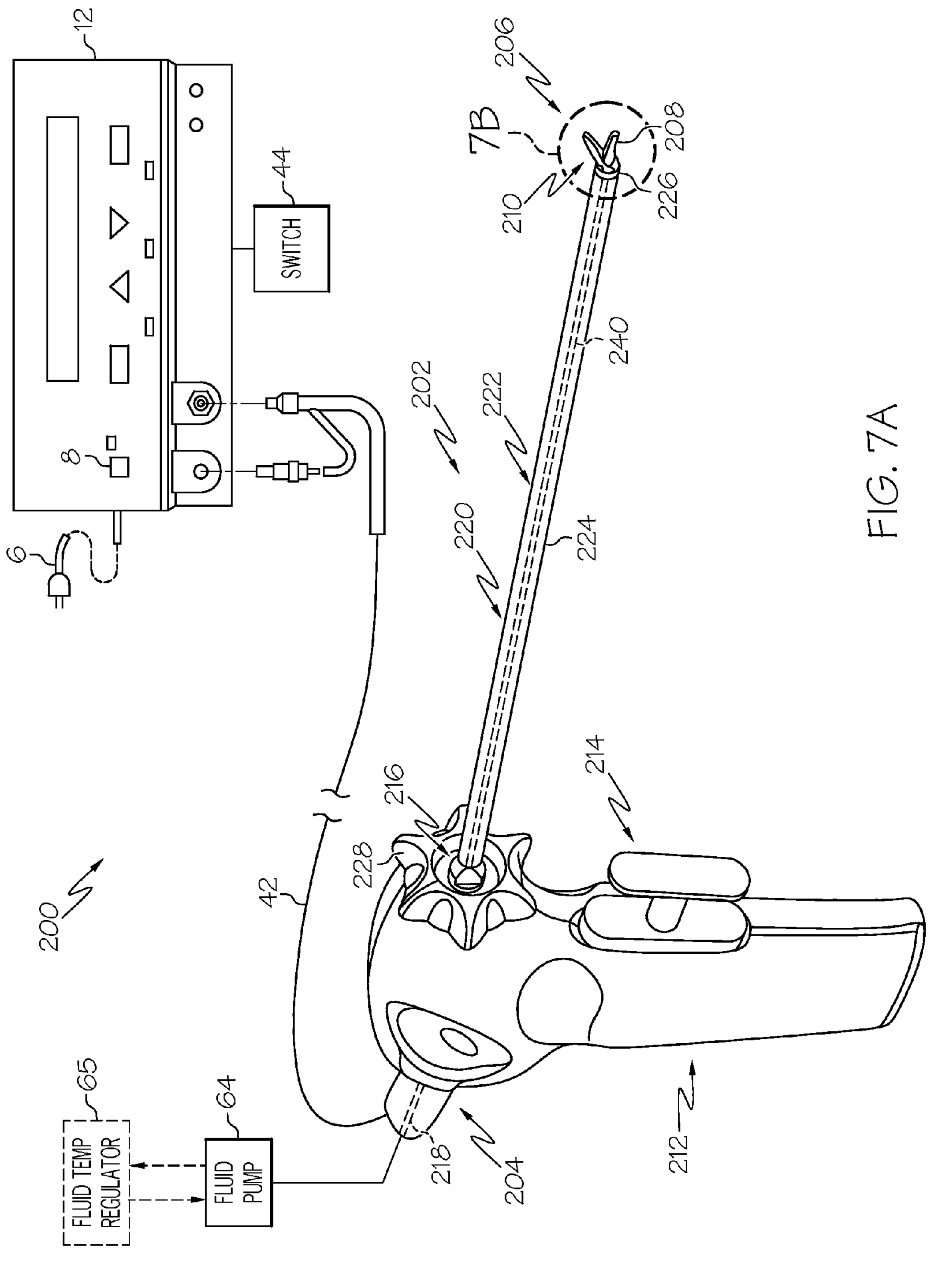
FIG. 7A illustrates one embodiment of a surgical system including a surgical instrument coupled to the ultrasonic generator.

FIG. 7A illustrates one embodiment of a surgical system 200 including a surgical instrument 202 coupled to the ultrasonic generator 12. In the embodiment illustrated in FIG. 7A, the ultrasonic surgical instrument 202 is an ultrasonic clamp coagulator. The surgical instrument 202 includes an ultrasonic drive unit 204. The ultrasonic drive unit 204 may comprise the ultrasonic transducer 14 (FIG. 1) or the ultrasonic transducer 114 (FIG. 4) based on the implementation. Therefore, for convenience and clarity, the description of the operation the ultrasonic drive unit 204 will not be repeated herein. The ultrasonic transducer of the ultrasonic drive unit 204 is coupled to an ultrasonic end effector 206 of the surgical instrument 202. Together these elements provide an acoustic assembly of the surgical system 200, with the acoustic assembly providing ultrasonic energy for surgical procedures when powered by the generator 12. It will be noted that, in some applications, the ultrasonic drive unit 204 may be referred to as a "hand piece assembly" because the surgical instrument 202 of the surgical system 200 is configured such that a clinician grasps and manipulates the ultrasonic drive unit 204 during various procedures and operations. The ultrasonic instrument 202 may comprise a scissors-like grip arrangement which facilitates positioning and manipulation of the instrument 202 apart from manipulation of the ultrasonic drive unit 204.

As previously discussed, the generator 12 of the surgical system 200 sends an electrical signal through a cable 42 at a selected excursion, frequency, and phase determined by a control system of the generator 12. As previously discussed, the signal causes one or more piezoelectric elements of the acoustic assembly of the surgical instrument 202 to expand and contract along a longitudinal axis, thereby converting the electrical energy into longitudinal mechanical motion. The mechanical motion results in longitudinal waves of ultrasonic energy that propagate through the acoustic assembly in an acoustic standing wave to vibrate the acoustic assembly at a selected frequency and excursion. The end effector 206 is placed in contact with tissue of the patient to transfer the ultrasonic energy to the tissue. For example, a distal portion or blade 208 of the end effector 206 may be placed in contact with the tissue. As further described below, a surgical tool, such as, a jaw or clamping mechanism 210, may be utilized to press the tissue against the blade 208.

As the end effector 206 couples to the tissue, thermal energy or heat is generated as a result of friction, acoustic absorption, and viscous losses within the tissue. The heat is sufficient to break protein hydrogen bonds, causing the highly structured protein (e.g., collagen and muscle protein) to denature (e.g., become less organized). As the proteins are denatured, a sticky coagulum forms to seal or coagulate small blood vessels. Deep coagulation of larger blood vessels results when the effect is prolonged.

The transfer of the ultrasonic energy to the tissue causes other effects including mechanical tearing, cutting, cavitation, cell disruption, and emulsification. The amount of cutting as well as the degree of coagulation obtained varies with the excursion of the end effector 206, the frequency of vibration, the amount of pressure applied by the user, the sharpness of the blade 208, and the coupling between the end effector 206 and the tissue.

As previously discussed, the generator 12 comprises a control system integral with the generator 12, a power switch 8, and a triggering mechanism 44. The power switch 8 controls the electrical power to the generator 12, and when activated by the triggering mechanism 44, the generator 12 provides energy to drive the acoustic assembly of the surgical system 200 at a predetermined frequency and to drive the end effector 206 at a predetermined excursion level. The generator 12 drives or excites the acoustic assembly at any suitable resonant frequency of the acoustic assembly.

When the generator 12 is activated via the triggering mechanism 44, electrical energy in the form of an electrical signal is continuously applied by the generator 12 to a transducer stack or assembly of the acoustic assembly 24 (FIG. 1) or 124 (FIG. 4) as previously discussed. A phase-locked loop in the control system of the generator 12 monitors feedback from the acoustic assembly. The phase lock loop adjusts the frequency of the electrical signal transmitted by the generator 12 to match of the acoustic assembly including the tissue load. In addition, a second feedback loop in the control system maintains the current amplitude of the electrical signal supplied to the acoustic assembly at a pre-selected constant level in order to achieve substantially constant excursion at the end effector 206 of the acoustic assembly. Tissue load can be detected and provided as a feedback signal indicative of an operational state of the ultrasonic blade 208.

The electrical signal supplied to the acoustic assembly will cause the distal end of the end effector 206, e.g., the blade 208, to vibrate longitudinally in the range of, for example, approximately 20 kHz to 250 kHz, and preferably in the range of about 54 kHz to 56 kHz, and most preferably at about 55.5 kHz. The excursion of the vibrations at the blade 208 can be controlled by, for example, controlling the amplitude of the electrical signal applied to the transducer assembly of the acoustic assembly by the generator 12.

As previously discussed, the triggering mechanism 44 of the generator 12 allows a user to activate the generator 12 so that electrical energy may be continuously supplied to the acoustic assembly. The triggering mechanism 44 may comprise a foot activated switch that is detachably coupled or attached to the generator 12 by a cable or cord. Alternatively, the triggering mechanism 44 can be configured as a hand switch incorporated in the ultrasonic drive unit 204 to allow the generator 12 to be activated by a user.

The generator 12 also has a power line 6 for insertion in an electro-surgical unit or conventional electrical outlet. It is contemplated that the generator 12 also can be powered by a direct current (DC) source, such as a battery. The generator 12 may comprise any suitable generator, such as Model No. GEN04 available from Ethicon Endo-Surgery, Inc.

The ultrasonic drive unit 204 of the surgical instrument 202 includes a multi-piece housing 212 adapted to isolate the operator from the vibrations of the acoustic assembly. The drive unit housing 212 can be shaped to be held by a user in a conventional manner, but it is contemplated that the clamp coagulator instrument ultrasonic instrument 202 is principally grasped and manipulated by a pistol-like arrangement 214 provided by a housing of the apparatus. While the multi-piece housing 212 is illustrated, the housing 212 may comprise a single or unitary component.

The ultrasonic drive unit 204 housing 212 generally comprises a proximal end, a distal end, and a cavity extending longitudinally therein. The distal end of the housing 212 includes an opening 216 configured to allow the acoustic assembly of the surgical system 200 to extend therethrough, and the proximal end of the housing 212 is coupled to the generator 12 by the cable 42. The cable 42 may include ducts, conduits, or lumens 218 to allow cooling fluid to be introduced to and to cool the end effector 206.

The housing 212 of the ultrasonic drive unit 204 may be constructed from a durable plastic, such as ULTEM®. It is also contemplated that the housing 212 may alternatively be made from a variety of materials including other plastics (e.g., liquid crystal polymer [LCP], nylon, or polycarbonate). A suitable ultrasonic drive unit 204 is Model No. HP054, available from Ethicon Endo-Surgery, Inc.

The acoustic assembly of the surgical instrument 200 generally includes a first acoustic portion and a second acoustic portion. The first acoustic portion may be carried by the ultrasonic drive unit 204, and the second acoustic portion in the form of an end effector 206 is carried by the ultrasonic clamp coagulator ultrasonic instrument 202. The distal end of the first acoustic portion is operatively coupled to the proximal end of the second acoustic portion, preferably by a threaded connection.

In the embodiment illustrated in FIG. 7A, the first acoustic portion comprises the transducer stack or assembly 14 (FIG. 1) or 114 (FIG. 4) and the respective velocity transformers 28, 128 and mounting surface 30, and the second acoustic portion includes the end effector 206. The end effector 206 may in turn comprise a transmission component, or waveguide 220, as well as a distal portion, or the blade 208, for interfacing with tissue. The waveguide 220 may be substantially similar to the waveguide 104 (FIGS. 1 and 2) or 105 (FIGS. 4 and 5).

As previously discussed, the components of the acoustic assembly may be acoustically tuned such that the length of each component is an integral number of one-half wavelengths ($n\lambda/2$). It is also contemplated that the acoustic assembly may incorporate any suitable arrangement of acoustic elements.

The transducer assembly of the acoustic assembly converts the electrical signal from the generator 12 into mechanical energy that results in longitudinal vibratory motion of the end effector 206 at ultrasonic frequencies. When the acoustic assembly is energized, a vibratory motion standing wave is generated through the acoustic assembly. The excursion of the vibratory motion at any point along the acoustic assembly depends on the location along the acoustic assembly at which the vibratory motion is measured. A minimum or zero crossing in the vibratory motion standing wave is generally referred to as a node (e.g., where motion is usually minimal), and an absolute value maximum or peak in the standing wave is generally referred to as an anti-node. The distance between an anti-node and its nearest node is one-quarter wavelength ($\lambda/4$).

As previously described with reference to FIGS. 1 and 4, the piezoelectric elements 32 may be energized in response to the electrical signal supplied from the generator 12 to produce an acoustic standing wave in the acoustic assembly 24, 124. The electrical signal causes an electromagnetic field across the piezoelectric elements 32, causing the piezoelectric elements 32 to expand and contract in a continuous manner along the longitudinal axis of the voltage gradient, producing high frequency longitudinal waves of ultrasonic energy. The ultrasonic energy is transmitted through the acoustic assembly 24, 124 to the end effector 206.

The mounting device 84 of the acoustic assembly has a proximal end, a distal end, and may have a length substantially equal to an integral number of one-half wavelengths ($n\lambda/2$). The proximal end of the mounting device 84 may be axially aligned and coupled to the distal end of the second resonator 94 by an internal threaded connection near an anti-node. It is also contemplated that the mounting device 84 may be attached to the second resonator 94 by any suitable means, and the second resonator 94 and mounting device 84 may be formed as a single or unitary component.

The proximal end of the clamp coagulator ultrasonic surgical instrument 202 preferably receives and is fitted to the distal end of the ultrasonic drive unit 204 by insertion of the drive unit 204 into the housing 212. The clamp coagulator ultrasonic surgical instrument 202 may be attached to and removed from the ultrasonic drive unit 204 as a unit. The clamp coagulator ultrasonic surgical instrument 202 may be disposed of after a single use.

The clamp coagulator ultrasonic surgical instrument 202 may comprise an elongated or endoscopic portion 222. When the present apparatus is configured for endoscopic use, the construction can be dimensioned such that the elongated portion 222 has an outside diameter of about 5.5 mm. The elongated portion 222 of the clamp coagulator ultrasonic surgical instrument 202 may extend substantially orthogonally from the apparatus housing 204. The elongated portion 222 can be selectively rotated with respect to the housing 204 as described below. The elongated portion 222 may include an outer tubular member or sheath 224, an inner tubular actuating member 226, and the second acoustic portion of the acoustic system in the form of an end effector 206 including a blade 208. The outer sheath 224, the actuating member 226, and the end effector 206 may be joined together for indexed rotation as a unit (together with ultrasonic drive unit 204) relative to housing 212 by way of a rotation knob 228.

The end effector 206 may include a waveguide 220. The waveguide 220 may be substantially semi-flexible. It will be recognized that, alternatively, the waveguide 220 can be substantially rigid or may comprise a flexible wire. The waveguide 220 may be configured to amplify the mechanical vibrations transmitted through the waveguide 220 to the blade 208 as is well known in the art. The waveguide 220 may further comprise features to control the gain of the longitudinal vibration along the waveguide 220 and features to tune the waveguide 220 to the resonant frequency of the system.

It will be recognized that the blade 208 may comprise any suitable cross-sectional dimension. For example, the blade 208 may have a substantially uniform cross-section or the blade 208 may be tapered at various sections or may be tapered along its entire length. According to various embodiments, the blade 208 may be mechanically sharp formed with a cutting edge or may be mechanically blunt. The distal end of the blade 208 is disposed near an anti-node in order to tune the acoustic assembly to a preferred resonant frequency $f_o$ when the acoustic assembly is not loaded by tissue. When the transducer assembly is energized, the distal end of the blade 208 is configured to move longitudinally in the range of, for example, approximately 10-500 microns peak-to-peak, and preferably in the range of about 10 to about 100 microns at a predetermined vibrational frequency $f_o$. In accordance with the illustrated embodiment, the blade 208 may be cylindrical for cooperation with the associated clamping mechanism of the clamp coagulator ultrasonic surgical instrument 202. The waveguide 220 and the blade 208 may receive suitable surface treatment, as is known in the art.

Figure 7B:
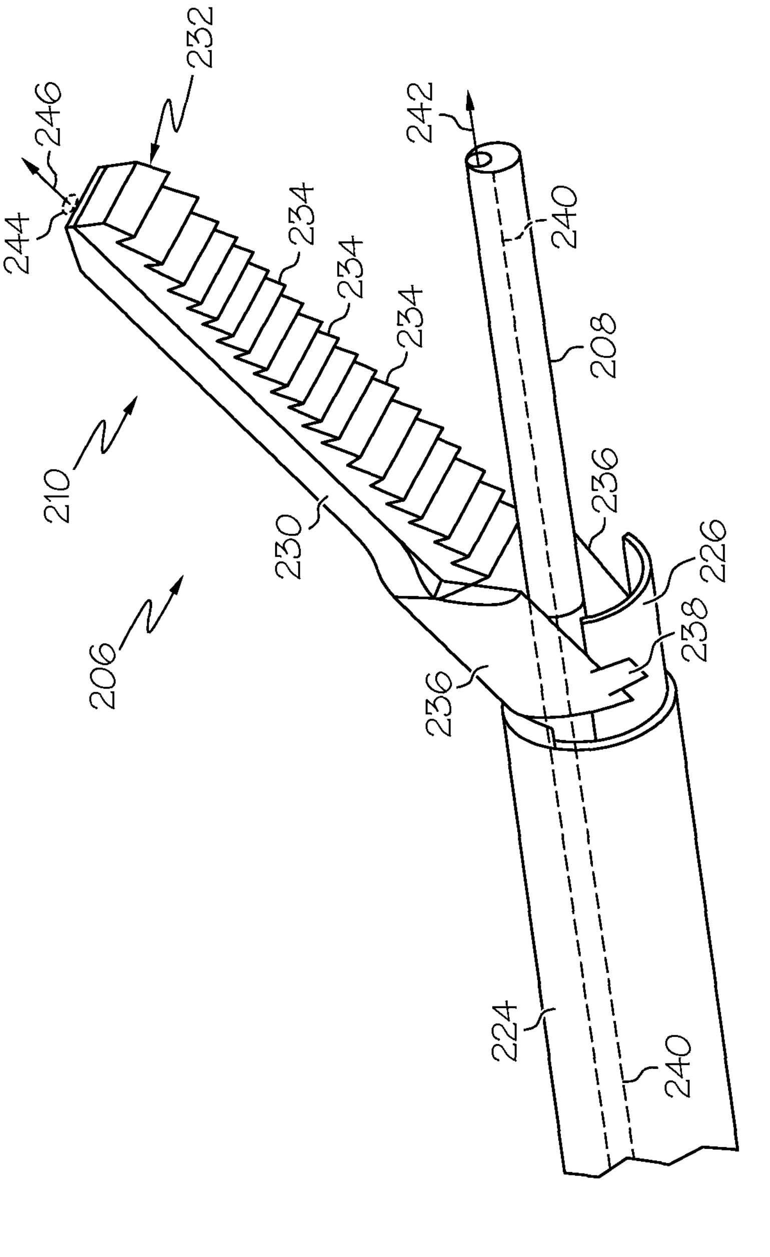
FIG. 7B illustrates one embodiment of a clamping mechanism that may be used with the surgical instrument shown in FIG. 7A.

FIG. 7B illustrates one embodiment of a clamping mechanism 210 that may be used with the surgical instrument shown in FIG. 7A. The clamping mechanism 210 may be configured for cooperative action with the blade 208 of the end effector 206. The clamping mechanism 208 includes a pivotally movable clamp arm 230, which is pivotally connected at the distal end thereof to the distal end of outer tubular sheath 224. The clamp arm 230 includes a clamp arm tissue pad 232, preferably formed from TEFLON® or other suitable low-friction material, which is mounted for cooperation with the blade 208, with pivotal movement of the clamp arm 230 positioning the clamp pad 232 in substantially parallel relationship to, and in contact with, the blade 208. By this construction, tissue to be clamped is grasped between the tissue pad 232 and the blade 208. The tissue pad 232 may be provided with a saw-tooth-like configuration including a plurality of axially spaced, proximally extending gripping teeth 234 to enhance the gripping of tissue in cooperation with the blade 208.

Pivotal movement of the clamp arm 230 with respect to the blade 208 is effected by the provision of at least one, and preferably a pair of lever portions 236 of the clamp arm 230 at the proximal end thereof. The lever portions 236 are positioned on respective opposite sides of the end effector 206 and the blade 208, and are in operative engagement with a drive portion 238 of the reciprocal actuating member 226. Reciprocal movement of the actuating member 226, relative to the outer tubular sheath 224 and the end effector 206, thereby effects pivotal movement of the clamp arm 230 relative to the blade 208. The lever portions 236 can be respectively positioned in a pair of openings defined by the drive portion 238, or otherwise suitably mechanically coupled therewith, whereby reciprocal movement of the actuating member 226 acts through the drive portion 238 and lever portions 236 to pivot the clamp arm 230.

The ultrasonic waveguide 220 and the blade 208 may comprise an inner lumen 240 extending longitudinally to receive and transfer fluid as indicated by arrow 242 to a target site. The target site may be the cutting, coagulating, or tissue welding site, for example. The lumen 240 is fluidically coupled to the fluid pump 64. In the embodiment, illustrated in FIGS. 7A, 7B, if the ultrasonic drive unit 204 is implemented as the ultrasonic transducer 14 shown in FIG. 1, the lumen 240 extends from the ultrasonic transmission waveguide 220 through the attachment post 54, the cannulated threaded stud 48, the velocity transformer 28, the end bell 22, the fore bell 20, the end bell 22, the ultrasonic transducer 14, and the coupling stud or bolt 35 and is fluidically coupled to the fluid pump 64 through one or more lumens 218. In the embodiment illustrated in FIGS. 7A, 7B, the ultrasonic drive unit 204 is implemented as the ultrasonic transducer 114 shown in FIG. 4. Accordingly, the lumen 240 extends from the ultrasonic transmission waveguide 220 through the attachment post 74 and is fluidically coupled to the fluid pump 64 through the input port 73. The fluid pump 64 is fluidically coupled to the lumen 240 such that fluid is communicated from the fluid pump 64 to the blade 208 and it emanates as shown by arrow 242 into the target site from the distal end of the blade 208. In one embodiment, the fluid may be chilled, heated, or the temperature thereof may be otherwise controlled by the fluid temperature regulator 65 before it is pumped into the lumen 240 by the fluid pump 64. In one embodiment, the fluid may be coupled through the lumen 240 to a fluidic channel 244 formed in the clamp arm 230. Accordingly, the fluid can flow through the clamp arm 230 and emanates from the channel 244 as indicated by arrow 246.

Figure 8:
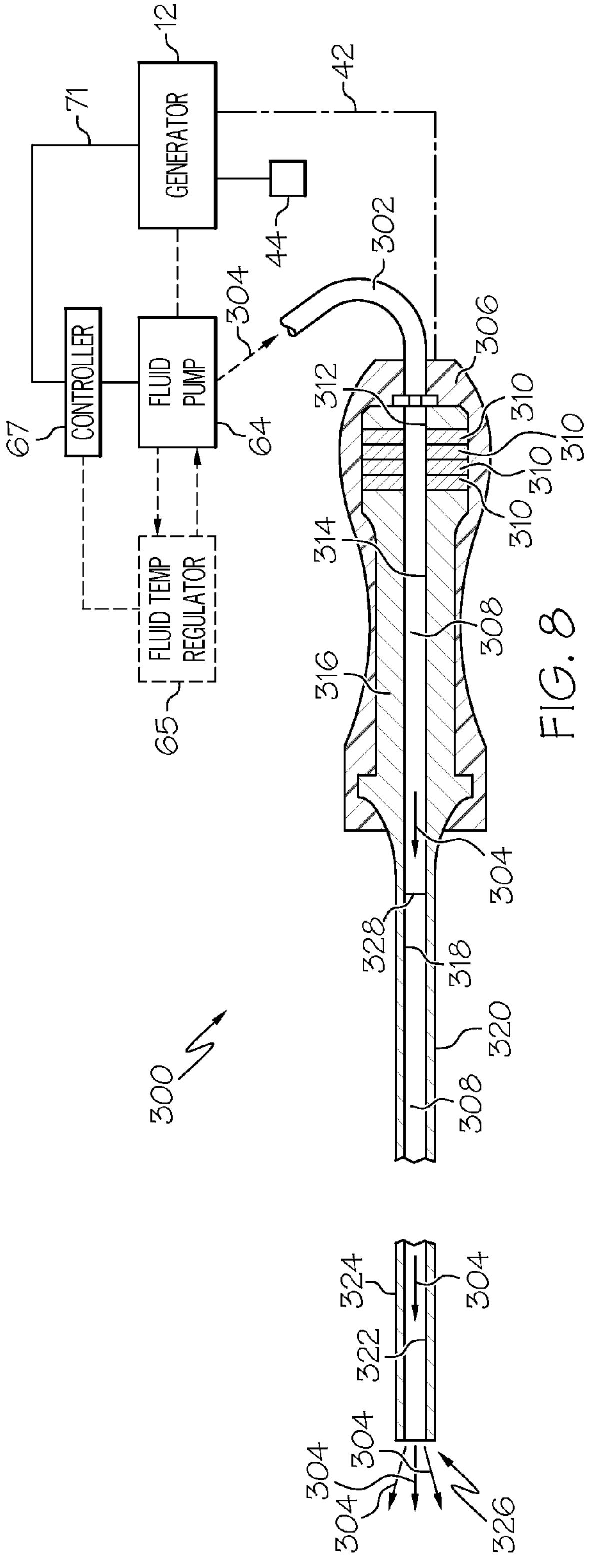
FIG. 8 illustrates one embodiment of an ultrasonic instrument comprising a transducer, a end effector, and a full length inner lumen.

FIG. 8 illustrates one embodiment of an ultrasonic instrument 300 comprising a transducer 316, a end effector 324, and a full length inner lumen 308. An ultrasonic waveguide 320 is coupled to the ultrasonic transducer 316 at a coupling connection or union/joint 328. The coupling connection 328 is substantially similar to the coupling connection 70 discussed with reference to FIG. 2. The full length inner lumen 308 extends from a proximal end of the instrument 300 to a distal end of the end effector 324 through the transducer 316 and the end effector 324. The lumen 308 extends longitudinally through several sections of the instrument 300. The lumen 308 extends through a bore 312 formed through piezoelectric elements 310 and a bore 314 formed through an ultrasonic transducer 316. The inner lumen 308 further extends through a bore 318 formed within an ultrasonic waveguide 320 and further extends through a bore 322 formed within a end effector 324. The bores 312, 314, 318, and 322 are substantially coaxially aligned and fluidically coupled.

A fluid line 302 is fluidically coupled to a proximal end of the inner lumen 308 and conducts a fluid 304 therethrough. The fluid line 302 receives the fluid 304 from the fluid pump 64 and/or the fluid temperature regulator 65. If the fluid 304 is used for cooling, the fluid 304 is conducted directly from the fluid pump 64 to the inner lumen 308 where it exits out of the distal end 36 of the end effector 324. If the fluid 304 is used for heating or to maintain the end effector 324 at a predetermined temperature, the fluid 304 is circulated through the fluid temperature regulator 65 and then is conducted into the lumen 308 by the fluid pump 64 either continuously or intermittently. The fluid line 302 is received through a housing portion 306 of the instrument 300 and is fluidically coupled to the inner lumen 308. The fluid 304 emanates or flows out from the distal end 326 of the end effector 324. The fluid 304 regulates the temperature of the end effector 324 and/or the surrounding tissue in the surgical region or target site.

The generator 12 or a controller 67 (referred to hereinafter as the controller 67) comprise circuits that may be configured to control the operation of the fluid pump 64 and/or the fluid temperature regulator 65. The controller 67 receives a feedback signal that is a direct or indirect measure of the temperature of the end effector 324. In one embodiment, as discussed in more detail below, the controller 67 may be coupled to a temperature sensor and receives a first feedback signal that is directly indicative of the temperature of the end effector 324, the fluid 304 or other components of the instrument 300. In one embodiment, as discussed in more detail below, the controller 67 may be coupled to the generator 12 and receives a second feedback signal that is indirectly indicative of the temperature of the end effector 324, the fluid 304 or other components of the instrument 300. The controller 67 is in electrical communication with (e.g., is electrically coupled to) the fluid pump 64. The controller 67 may control the operation of the fluid pump 64 and/or the fluid temperature regulator 65 either in an open loop manner without employing the feedback signal; or in a closed loop manner by employing the feedback signal. In either implementation, the controller 67 may operate the fluid pump 64 and/or the fluid temperature regulator 65 either continuously or intermittently to heat, cool, or otherwise regulate the temperature of the fluid 304, the end effector 324, the tissue within the target site, and/or any other component of the surgical instrument 300.

In one embodiment, the temperature of the ultrasonic end effector 324 may be controlled or regulated by employing a end effector temperature measurement signal as a feedback mechanism to the controller 67. Based on the temperature feedback signal, the controller 67 controls the operation of the fluid pump 64 and/or the fluid temperature regulator 65 by conducting or infusing water or another cooling fluid 304 through the lumen 308 to control or regulate the temperature of the end effector 324 to a predetermined temperature. Conducting or infusing the fluid 304 at a specified temperature keeps the end effector 324 at that temperature and absorbs excess energy from the system that would otherwise desiccate the tissue at the target site. The temperature of the end effector 324 may be measured using frequency change of the system or by direct measurement of the end effector or sheath temperature. In various embodiments an acoustic sensor may be used to measure frequency. End effector temperature may be controlled by chilling the cooling fluid 304 and conducting or infusing it through the end effector 324. The cooling fluid 304 may be employed to cool the ultrasonic end effector 324. The controller 67 and/or the generator 12 may be employed to measure the frequency changes of the end effector 324.

It is known that the frequency of the end effector 324 changes as a function of the temperature of the end effector 324. Accordingly, it is possible to approximate the temperature of the ultrasonic end effector 324 during use by measuring the resonant frequency of the ultrasonic transducer 316 system. For example, the resonant frequency of the ultrasonic transducer 316 system drops as the temperature of the end effector 324 increases during use. In one embodiment, the controller 67 and/or the generator 12 may be employed to detect the frequency variations of the ultrasonic transducer 316 system to derive an indirect measurement of the temperature of the end effector 324. The controller 67 and/or the generator 12 may determine the temperature of the end effector 324 based on the frequency feedback signal 71. The frequency feedback signal 71 is proportional to the temperature of the end effector 324. Based on the frequency feedback signal 71, the controller 67 controls the flow rate and/or the temperature of the fluid 304 supplied to the surgical area or to the end effector 324 to regulate the temperature of the end effector 324. The end effector 324 may be cooled by conducting fluid 304 at a lower temperature than the end effector 324 through the end effector 324 or to the tissue at the target site either continuously or intermittently to set and/or maintain a predetermined temperature. The indirect measurement of the temperature of the end effector 324 based on the frequency variations of the ultrasonic transducer 316 system may be determined empirically by experimentation or design parameters and programmed into the ultrasonic signal generator 12 or the controller 67 (e.g., in an integrated circuit within the instrument). The temperature of the fluid or the frequency of intermittent operation of the fluid pump 64 needed to maintain the end effector 324 at a predetermined temperature also may be determined empirically. The cooling fluid 304 may be conducted through the internal lumen 308 or cannulas formed inside the instrument 300 at any predetermined flow rate as may be necessary to keep the end effector 324 at the prescribed temperature. In another embodiment, the fluid may be conditioned to a predetermined temperature by the fluid temperature regulator 65 and then flowed through the inner lumen 308 at a predetermined flow rate to transfer any excess heat out of the system.

The irrigation lumen 308 formed within the body of the ultrasonic end effector 324 also forms a fluidic conduit to provide relatively constant or intermittent irrigation to the target site. In one embodiment, the irrigation lumen 308 of the end effector 324 may be fluidically coupled to the irrigation pump 64 that is programmed for continuous or intermittent activation. The ultrasonic end effector 324 can be used for tissue cutting and/or hemostasis (e.g., coagulation). During this process, the pump 64 remains shut-off or in a no-flow condition. Once the tissue load is removed from the end effector 324, the ultrasonic signal generator 12 senses the no load condition and provides a feedback signal that indicates an operational state of the ultrasonic end effector 324 to the controller 67 to control the pump 64 continuously or intermittently to supply the fluid 304 to the end effector 324 for a specified period. In one embodiment, the fluid 304 may be a cooling fluid. As previously discussed, in one embodiment, the controller 67 and/or the ultrasonic signal generator 12 may be adapted and configured to sense the temperature of the end effector 324 by a referred or indirect measurement of the temperature based on the transducer 316 system frequency. The fluid 304 may be conducted or infused continuously or intermittently to the end effector 324 until the end effector 324 reaches a predetermined temperature.

In another embodiment, the ultrasonic signal generator 12 or the controller 67 may be adapted and configured to control the conduction or infusion of the fluid 304 to the end effector 324 for a specified period after the operation of the end effector 324 is discontinued. In various embodiments, the controller 67 may be adapted and configured to control the conduction or infusion of the fluid 304 to the end effector 324 when the ultrasonic signal generator 12 is not actively driving the ultrasonic transducer 316. The conduction or infusion of fluid 304 may be independent of any temperature or frequency feedback signals. The conduction or infusion of fluid 304 may be, for example, for a predetermined amount of time and/or for predetermined repeating cycle. In another embodiment, the temperature of the end effector 324 may be monitored during this period to control the temperature of the end effector 324 to a specified temperature.

Figure 9:
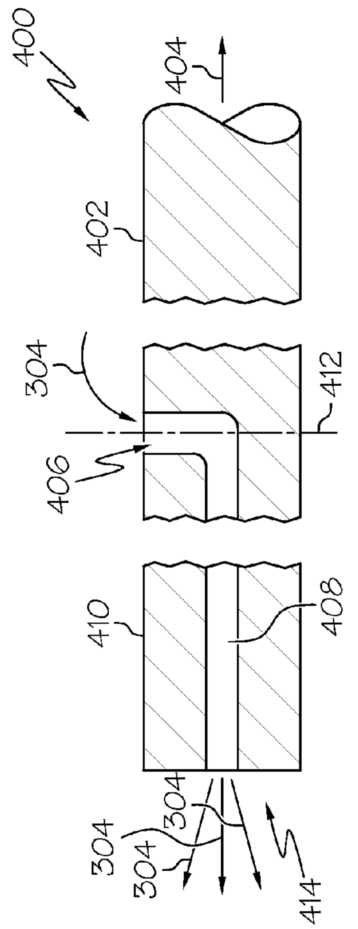
FIG. 9 illustrates a distal end of one embodiment of an ultrasonic instrument comprising a partial length inner lumen.

FIG. 9 illustrates a distal end of one embodiment of an ultrasonic instrument 400 comprising a partial length inner lumen 408. The ultrasonic instrument 400 comprises a solid ultrasonic waveguide 402 that is coupled to an ultrasonic transducer similar to the ultrasonic transducer 114 (FIG. 4) located in the direction indicated by arrow 404. The solid waveguide 402 is coupled to an end effector 410. The end effector 410 and/or the waveguide 402 comprises an inlet port 406 located at a node 412 to receive the fluid 304 from the fluid pump 64 (FIG. 4) and/or the fluid temperature regulator 65 (FIG. 4) to a cool, heat, or otherwise control or regulate the temperature of the fluid 304 and/or the end effector 410. The inlet port 406 is fluidically coupled to the partial length inner lumen 408. The fluid line 302 (FIG. 8) may be fluidically coupled to the inlet port 406 at the node 412 to conduct the fluid 304 to the partial length inner lumen 408. A first portion of the partial length inner lumen 408 extends longitudinally through a distal end 414 of the end effector 410 where the fluid 304 emanates or flows out therefrom. A second portion extends of the partial length inner lumen 408 aslant or transverse from the first portion and through a lateral portion of the end effector 410. In the illustrated embodiment, the second portion extends transversely from the first portion and extends through a lateral portion of the waveguide 402. As previously discussed with reference to FIG. 8, the controller 67 controls the operation of the fluid pump 64 and/or the fluid temperature regulator 65 continuously or intermittently to heat, cool, or otherwise regulate the temperature of the fluid 304 and/or the end effector 410. As discussed in more detail below, in yet another embodiment, the cooling fluid 304 may be conducted, infused, fed, or supplied either from a lumen formed within an outer sheath surrounding the waveguide 402 or from the fluid inlet port 406 coupled to the sheath. Either of these techniques is suitable for conducting, infusing, spraying or otherwise channeling the fluid 304 to an exterior portion of the end effector 324 to control the temperature thereof.

Figure 10:
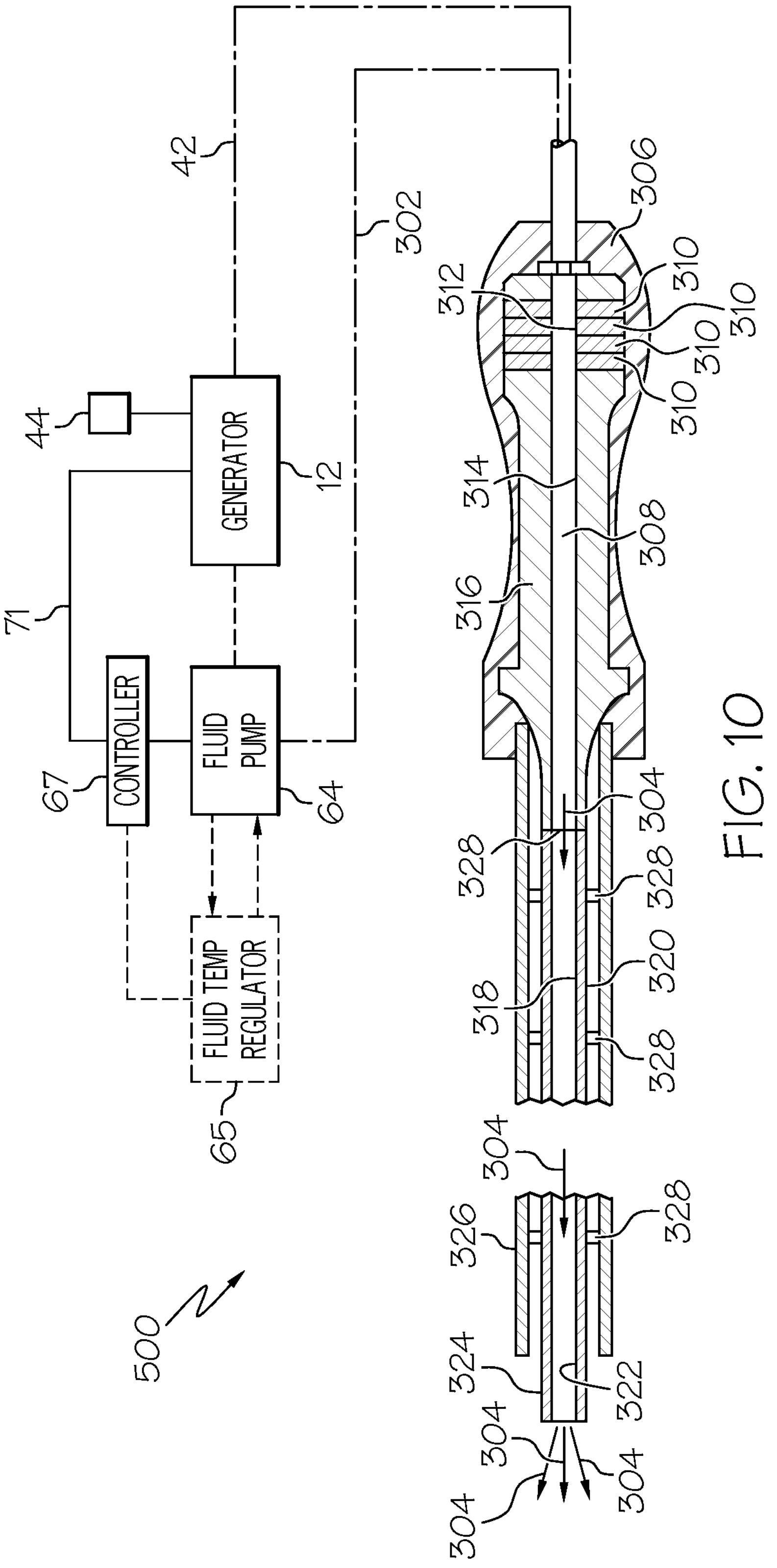
FIG. 10 illustrates one embodiment of an ultrasonic instrument.
Figure 11:
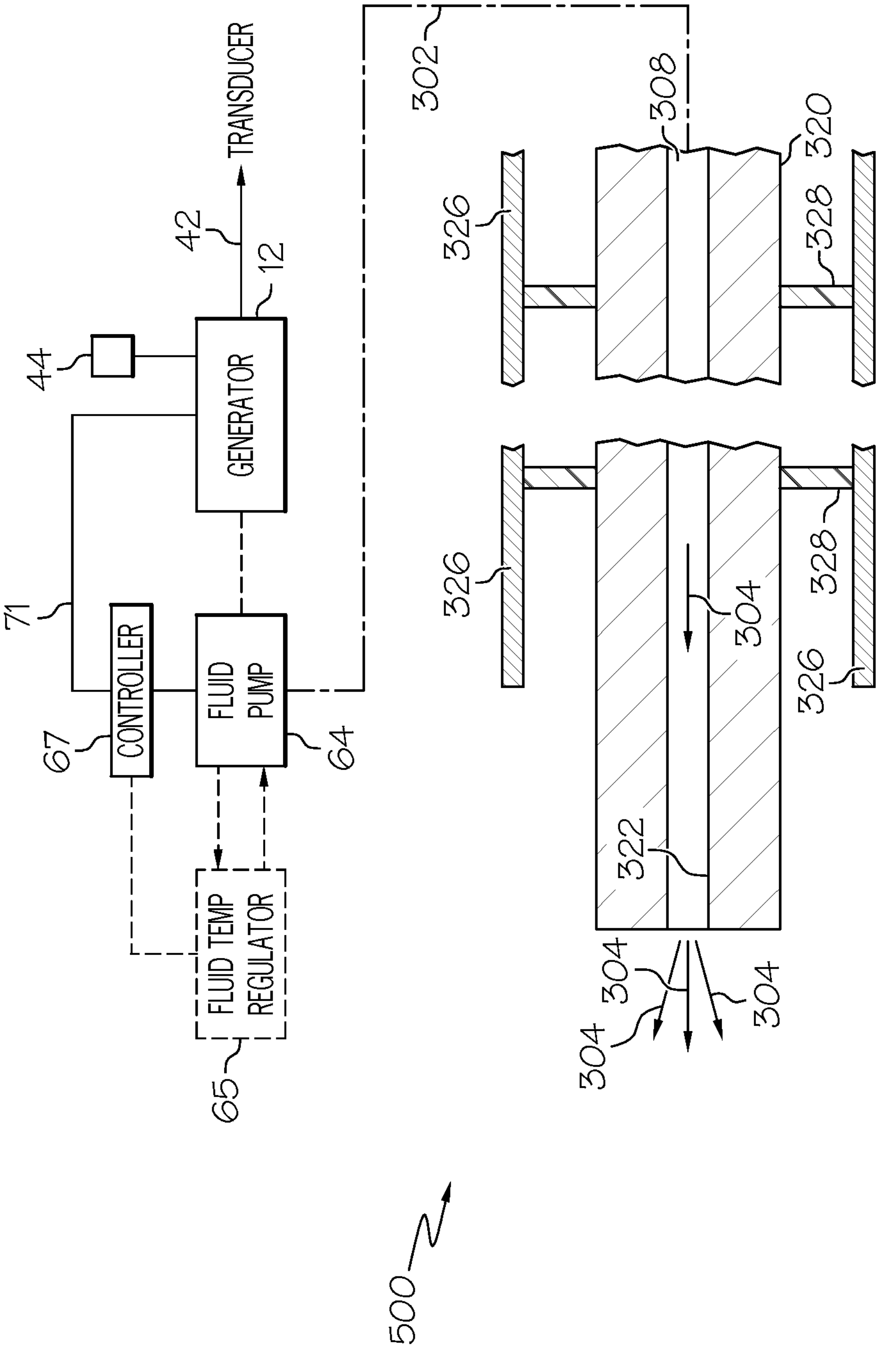
FIG. 11 illustrates a detail view of a distal end of the ultrasonic instrument shown in FIG. 10.

FIG. 10 illustrates one embodiment of an ultrasonic instrument 500. FIG. 11 illustrates a detail view of a distal end of the ultrasonic instrument 500. With reference to FIGS. 10 and 11, the ultrasonic instrument 500 comprises the instrument 300 discussed in FIG. 8 with an outer sheath 326 provided over the ultrasonic transmission waveguide 320. As previously discussed, the ultrasonic instrument 300 comprises the transducer 316, the end effector 324, and the full length inner lumen 308. The outer sheath 326 is isolated from the waveguide 320 by a plurality of stabilizing silicone rings or compliant supports 328 positioned at a plurality of nodes. The compliant supports 328 dampen undesirable vibration and isolate the ultrasonic energy from the removable sheath 326 assuring the flow of ultrasonic energy in a longitudinal direction to the distal end of the end effector 324 with maximum efficiency.

As previously discussed, the full length inner lumen 308 extends from a proximal end of the instrument 300 to a distal end of the end effector 324 through the transducer 316 and the end effector 324. The lumen 308 is fluidically coupled to the fluid line 302 to receive the fluid 304 from the fluid pump 64 and/or the fluid temperature regulator 65 and to conduct the fluid 304 to the end effector 324. The fluid 304 emanates or flows out from the distal end 326 of the end effector 324 through the bore 322.

As previously discussed, the temperature of the end effector 324 may be measured directly or indirectly. In one embodiment, the temperature of the end effector 324 may be determined directly with a temperature sensor, indirectly by measuring the operating frequency of the end effector 324 and deriving the temperature, or using a combination of these techniques. The controller 67 receives either a temperature feedback signal 332 from a temperature sensor 330 (FIGS. 12, 13, 16-20, 23, and 24), the frequency feedback signal 71, or a combination thereof, to determine the temperature of the end effector 324. The controller 67 uses the feedback information to regulate the temperature of the end effector 324 by controlling the flow rate and/or the temperature of the fluid 304. The temperature sensor 330 may comprise thermocouple or thermistor type devices, for example. To regulate the temperature of the end effector 324, the controller 67 controls the operation of the fluid pump 64 and/or the fluid temperature regulator 65 continuously, intermittently, or for a predetermined period, as previously discussed. In the illustrated embodiment, the temperature of the end effector 324 may be measured indirectly by detecting variations in the operating frequency of the end effector 324 and providing the frequency feedback signal 71 to the controller 67. The controller 67 determines the temperature of the end effector 324 based on the correlated frequency feedback signal 71 and controls the flow rate and/or the temperature of the fluid 304 supplied to the end effector 324 or the target site to regulate the temperature of the end effector 324. The controller 67 also controls the operation of the fluid pump 64.

Figure 12:
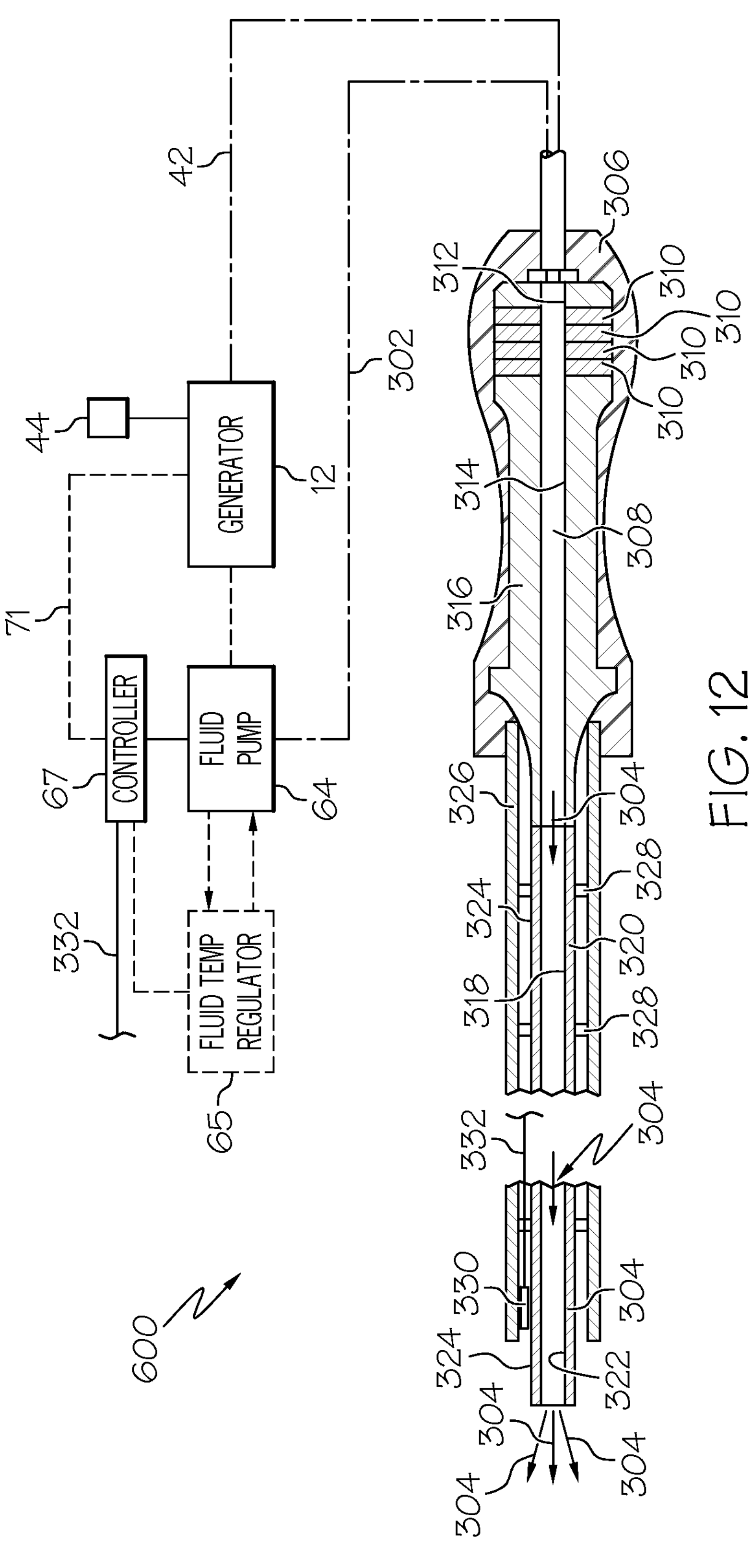
FIG. 12 illustrates one embodiment of an ultrasonic instrument.
Figure 13:
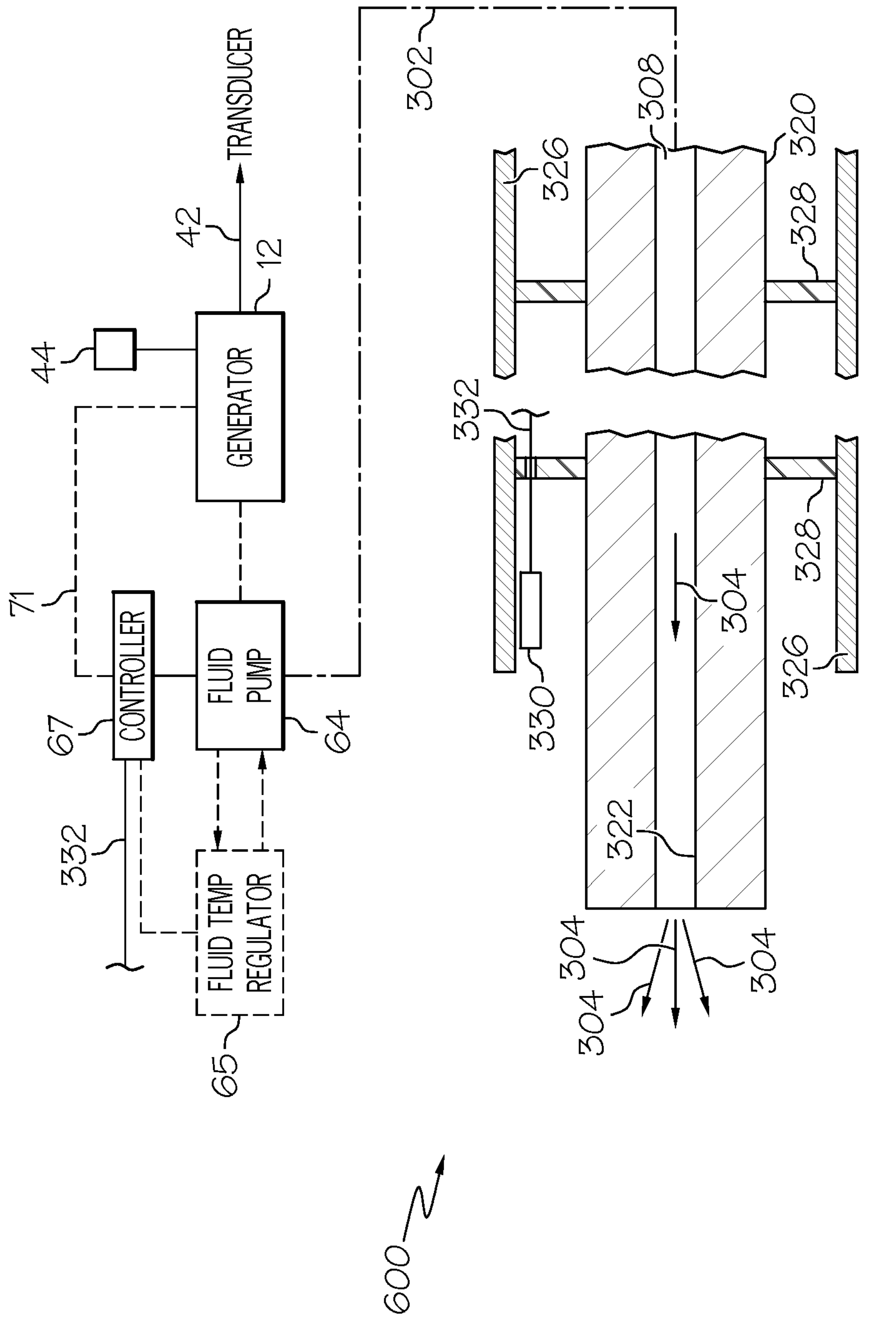
FIG. 13 illustrates a detail view of a distal end of the ultrasonic instrument shown in FIG. 12.

FIG. 12 illustrates one embodiment of an ultrasonic instrument 600. FIG. 13 illustrates a detail view of a distal end of the ultrasonic instrument 600. With reference to FIGS. 12 and 13, the ultrasonic instrument 600 comprises the instrument 400 discussed in FIGS. 10 and 11 and further comprises a temperature sensor 330 located within the outer sheath 326 to measure the temperature of the end effector 324. As previously discussed, the ultrasonic instrument 600 comprises the transducer 316, the end effector 324, and the full length inner lumen 308. The temperature sensor 330 provides a temperature feedback signal 332 to the controller 67. Optionally, the temperature of the end effector 324 may be measured by detecting the frequency of the end effector 324 and providing the frequency feedback signal 71 to the controller 67. In the illustrated embodiment, the controller 67 may determine the temperature of the end effector 324 based on the temperature feedback signal 332, or the frequency feedback signal 71, or a combination thereof. The controller 67 adjusts the flow rate and/or the temperature of the fluid 304 supplied to the end effector 324 or the target site to regulate the temperature of the end effector 324 based on the temperature feedback signal 332, the frequency feedback signal 71, or a combination thereof.

Figure 14:
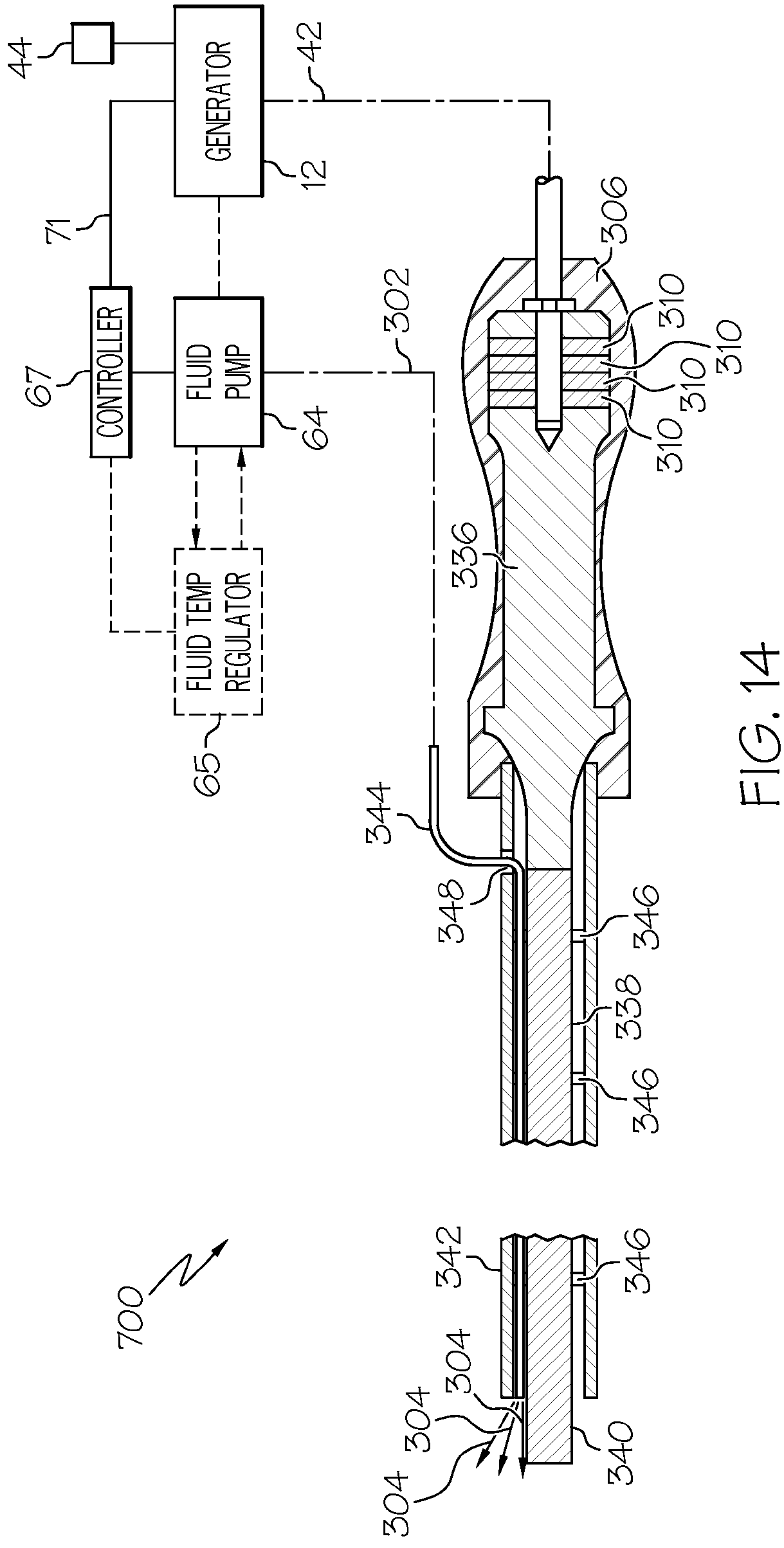
FIG. 14 illustrates one embodiment of an ultrasonic instrument.
Figure 15:
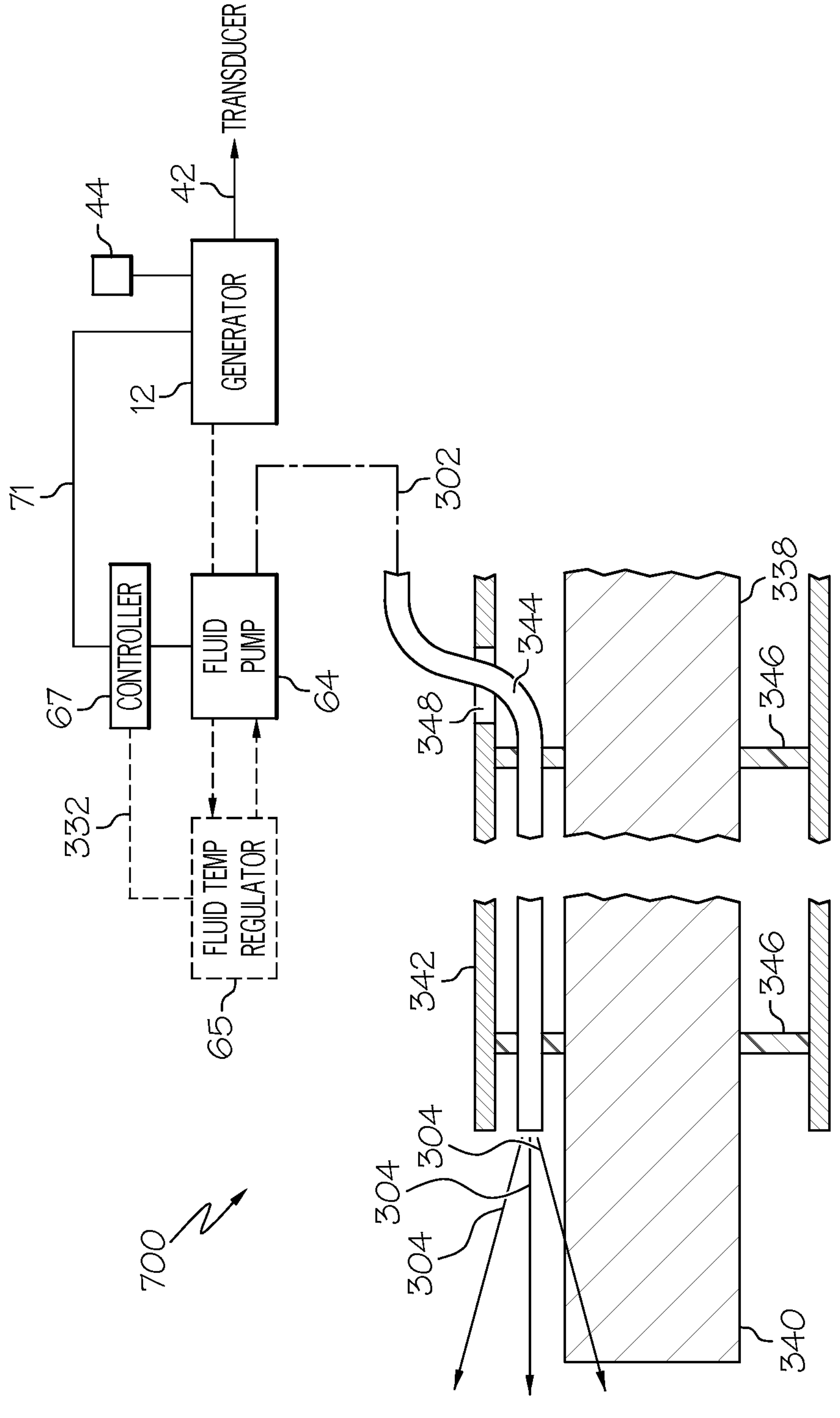
FIG. 15 illustrates a detail view of a distal end of the ultrasonic instrument shown in FIG. 14.

FIG. 14 illustrates one embodiment of an ultrasonic instrument 700. FIG. 15 illustrates a detail view of a distal end of the ultrasonic instrument 700. With reference to FIGS. 14 and 15, in one embodiment the ultrasonic instrument 700 comprises a transducer 336, an end effector 340 with a solid body, an outer sheath 342, and a cannula, lumen, conduit, or tube 344 located within the outer sheath 342. The end effector 340, the ultrasonic waveguide 338, and the transducer 336 comprise solid bodies with no inner lumen. The tube 344 may be located between the body of the ultrasonic waveguide 338 and the outer sheath 342. The tube 344 is inserted through an opening 348 or inlet port formed in the outer sheath 342. The tube 344 is fluidically coupled to the fluid line 302 and the fluid pump 64. The tube receives the fluid 304 from the fluid pump 64. The temperature of the end effector 340 may be measured indirectly by the generator 12 or the controller 67 by detecting variations in the operating frequency of the end effector 340, providing the frequency feedback signal 71 to the controller 67, and determining the temperature of the end effector 340 based on the frequency. The controller 67 receives the frequency feedback signal 71 and determines the temperature of the end effector 340 based on the frequency feedback signal 71. The controller 67 regulates the temperature of the end effector 340 by controlling the flow rate and/or temperature of the fluid 304 conducted to the end effector 340 and the target site until the end effector 340 reaches the desired temperature. The controller 67 may control the operation of the fluid pump 64 and/or the fluid temperature regulator 65 either continuously or intermittently, as previously discussed, to regulate the temperature of the end effector 340. In the illustrated embodiment, the fluid is supplied through the tube 344. In other embodiments, however, the fluid 304 may be conducted, fed, or supplied directly through the opening 348 to a lumen formed within the outer sheath 342 or to the space between the outer sheath 342 and the waveguide 338. Either technique is suitable for conducting, spraying, or channeling the fluid 304 over the exterior portion of the end effector 340 to control the temperature thereof.

Figure 16:
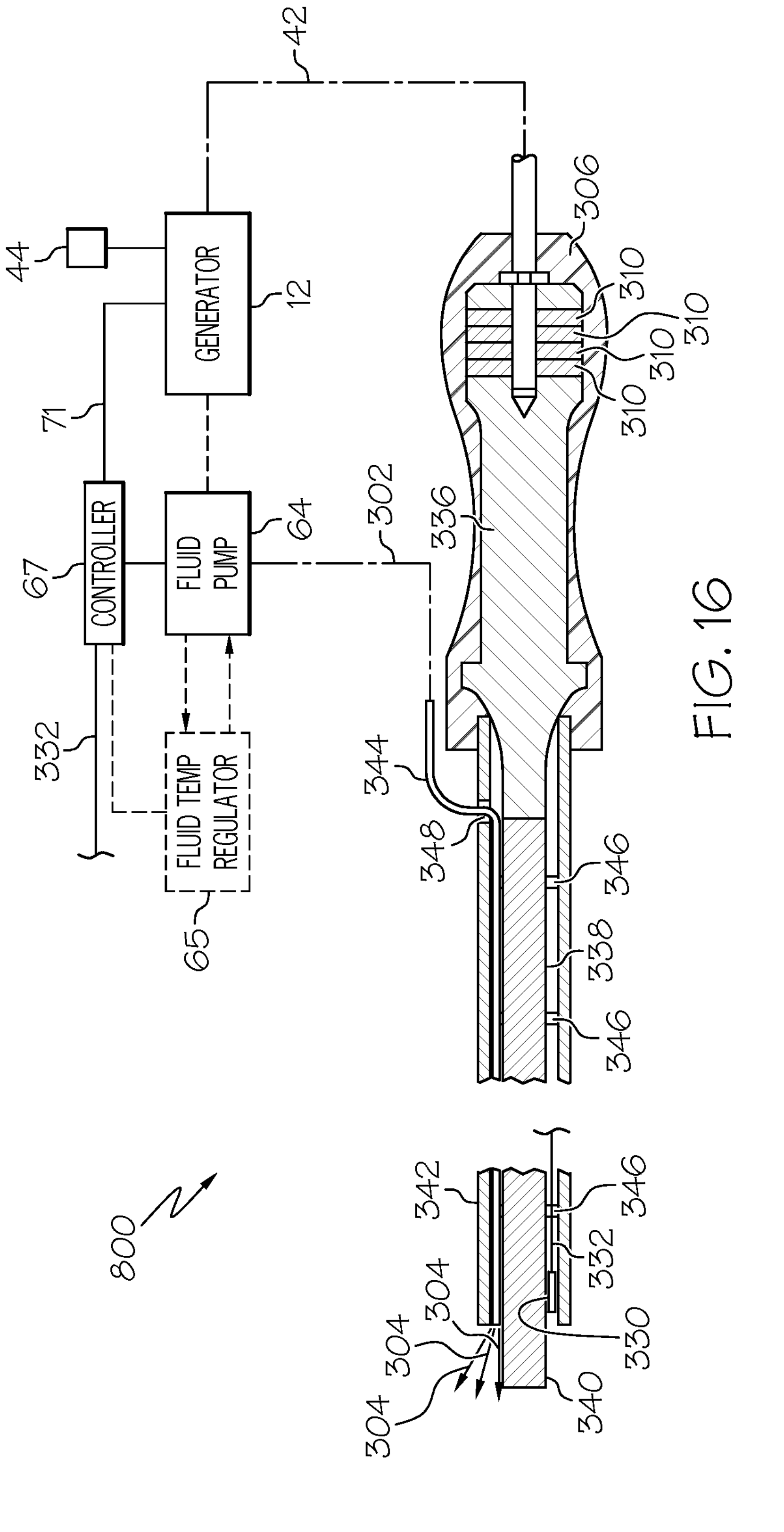
FIG. 16 illustrates one embodiment of an ultrasonic instrument.
Figure 17:
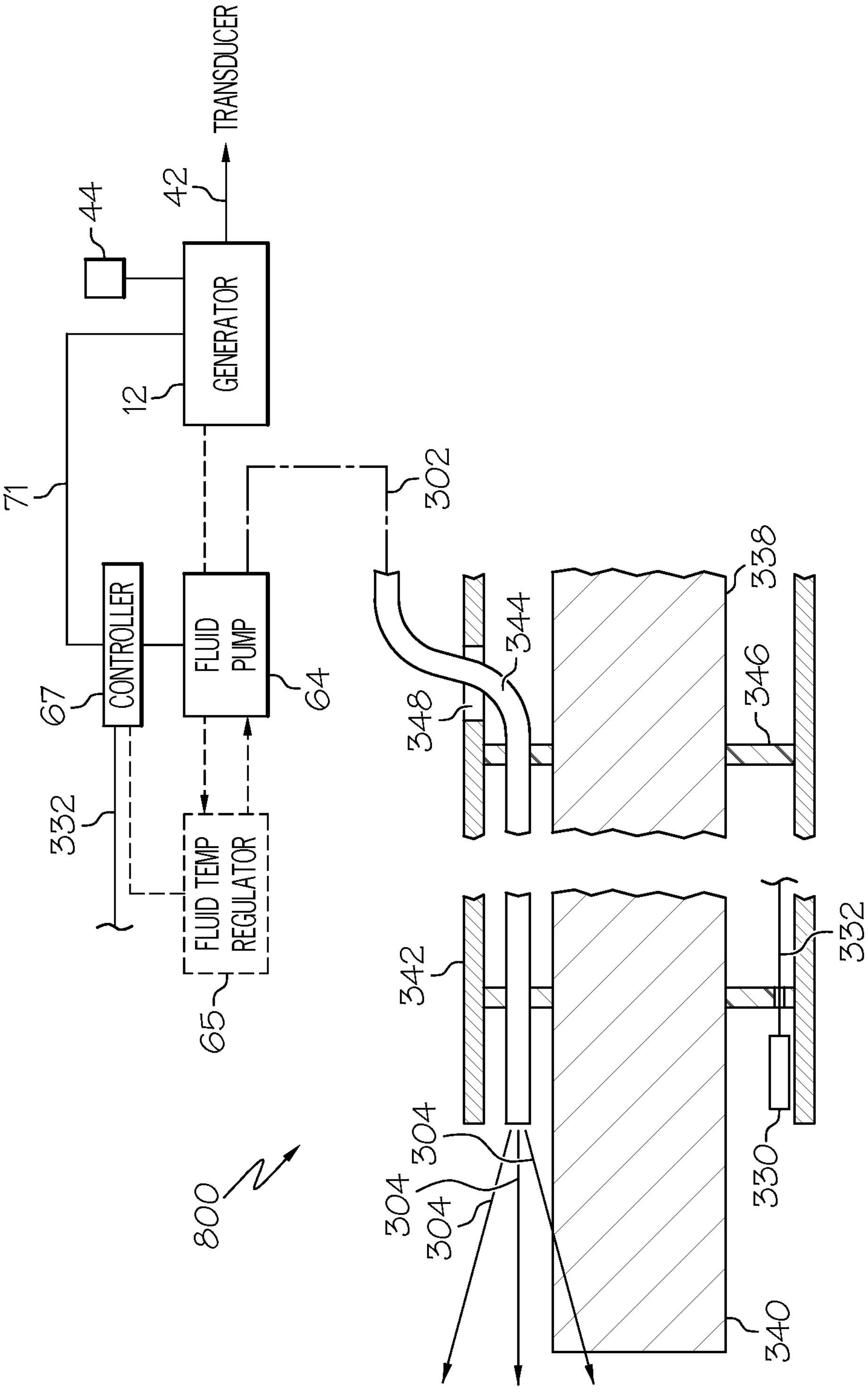
FIG. 17 illustrates a detail view of a distal end of the ultrasonic instrument shown in FIG. 16.

FIG. 16 illustrates one embodiment of an ultrasonic instrument 800. FIG. 17 illustrates a detail view of a distal end of the ultrasonic instrument 800. The ultrasonic instrument 800 comprises the instrument 700 discussed in FIGS. 14 and 15 and further comprises the temperature sensor 330 located within the outer sheath 342 to measure the temperature of the end effector 340. As previously discussed, the ultrasonic instrument 800 comprises the transducer 336, the end effector 340 with the solid body, the outer sheath 342, and the cannula, lumen, conduit, or tube 344 located within the outer sheath 342. The end effector 340, the ultrasonic waveguide 338, and the transducer 336 comprise solid bodies with no inner lumen. The tube 344 may be located between the body of the ultrasonic waveguide 338 and the outer sheath 342. The tube 344 is inserted through an opening 348 or inlet port formed in the outer sheath 342. The tube 344 is fluidically coupled to the fluid line 302 and the fluid pump 64. The tube 344 receives the fluid 304 from the fluid pump 64. The temperature sensor 330 provides the temperature feedback signal 332 to the controller 67. In one embodiment, the temperature of the end effector 340 may be measured by detecting the frequency of the end effector 340 and providing the frequency feedback signal 71 to the controller 67 to adjust the flow rate and/or temperature of the fluid 304 flowing into the target site to regulate the temperature of the end effector 340. In one embodiment, the temperature of the end effector 324 may be determined using a combination of these techniques. Based on the temperature feedback signal 332, the frequency feedback signal 71, or a combination thereof, the controller 67 determines the temperature of the end effector 340, and regulates the temperature of the end effector 340 by controlling the flow rate and/or the temperature of the fluid 304 supplied to the end effector 340 and target site with the fluid pump 64 and/or the fluid temperature regulator 65 until the desired temperature is reached, as previously discussed. The fluid pump 64 and/or the fluid temperature regulator 65 may be operated continuously or intermittently until the desired temperature is reached. The fluid 304 may be fed, supplied, or conducted through the tube 344 formed within the outer sheath 342 and provided through the opening 348. This technique also is suitable for spraying, conducting, or otherwise channeling the fluid 304 over the exterior of the end effector 340 to control the temperature thereof.

Figure 18:
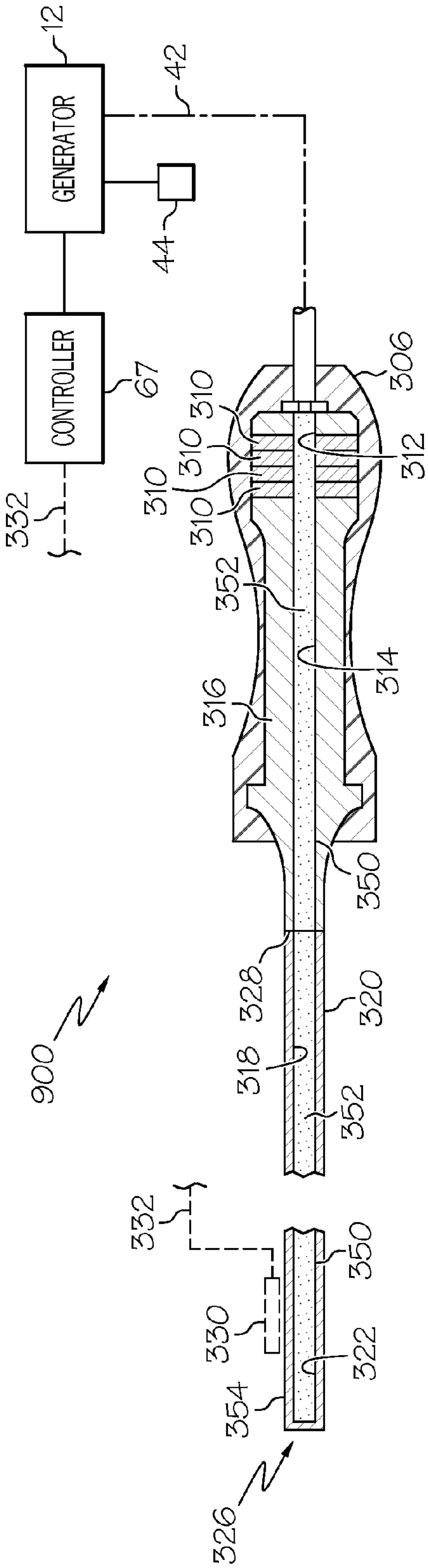
FIG. 18 illustrates one embodiment of an ultrasonic instrument comprising a transducer, a end effector, and a full length sealed inner lumen.

FIG. 18 illustrates one embodiment of an ultrasonic instrument 900 comprising the transducer 316, a end effector 354, and a full length sealed inner lumen 352. The ultrasonic waveguide 320 is coupled to the ultrasonic transducer 316 at the coupling connection or union/joint 328. The coupling connection 328 is substantially similar to the coupling connection 70 discussed with reference to FIG. 2. The full length sealed inner lumen 352 extends from a proximal end of the instrument 300 to a distal end of the end effector 324 through the transducer 316 and the end effector 354. The sealed inner lumen 352 extends longitudinally through several sections of the instrument 300. The sealed inner lumen 352 extends through a bore 312 formed through piezoelectric elements 310 and a bore 314 formed through an ultrasonic transducer 316. The sealed inner lumen 352 further extends through a bore 318 formed within an ultrasonic waveguide 320 and further extends through a bore 322 formed within the end effector 354. The distal end 326 of the end effector 354 is sealed. The bores 312, 314, 318, and 322 are substantially coaxially aligned.

In one embodiment, the inner lumen 352 is filled with a phase change material 350. The phase change material 350 is sealed within the inner lumen 352. The phase change material 350 may comprise any material that changes from a solid or liquid phase to a gaseous phase. The phase change material 350 controls the temperature of the end effector 354. As the phase change material 350 changes from a solid or liquid phase to a gaseous phase it absorbs heat to maintain the end effector 354 at a specified temperature. The phase change material 350 acts like a heat pipe material, absorbing heat at the end effector/tissue interface and releasing the heat away from the interface. The heat pipe is a heat transfer mechanism that can transport large quantities of heat with a very small difference in temperature between the hot and cold interfaces. A heat pipe may comprise a sealed hollow tube such as the sealed inner lumen 352. The waveguide 320 and the end effector 354 may be formed of Ti6Al4V (an alloy of Titanium including Aluminum and Vanadium), Aluminum, Stainless Steel, or other suitable materials, that have thermoconductive properties. The pipe is formed of the waveguide 320 and the end effector 354 comprising the inner sealed lumen 352 filled with a relatively small quantity of the phase change material 350 that acts as a "working fluid" or coolant (such as water, ethanol, or mercury). The rest of the pipe is filled with vapor phase of the phase change material 350 or working fluid, all other gases being excluded.

In one embodiment, the temperature sensor 330 may be embedded in an instrument sheath (e.g., the sheath 326 in FIG. 12) or the end effector 354 to measure and correlate the temperature of the end effector 324. The temperature sensor 330 may comprise thermocouple or thermistor type devices, for example.

Figure 19:
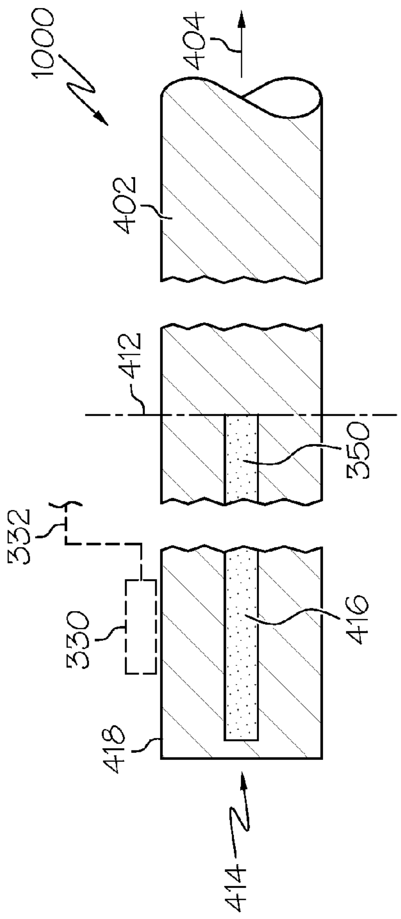
FIG. 19 illustrates a distal end of one embodiment of an ultrasonic instrument comprising a partial length sealed inner lumen.

FIG. 19 illustrates a distal end of one embodiment of an ultrasonic instrument 1000 comprising a partial length sealed inner lumen 416. The ultrasonic instrument 1000 comprises a solid ultrasonic waveguide 402 that is coupled to an ultrasonic transducer similar to the ultrasonic transducer 114 (FIG. 4) located in the direction indicated by arrow 404. The solid waveguide 402 is coupled to a end effector 418. The partial length sealed inner lumen 416 may extend into the end effector 418 region and/or the waveguide 402 region. The phase change material 350 may be disposed within the partial length sealed inner lumen 416 in the end effector 418 and/or the waveguide 402 portions of the ultrasonic instrument 1000. As previously discussed, the phase change material 350 may comprise any material that changes from a solid or liquid phase to a gaseous phase. The phase change material 350 is located inside the partial length sealed inner lumen 416 to control the temperature of the end effector 418.

In one embodiment, the temperature sensor 330 may be embedded in an instrument sheath (e.g., the sheath 326 in FIG. 12) or the end effector 418 to measure and correlate the temperature of the end effector 418. The temperature sensor 330 may comprise thermocouple or thermistor type devices, for example.

Figure 20:
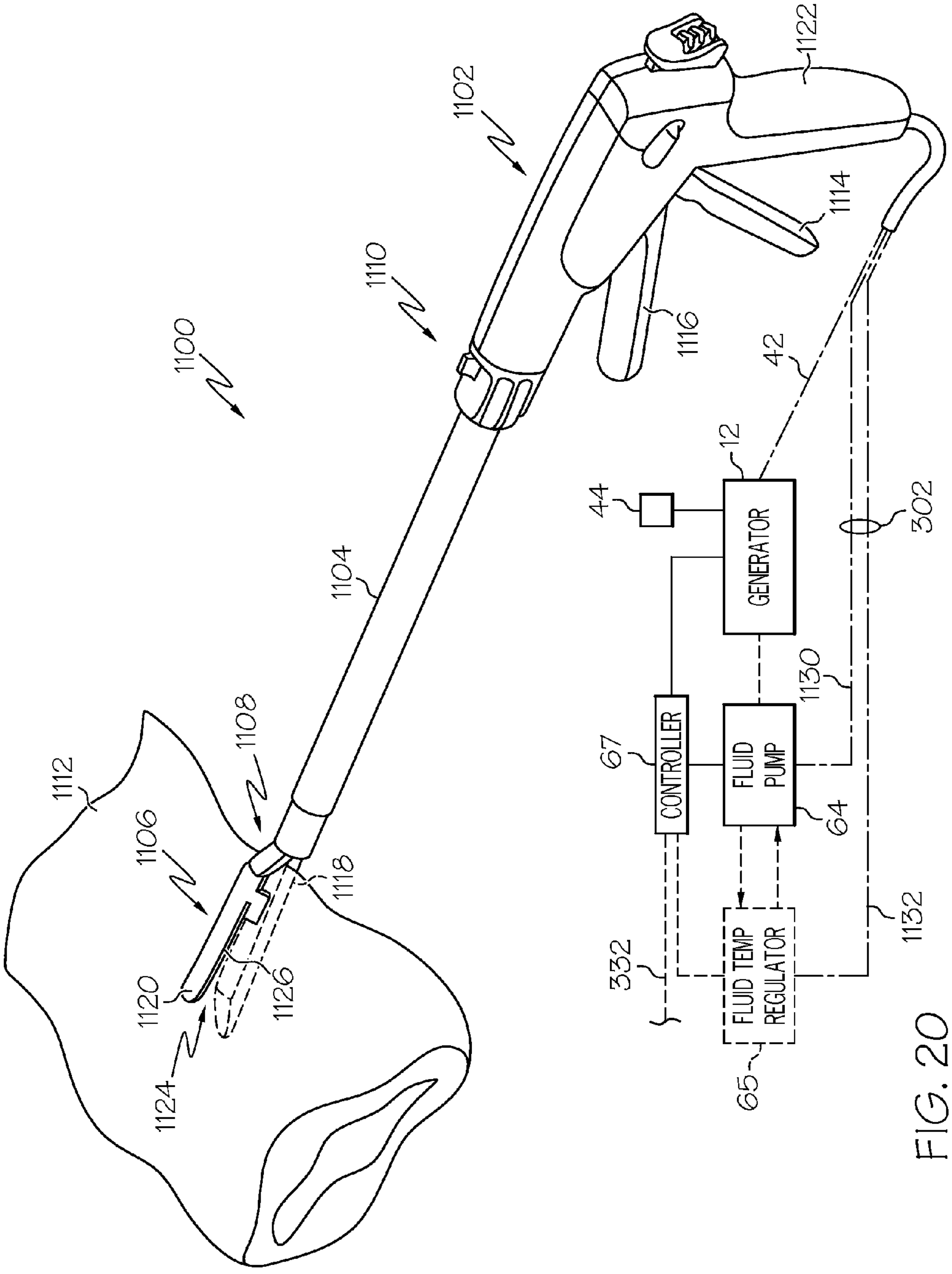
FIG. 20 illustrates one embodiment of a tissue welding apparatus.

FIG. 20 illustrates one embodiment of a tissue welding apparatus 1100. The tissue welding apparatus 1100 may be employed to sever and weld tissue 1112. In one embodiment, the tissue welding apparatus 1100 comprises a handle 1102, a shaft 1104, and a tissue welding end effector 1106 pivotally connected to the shaft 104 at pivot 1108. The placement and orientation of the tissue welding end effector 1106 may be facilitated by controls located on the handle 1102, including a rotation knob 1110 for rotating the shaft 1104 and the tissue welding end effector 1106 about an axis. In one embodiment, the placement and orientation of the tissue welding end effector 1106 may be facilitated by an articulation control for effecting the rotation, or articulation, of the end effector 1106 with respect to the shaft 1104 about the articulation pivot 1108. In various embodiments, the handle 1102 of the tissue welding apparatus 1100 may comprise a closure trigger 1114 and a firing trigger 1116 for actuating the tissue welding end effector 1106 as described in greater detail below. It will be appreciated, however, that instruments having end effectors configured to perform different surgical tasks may have different numbers or types of triggers or other suitable controls for operating the tissue welding end effector 1106. Furthermore, as previously discussed, it will be appreciated that the terms "proximal" and "distal" are used herein with reference to a clinician gripping the handle 1102 of the tissue welding apparatus 1100. Thus the tissue welding end effector 1106 is distal with respect to the handle 1102.

In the illustrated embodiment, the tissue welding end effector 1106 can be configured to clamp, sever, and weld soft tissue, for example. In other embodiments, different types of end effectors may be used such as graspers, cutters, staplers, clip appliers, access devices, drug/gene therapy devices, ultrasound, RF and/or laser devices, for example. The tissue welding end effector 1106 can include, among other things, an ultrasonic tissue treating blade 1118 and a translatable clamping member, such as an anvil 1120, for example, where the ultrasonic tissue treating blade 1118 and the anvil 1120 can be relatively positioned, or spaced, in order to assure that the soft tissue 1112 clamped in the tissue welding end effector 1106 is properly welded and incised. The handle 1102 can include a pistol grip 1122 towards which a closure trigger 1114 can be pivotally drawn in order to move the anvil 1120 toward the ultrasonic tissue treating blade 1118 and clamp the tissue 1112 positioned between the anvil 1120 and the ultrasonic tissue treating blade 1118. Stated another way, once the clinician is satisfied with the positioning of the end effector 1106, the clinician may draw back the closure trigger 1114 to a position in which the anvil 1120 is fully closed and the closure trigger 1114 is locked into position. Thereafter, the firing trigger 1116 may be pivotally drawn toward the pistol grip 1122 to weld and sever the soft tissue 1120 clamped in the end effector 1106.

Figure 21:
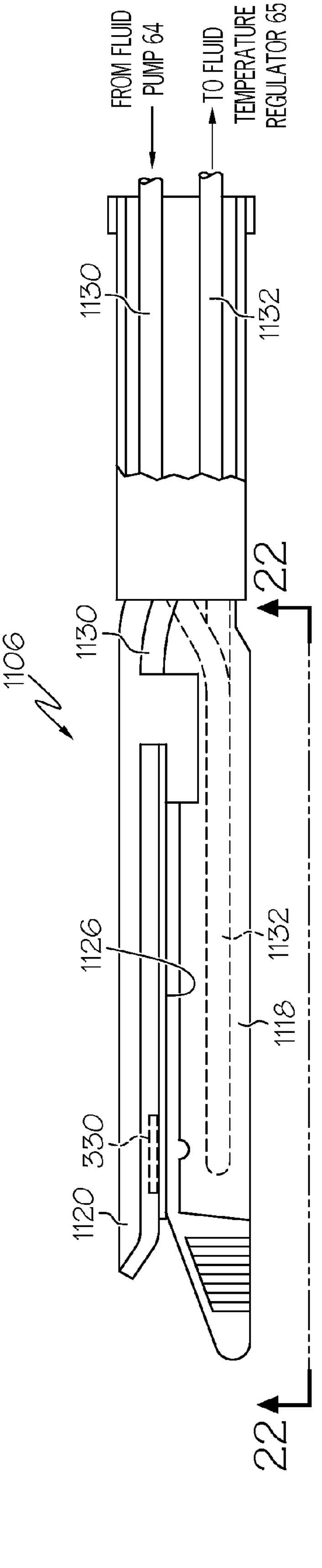
FIG. 21 illustrates one embodiment of the end effector portion of the tissue welding apparatus shown in FIG. 20.
Figure 22:
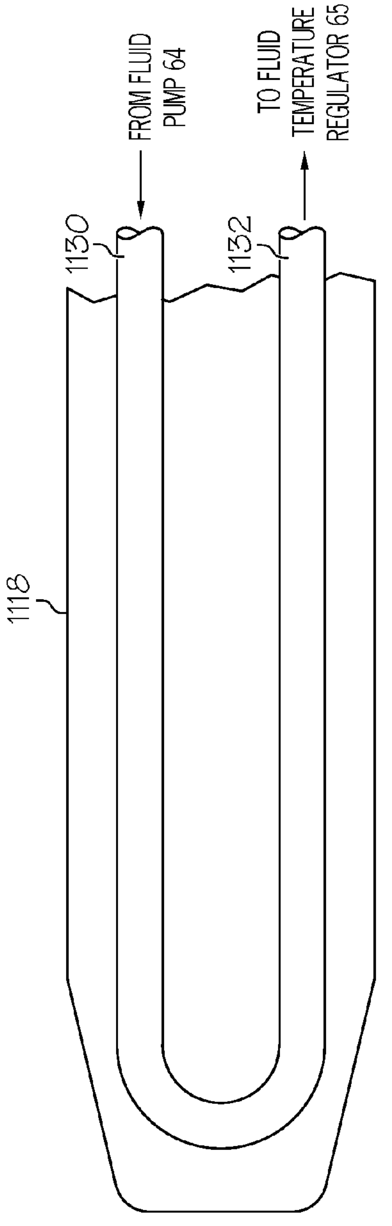
FIG. 22 is a bottom view of the of the end effector portion of the tissue welding apparatus taken along line 22-22.

As shown in FIGS. 21 and 22 below, the tissue welding end effector 1106 comprises an inlet line 1130 and an outlet line 1132. The inlet line 1130 conducts the fluid 304 from the fluid pump 64 and/or the fluid temperature regulator 65 to the tissue welding ultrasonic blade 1118. A strong coagulation region may be achieved by maintaining the temperature of the surface of the blade 1118 at a point between where coagulation of the tissue 1112 can occur and where desiccation of the tissue does not occur. Lowering the temperature of the ultrasonic blade 1118 enables the blade 1118 to contact the tissue 1112 for a longer period. This enables both sides of the tissue 1112 in contact with the blade 1118 and a coaptation pad 1126 formed on the tissue clamping portion of the anvil 1120 to form viable coagulation zones to improve the weld strength of the tissue 1112. As discussed below with reference to FIG. 24, in another embodiment, the same blade 1118 cooling fluid may be flowed through the coaptation pad 1126 to increase the temperature of the tissue 1112 on the opposite side of the blade 1118.

FIG. 21 illustrates one embodiment of the end effector 1106 portion of the tissue welding apparatus 1100. The inlet line 1130 is fluidically coupled to the fluid pump 64 (FIG. 20) and receives fluid from the fluid pump 64. The inlet line 1130 is disposed beneath the blade 1118. The outlet line 1132 is fluidically coupled to either to the fluid pump 64 and/or the fluid temperature regulator 65. The fluid is circulated by the fluid pump 64. In one embodiment, the fluid may be heated by the fluid temperature regulator 65 prior to being circulated by the fluid pump 64 via the inlet line 1130.

FIG. 22 is a bottom view of the of the end effector 1106 portion of the tissue welding apparatus 1100 taken along line 22-22. With reference now, to FIGS. 20-22, the tissue welding apparatus 1100 may be coupled to the generator 12 to operate the tissue welding ultrasonic blade 1118. The tissue welding ultrasonic blade 1118 also may be coupled to the inlet line 1130 and the outlet line 1132. The fluid pump 64 is fluidically coupled to the inlet and the outlet lines 1130, 1132. The pump 64 circulates the fluid through the inlet line 1130 and the outlet line 1132. To heat the fluid, the fluid may be circulated to the fluid temperature regulator 65. The controller 67 controls the operation of the fluid pump 64 and/or the fluid temperature regulator 65. The fluid is communicated from the fluid pump 64 to the blade 1118 via the inlet line 1130 and the fluid returns either to the fluid pump 64 or to the fluid temperature regulator 65 via the outlet line 1132. In one embodiment, the fluid may be heated by the fluid temperature regulator 65 before it is pumped continuously or intermittently into the fluid inlet line 1130 by the fluid pump 64.

Figure 23:
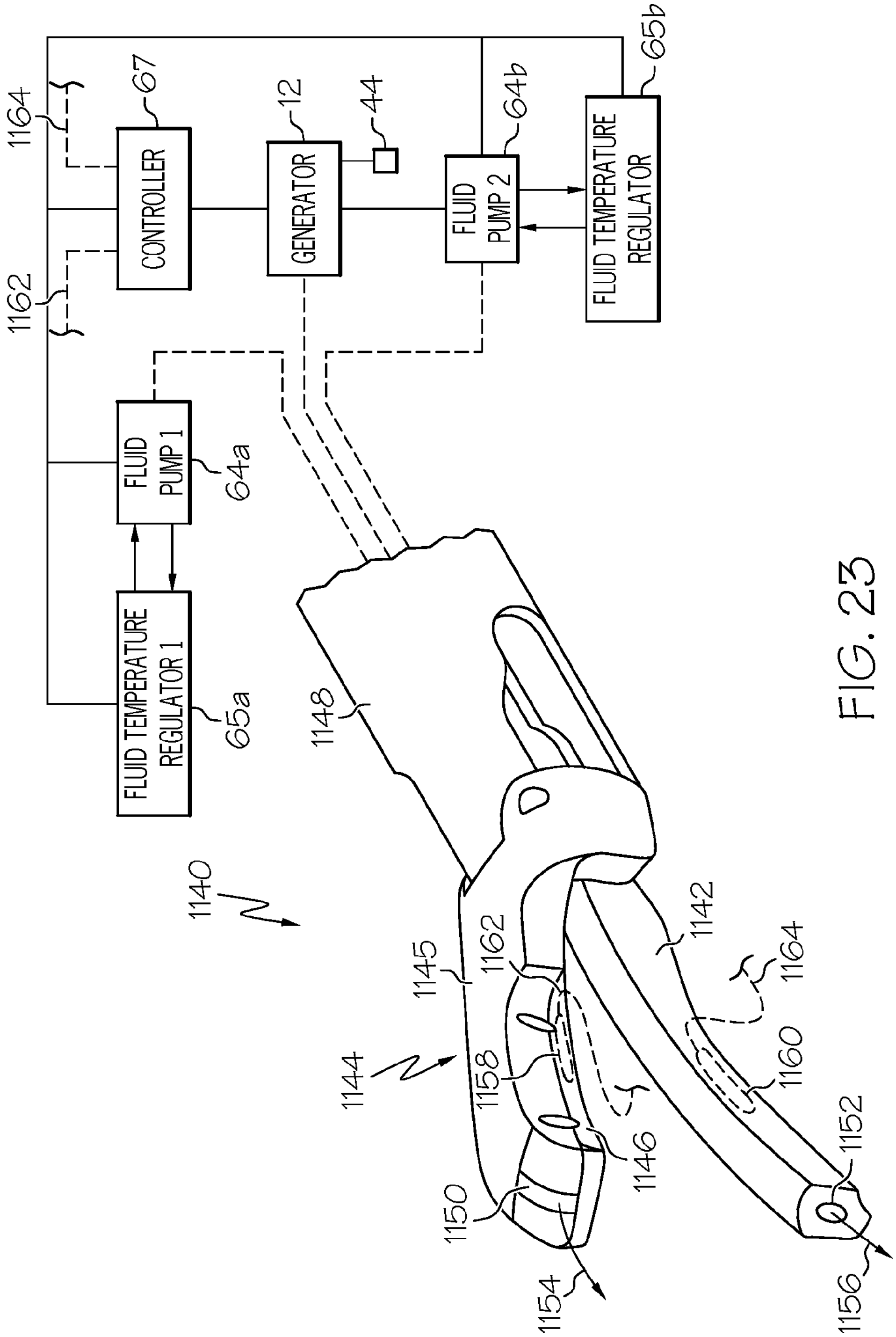
FIG. 23 illustrates one embodiment of a multi-element end effector comprising an ultrasonic end effector and a clamping mechanism.

FIG. 23 illustrates one embodiment of a multi-element end effector 1140 comprising an ultrasonic blade 1142 and a clamping mechanism 1144. The ultrasonic blade 1142 may be operated as previously described and will not be repeated here for the sake of brevity. The clamping mechanism 1144 is pivotally coupled to an elongated member or endoscopic portion 1148 of an ultrasonic instrument. The clamping mechanism 1144 comprises a clamp arm 1145 and a coaptation pad 1146. The clamping mechanism 1144 is adapted to clamp tissue between the coaptation pad 1114 and the ultrasonic blade 1142. The coaptation pad 1146 forms viable coagulation zones to improve the weld strength of the tissue.

In one embodiment, the clamp arm 1145 comprises an inner lumen 1150 to receive a first fluid 1154 from a fluid pump 64*a*. The fluid 1154 may be heated by a fluid temperature regulator 65*a* prior to flowing through the lumen 1150. In one embodiment, the ultrasonic blade 1142 comprises another inner lumen 1152 to receive a fluid 1156 from a fluid pump 64*b*. The fluid 1156 may be heated by a fluid temperature regulator 65*b* prior to flowing through the lumen 1152. The fluids 1150, 1152 may be the same or may be different fluids. The fluids 1150, 1152 may be supplied to the lumens 1150, 1152 from the same fluid source or from different fluid sources. For example, either one of the fluid pumps 64*a,b* and/or either one of the fluid temperature regulators 65*a,b* may supply the fluid to both lumens 1152, 1150.

As previously discussed, while in use, the temperature of the ultrasonic blade 1142 may be approximated by measuring the resonant frequency of the ultrasonic system. As the temperature of the blade 1142 varies, the resonant frequency of the ultrasonic system also varies. For example, as the temperature of the blade 1142 increases, the resonant frequency of the ultrasonic system decreases; and as the temperature of the blade 1142 decreases, the resonant frequency of the ultrasonic system increases. Accordingly, the temperature of the blade 1142 may be inferred by measuring the deviation of the resonant frequency from a reference frequency measured at a reference temperature point. In one embodiment, the temperature of the blade 1142 may be inferred and the deviation in the resonant frequency of the ultrasonic system may be measured and utilized to adjust the flow rate and/or temperature of the fluids 1154, 1156 flowing through the respective lumens 1150, 1152 into the surgical area. This mechanism may be employed to adjust the temperature of the blade 1142 and/or the coaptation pad 1146.

The actual frequency feedback mechanism and control required to maintain the blade 1142 and/or the pad 1146 at a predetermined temperature may be determined empirically by experimentation or design parameters and programmed into the ultrasonic signal generator 12, in an integrated circuit, or the controller 67, as previously discussed. The temperature of the either the pad 1146 and/or the blade 1142 may be controlled or regulated by flowing the respective fluids 1154, 1156 at predetermined or desired temperatures. For example, the blade 1142 may be cooled by flowing the fluid 1156 that is colder than the temperature of the blade 1142 as derived from the frequency measurement of the ultrasonic system. For example, the pad 1146 may be heated by flowing the fluid 1154 at a temperature that is higher than the temperature of the blade 1142 as derived from the frequency measurement of the ultrasonic system. The fluids 1154, 1156 may be flowed through the pad 1146 and/or the blade 1142 at a flow rate necessary to keep them at the predetermined temperature. In another embodiment, either one of the fluids 1154, 1156 may be heated by the fluid temperature regulator 65*a,b* to a desired temperature and then flowed through either one of the lumens 1150, 1152 at a suitable rate to transfer heat energy into or out of the system.

In one embodiment, the temperature of the pad 1146 and/or the blade 1142 may be measured with respective temperature sensors 1158, 1160. The first and second temperature sensors 1158, 1160 may be thermocouple or thermistor type devices and may be embedded in the elongated member or endoscopic portion 1148 or sheath, the blade 1142, the pad 1146, and/or other suitable portions of the clamping mechanism 1144 such as the clamp arm 1145, for example. The temperature sensors 1158, 1160 provide respective first and second temperature feedback signals 1162, 1164 to the controller 67 to correlate temperature of the pad 1146 or the blade 1142. In tissue welding applications, a strong coagulation area may be achieved by maintaining the temperature of the surface of the blade 1142 at a point between where coagulation of the tissue can occur but where desiccation of the tissue does not occur. Lowering the temperature of the blade 1142 enables the blade 1142 to contact the tissue for a longer period. This allows for both the side of the tissue in contact with the blade 1142 and the side in contact with the coaptation pad 1146 to form viable coagulation zones, thus improving the weld strength of the tissue.

In one embodiment, the temperature of the ultrasonic blade 1142 or the coaptation pad 1146 may be controlled by employing blade temperature measurement as a feedback mechanism and infusing water or other fluids 1154, 1156 at predetermined temperatures into the blade pad 1146 or the blade 1142 to maintain, regulate, or otherwise control their temperature. For example, infusing water at a specified temperature, at a specified flow rate, and for a specified period maintains the blade 1142 at that temperature and absorbs excess energy from the system that would otherwise desiccate the tissue. The temperature of the pad 1146 or the blade 1142 may be measured using either frequency change or variation of the system or by direct measurement with the sensors 1162, 1164. The temperature of the pad 1146 or the blade 1142 may be regulated by infusing the fluids 1154, 1156 therethrough at a predetermined temperature. In one embodiment, the fluid 1156 may be employed to cool the ultrasonic blade 1142 and to the fluid 1154 may be employed to heat the coaptation pad 1146 side of the instrument.

Figure 24:
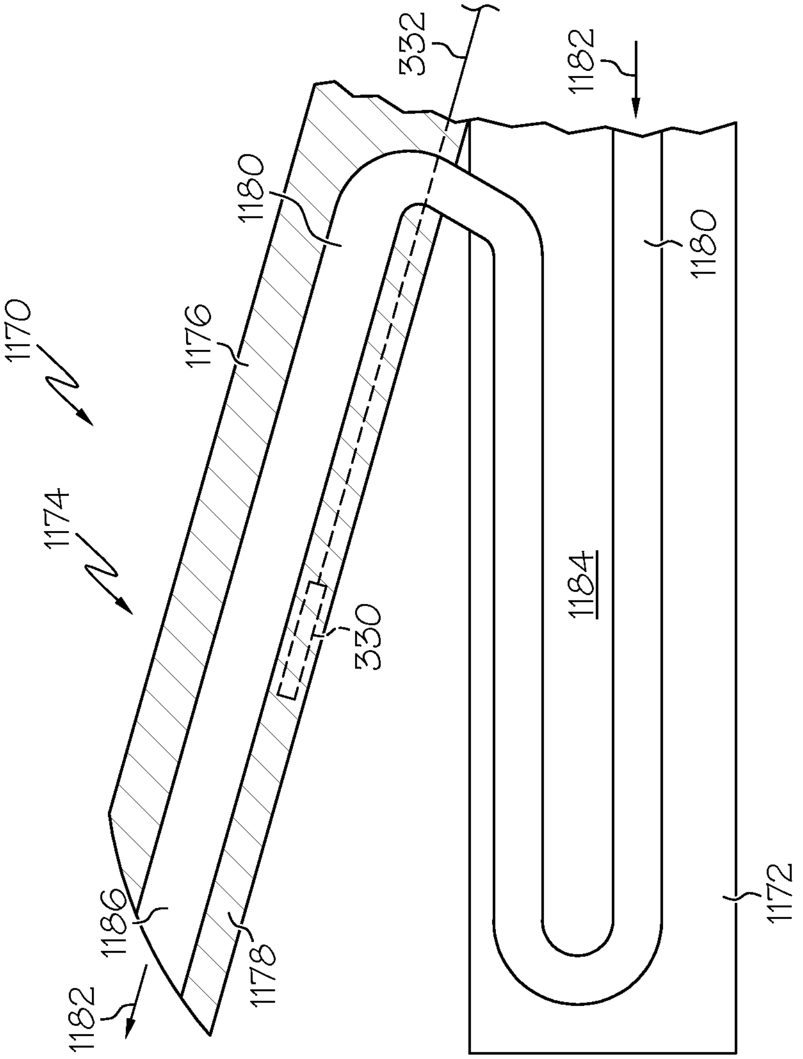
FIG. 24 illustrates one embodiment of a multi-element end effector comprising an ultrasonic end effector and a clamping mechanism.

FIG. 24 illustrates one embodiment of a multi-element end effector 1170 comprising an ultrasonic blade 1172 and a clamping mechanism 1174. The ultrasonic blade 1172 may be operated as previously described and the operation will not be repeated here for the sake of brevity. The clamping mechanism 1174 is pivotally coupled to an elongated member or endoscopic portion of an ultrasonic instrument. The clamping mechanism 1174 comprises a clamp arm 1176 and a coaptation pad 1178. The clamping mechanism 1174 is adapted to clamp tissue between the coaptation pad 1178 and the ultrasonic blade 1172. The coaptation pad 1178 forms viable coagulation zones to improve the weld strength of the tissue. In on embodiment, a fluid line 1180 is provided to receive a fluid 1182. The fluid line 1180 is located in a body portion 1184 of the blade 1172. The fluid line 1180 is then routed through the clamp arm 1176 and is located adjacent to the coaptation pad 1178. The fluid 1182 exits through an outlet port 1186 from the clamp arm 1176. Thus, the same blade cooling fluid 1182 is routed through the coaptation pad 1178 to increase the temperature of the tissue on the side opposing the blade 1172.

Figure 25:
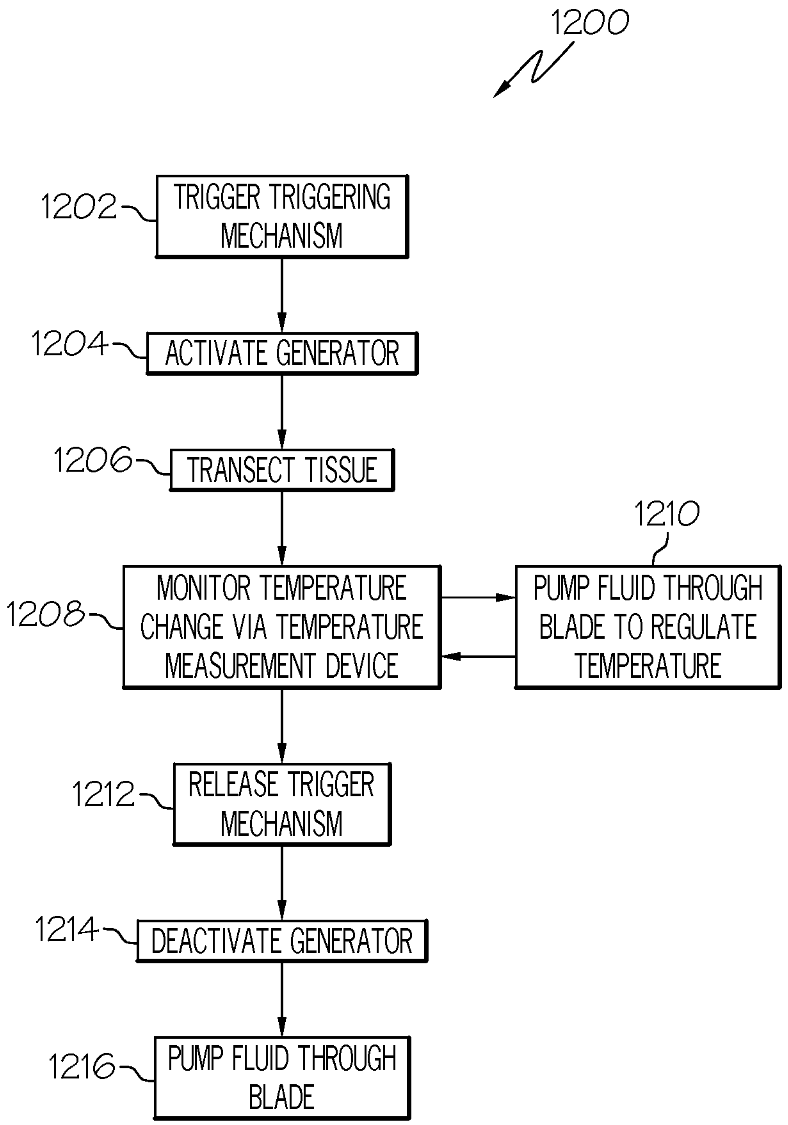
FIG. 25 is a diagram illustrating the operation of the ultrasonic instruments described herein employing an external temperature measurement device.

FIG. 25 is a diagram 1200 illustrating the operation of various embodiments of the ultrasonic instruments described herein employing an external temperature measurement device. In one embodiment, the temperature measurement device may comprise the temperature sensor 330 to provide a temperature feedback signal 332 to the controller 67 as described above with respect to FIGS. 12, 13, 16-20, 23, and 24. The temperature feedback signal 332 is provided to the controller 67 to regulate the fluid pump 64 and/or the fluid temperature regulator 65. The surgical procedure is initiated when the operator (e.g., the surgeon) triggers 1202 the triggering mechanism 44 to activate 1204 the generator 12. The operator employs the ultrasonic instrument to transect 1206 tissue. During the procedure, the elements of the ultrasonic system such as the generator 12 or the controller 67 monitor 1208 the temperature change of the ultrasonic blade by monitoring the temperature feedback signal 332 from the temperature sensor 330 located in proximity to the end effector. In one embodiment, the temperature sensor 330 may be located in the clamp arm assembly, embedded in the blade, or located within the sheath, or in proximity thereto. Based on the temperature feedback signal 332, the controller 67 operates the fluid pump 64 continuously or intermittently to pump fluid through the blade to maintain or regulate the temperature of the blade. To terminate the surgical procedure, the operator releases 1212 the triggering mechanism and deactivates 1214 that generator 12. The fluid pump 64 continues to pump fluid through the blade for a predetermined period or until the blade reaches a predetermined temperature. It is appreciated that in various embodiments fluid will not be pumped through the end effectors until the generator has been deactivated.

Figure 26:
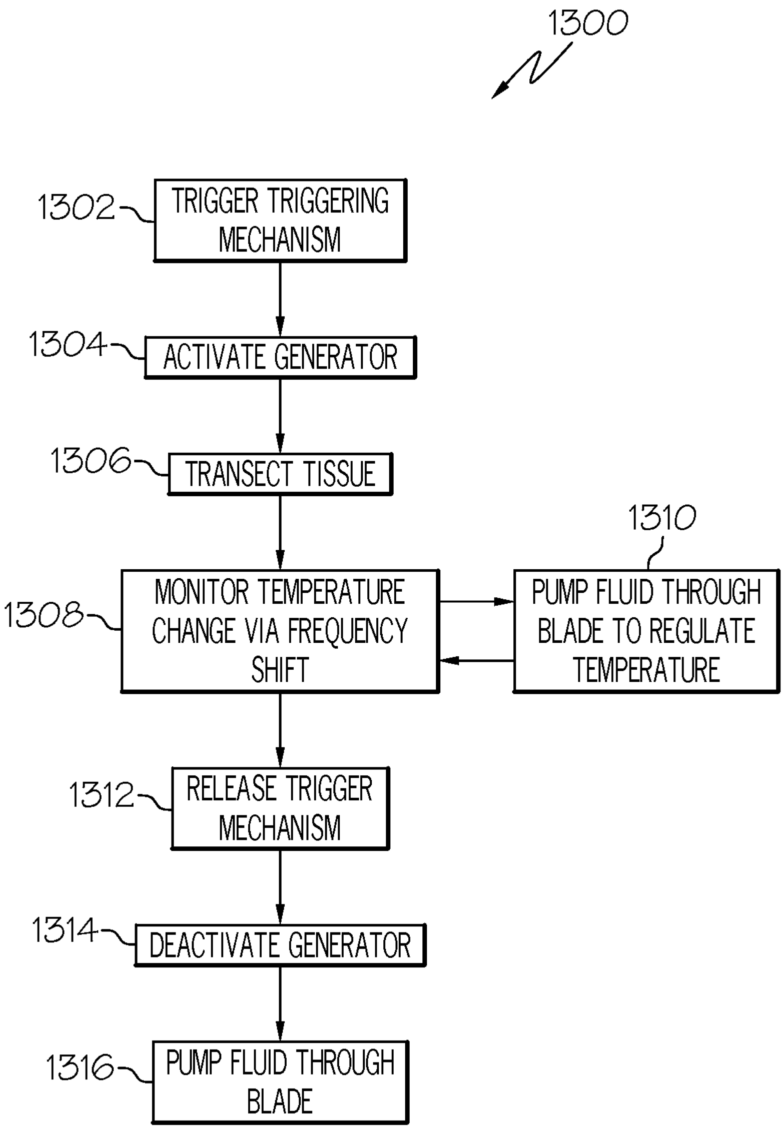
FIG. 26 is a diagram 1300 illustrating the operation of the ultrasonic instruments described herein employing a frequency shift temperature measurement technique.

FIG. 26 is a diagram 1300 illustrating the operation of various embodiments of the ultrasonic instruments described herein employing a frequency shift temperature measurement technique. In one embodiment, the frequency shift temperature measurement technique may be employed to derive the temperature of the ultrasonic blade based on the shift in resonant frequency generally attributed to the change in the temperature of the blade. These techniques employ the frequency feedback signal 71 as previously discussed with reference to FIGS. 8 and 10-17. The frequency shift may be measured by the generator 12 or the controller 67. The frequency feedback signal 71 is provided to the controller 67 to regulate the fluid pump 64 and/or the fluid temperature regulator 65. The surgical procedure is initiated when the operator (e.g., the surgeon) triggers 1302 the triggering mechanism 44 to activate 1304 the generator 12. The operator employs the ultrasonic instrument to transect 1306 tissue. During the procedure, the elements of the ultrasonic system such as the generator 12 or the controller 67 monitor 1308 the temperature change of the ultrasonic blade by monitoring the frequency feedback signal 71, which is proportional to the temperature of the ultrasonic blade. Based on the temperature feedback signal 332, the controller 67 operates the fluid pump 64 continuously or intermittently to pump fluid through the blade to maintain or regulate the temperature of the blade. To terminate the surgical procedure, the operator releases 1312 the triggering mechanism and deactivates 1314 that generator 12. The fluid pump 64 continues to pump fluid through the blade for a predetermined period or until the blade reaches a predetermined temperature. It is appreciated that in various embodiments fluid will not be pumped through the end effectors until the generator has been deactivated.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

FIGS. 7A, 7B, and 20-24 illustrate various embodiments comprising blades and clamp arm assemblies comprising proximal tissue pad segments, distal tissue pad segments and tissue pad insert segments. The pivotal movement of the clamp arm assemblies with respect to the blades may be affected by the provision of a pair of pivot points on the clamp arm portion of the clamp arm assembly that interfaces with an ultrasonic surgical instrument via weld pin fastening or other fastening means (not shown). The tissue pad segments may be attached to the clamp arm by mechanical means including, for example, rivets, glues, adhesives, epoxies, press fitting or any other fastening means known in the art. Furthermore, the tissue pad segments may be removably attached to the clamp arm by any known means.

In various embodiments, the clamp arm may comprise a T-shaped slot for accepting a T-shaped flange of a proximal tissue pad segment, a distal tissue pad segment and a tissue pad insert segment. In various embodiments, a single unitary tissue pad assembly may comprise the proximal tissue pad segment, the distal tissue pad segment and the tissue pad insert segment, and further comprise a T-shaped flange for reception in a T-shaped slot in the clamp arm assembly. Additional configurations including dove tailed-shaped slots and wedge-shaped flanges are contemplated. As would be appreciated by those skilled in the art, flanges and corresponding slots have alternative shapes and sizes to removably secure the tissue pad segments to the clamp arm.

A method for replacing the proximal tissue pad segment, the distal tissue pad segment and/or the tissue pad insert segment include one or more of the steps of: a) disengaging the clamp arm assembly from the ultrasonic surgical instrument; b) removing at least one of the tissue pad segments from the clamp arm; c) inserting at least one new or reconditioned tissue pad segment into the clamp arm; and d) engaging the clamp arm assembly with the ultrasonic surgical instrument. In this removal and replacement process, the new or reconditioned proximal tissue pad segment, distal tissue pad segment and tissue pad insert segment may be multiple separate segments or of unitary construction.

Another method for replacing the proximal tissue pad segment, the distal tissue pad segment and/or the tissue pad insert segment include one or more of the steps of: a) opening flanges on the clamp arm; b) removing at least one of the tissue pad segments from the clamp arm; c) inserting at least one new or reconditioned tissue pad segment into the clamp arm; and d) closing flanges on the clamp arm. In this removal and replacement process, the new or reconditioned proximal tissue pad segment, distal tissue pad segment and tissue pad insert segment may be multiple separate segments or of unitary construction.

Preferably, the various embodiments described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that the device is sterilized. This can be done by any number of ways known to those skilled in the art including beta or gamma radiation, ethylene oxide, steam.

Although various embodiments have been described herein, many modifications and variations to those embodiments may be implemented. For example, different types of end effectors may be employed. In addition, combinations of the described embodiments may be used. For example, a concave blade tip may be coated with a hydrophobic material. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical instrument, comprising:

a transducer configured to produce vibrations at a predetermined drive frequency;

an ultrasonic blade coupled to the transducer;

an ultrasonic transmission waveguide coupled between the transducer and the ultrasonic blade;

a controller to receive a feedback signal from at least the ultrasonic blade, wherein the feedback signal is a frequency variation between the predetermined drive frequency of the transducer and a resonant frequency of the transducer, wherein the frequency variation is measured by the controller, wherein the controller is configured to receive the feedback signal to measure and control a temperature of the ultrasonic blade, and wherein the resonant frequency of the transducer decreases as a temperature of at least the ultrasonic blade increases; and a lumen extending continuously at least through the ultrasonic blade, wherein the controller is configured to control fluid flow through the lumen when the resonant frequency of the transducer decreases, and wherein the lumen is adapted to couple to a fluid temperature regulator.

2. The surgical instrument of claim 1, wherein the feedback signal indicates an operation state of the ultrasonic blade.

3. The surgical instrument of claim 1, wherein the lumen extends longitudinally through the transducer and the ultrasonic transmission waveguide.

4. The surgical instrument of claim 1, comprising a fluid temperature regulator fluidically coupled to the lumen.

5. A surgical instrument, comprising a transducer configured to produce vibrations at a predetermined drive frequency;

an ultrasonic blade coupled to the transducer;

an ultrasonic transmission waveguide coupled between the transducer and the ultrasonic blade;

a controller to receive a feedback signal from at least the ultrasonic blade, wherein the feedback signal is measured by the controller; and wherein the controller detects a tissue load of the ultrasonic blade;

a lumen extending continuously at least through the ultrasonic blade, wherein the controller is configured to control fluid flow through the lumen when the resonant frequency of the transducer decreases, and wherein the lumen is configured to couple to a fluid temperature regulator; and a temperature sensor to measure the temperature of the ultrasonic blade and to provide the feedback signal, wherein the feedback signal is proportional to the temperature of the ultrasonic blade.

6. A system, comprising:

a transducer configured to produce vibrations at a predetermined frequency;

an ultrasonic blade;

an ultrasonic transmission waveguide coupled between the transducer and the ultrasonic blade;

a controller to receive a feedback signal from the ultrasonic blade, wherein the feedback signal is derived from frequency variations of the ultrasonic blade from the predetermined frequency, wherein the controller is configured to receive the feedback signal to measure and control a temperature of the ultrasonic blade, and wherein the feedback signal is proportional to the temperature of at least the ultrasonic blade;

a lumen extending continuously at least through the ultrasonic blade, wherein the resonant frequency of the transducer decreases as a temperature of at least the ultrasonic blade increases, and wherein the controller is configured to control fluid flow through the lumen when the resonant frequency of the transducer decreases; and a fluid temperature regulator in electrical communication with the controller, wherein the lumen is coupled to the fluid temperature regulator.

7. The system of claim 6, comprising:

a generator coupled to the controller; and a triggering mechanism in electrical communication with the generator to activate the generator.

8. The system of claim 7, further comprising a pump in fluid communication with the lumen and electrical communication with the controller.

9. A surgical instrument, comprising:

a transducer configured to produce vibrations at a predetermined frequency;

a signal generator coupled to the transducer;

an ultrasonic blade;

an ultrasonic transmission waveguide coupled between the transducer and the ultrasonic blade;

a controller to receive a feedback signal from the ultrasonic blade, wherein the feedback signal is derived from frequency variations of the ultrasonic blade from the predetermined frequency, wherein the controller is configured to receive the feedback signal to measure and control a temperature of the ultrasonic blade, and wherein the feedback signal is proportional to the temperature of at least the ultrasonic blade; and a lumen extending continuously at least through the ultrasonic blade, wherein the controller is configured to control fluid flow through the lumen when the resonant frequency of the transducer decreases, wherein the resonant frequency of the transducer decreases as a temperature of at least the ultrasonic blade increases, and wherein the lumen is adapted to couple to a fluid temperature regulator.

10. The surgical instrument of claim 9, wherein the transducer has a first state in which the transducer is driven by the signal generator and a second state in which the transducer is not driven by the signal generator.

11. The surgical instrument of claim 10, further comprising a pump in fluid communication with the lumen and electrical communication with the controller, wherein the controller delivers the signal to the pump during the second state.

12. The surgical instrument of claim 11, wherein the fluid is conducted through the lumen for a predetermined period of time.

13. The surgical instrument of claim 12, wherein the fluid is conducted through the lumen for a predetermined repeating cycle.

14. The surgical instrument of claim 9, comprising a fluid temperature regulator fluidically coupled to the lumen.

* * * * *